(12) United States Patent
Augustijns et al.

(10) Patent No.: US 8,258,137 B2
(45) Date of Patent: Sep. 4, 2012

(54) PROCESS FOR RELEASE OF BIOLOGICALLY ACTIVE SPECIES FROM MESOPOROUS OXIDE SYSTEMS

(75) Inventors: Patrick Augustijns, Heverlee (BE); Johan Adriaan Martens, Huldenberg (BE); Randy Mellaerts, Heverlee (BE); Guy Van Den Mooter, Pellenberg (BE)

(73) Assignee: Katholieke Universiteit Leuven, Leuven (BE)

( * ) Notice: Subject to any disclaimer, the term of this patent is extended or adjusted under 35 U.S.C. 154(b) by 496 days.

(21) Appl. No.: 12/361,381

(22) Filed: Jan. 28, 2009

(65) Prior Publication Data

US 2009/0192205 A1   Jul. 30, 2009
US 2009/0318519 A2   Dec. 24, 2009
US 2011/0060020 A9   Mar. 10, 2011

Related U.S. Application Data

(60) Provisional application No. 61/024,324, filed on Jan. 29, 2008.

(51) Int. Cl.
*A61K 31/497* (2006.01)
*A61K 8/02* (2006.01)

(52) U.S. Cl. ..................... 514/252.1; 424/401
(58) Field of Classification Search .......... None
See application file for complete search history.

(56) References Cited

U.S. PATENT DOCUMENTS 6,669,924 B1   12/2003   Kaliaguine et al.
6,755,364 B2 *  6/2004   Lugmair et al. ............. 241/24.1
2006/0134219 A1 *  6/2006   Martens et al. ............... 424/489

FOREIGN PATENT DOCUMENTS

WO   WO 99/36357   7/1999

OTHER PUBLICATIONS

Miller, D. A., Ph.D. Dissertation, "Improved Oral Absorption of Poorly Water-Soluble Drugs by Advanced solid dispersion systems", Proquest Dissertations, University of Texas—Austin, Dec. 2007, Abstract (vii-viii).*
Sher, P.; Ingavle, G,; Ponrathnam, S.; Pawar, A. P. Microporous and Mesoporous Materials, 2007, v. 102, 290-298).*
Mellaerts, R.; Mols, R.; Jammaer, J. A. G.; Aerts, C. A.; Annaert, P.; Van Humbeeck, J.; Van den Mooter, G.; Augustijns, P.; Martens, J.A., European Journal of Pharmaceutics and Biopharmaceutics, 2008, v. 69, 223-230.*
Ambrogi et al., "Improvement of Dissolution Rate of Piroxicam by Inclusion into MCM-41 Mesoporous Silicate" *European Journal of Pharmaceutical Sciences* 32:216-222 (2007).
Han et al., "Mesoporous Silicate Sequestration and Release of Proteins" *J. Am. Chem. Soc.* 121:9897-9898 (1999).

(Continued)

*Primary Examiner* — Johann Richter
*Assistant Examiner* — Erin Hirt
(74) *Attorney, Agent, or Firm* — Clark & Elbing LLP

(57) ABSTRACT

A process for the release of a biologically active species comprising the steps of:
providing a mesoporous oxide-based material having structural order and at least one level of porosity;
fixing or immobilizing said biologically active species in said ordered mesoporous oxide; and
providing said ordered mesoporous oxide with said fixed or immobilized biologically active species in vivo thereby realizing intraluminally induced substantially pH-independent supersaturation of said biologically active species resulting in enhanced transepithelial transport; wherein said biologically active species is a poorly soluble therapeutic drug classified as belonging to Class II or Class IV of the Biopharmaceutical Classification System and said ordered mesoporous oxide has a pore size in the range of 4 to 14 nm.

27 Claims, 23 Drawing Sheets

OTHER PUBLICATIONS

Heikkila et al., "Evaluation of Mesoporous TCPSi, MCM-41, SBA-15, and TUD-1 Materials as API Carriers for Oral Drug Delivery" *Drug Delivery* 14:337-347 (2007).

Horcajada et al., "Influence of Pore Size of MCM-41 Matrices on Drug Delivery Rate" *Microporous and Mesoporous Materials* 68:105-109 (2004).

Ma et al., "Large-pore Mesoporous Silica Spheres: Synthesis and Application in HPLC" *Colloids and Surfaces A: Physicochem. Eng. Aspects* 229:1-8 (2003).

Mellaerts et al., "Enhanced Release of Itraconazole from Ordered Mesoporous SBA-15 Silica Materials" *Chem. Commun.* 1375-1377 (2007).

Munoz et al., "MCM-41 Organic Modification as Drug Delivery Rate Regulator" *Chem. Mater.* 15:500-503 (2003).

Vallet-Regi et al., "A New Property of MCM-41: Drug Delivery System" *Chem. Mater.* 13:308-311 (2001).

Zhao et al., "Triblock Copolymer Syntheses of Mesoporous Silica with Periodic 50 to 300 Angstrom Pores" *Science* 279:548-552 (1998).

* cited by examiner

Figure 22
itraconazole
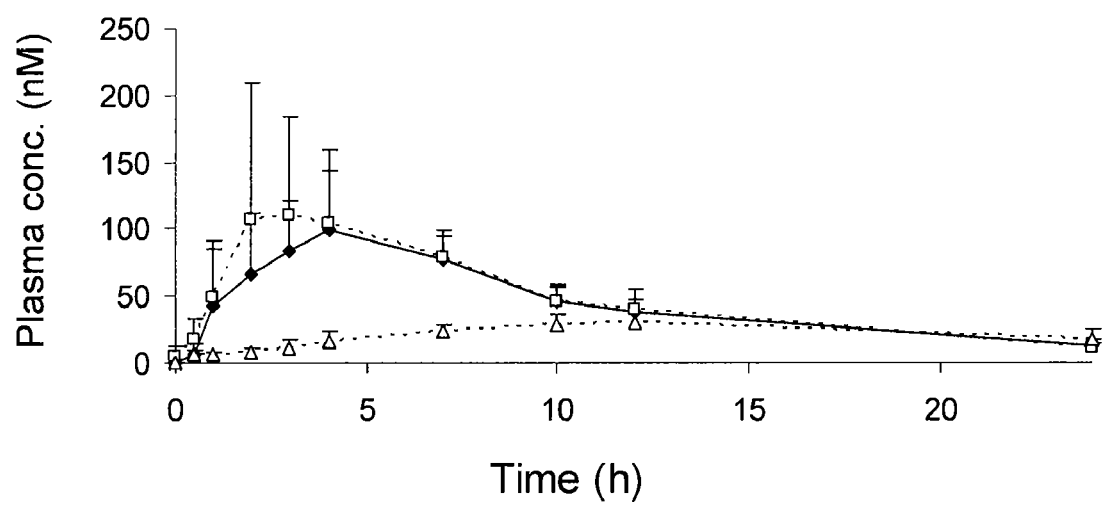
hydroxyitraconazole
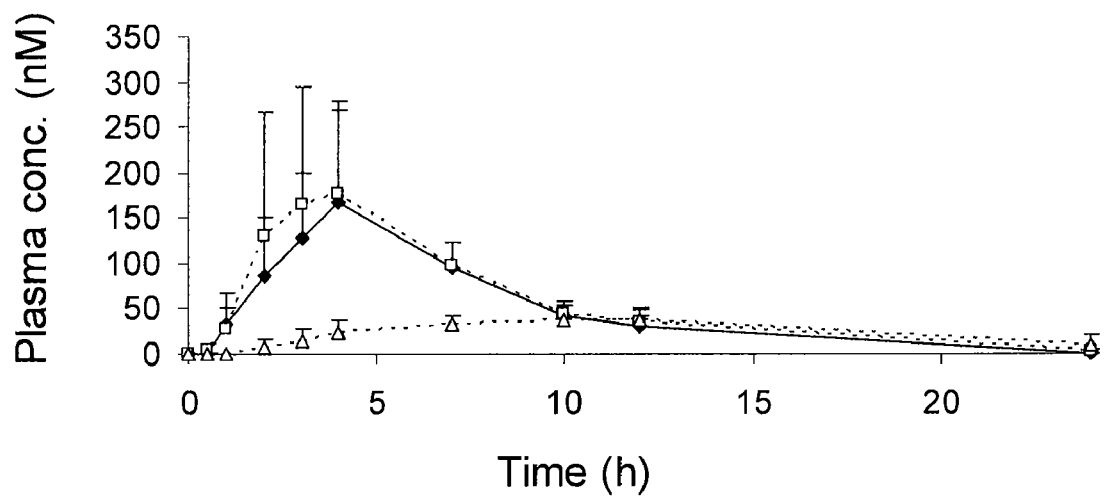

PROCESS FOR RELEASE OF BIOLOGICALLY ACTIVE SPECIES FROM MESOPOROUS OXIDE SYSTEMS

CROSS-REFERENCE TO RELATED APPLICATIONS

This application claims the benefit of the filing date of U.S. Application Ser. No. 61/024,324, filed Jan. 29, 2008, the disclosure of which is hereby incorporated by reference.

FIELD OF THE INVENTION

The present invention concerns a process for the release of a biologically active species.

BACKGROUND OF THE INVENTION

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silica's commonly used in catalyst formulations and the paracrystalline transitional aluminas used as solid acid catalysts and petroleum reforming catalyst supports. The term "amorphous" is used herein to indicate a material with no long-range order, although almost all materials are crystalline to some degree, at least on the local scale. An alternate term that has been used to describe these materials is "X-ray indifferent". The microstructure of silica's consists of 10 to 25 nm particles of dense amorphous silica, with porosity resulting from voids between the particles. Since there is no long-range order in these materials, the pore sizes tend to be distributed over a rather large range. This lack of order also manifests itself in the X-ray diffraction pattern, which is usually featureless.

Paracrystalline materials such as the transitional aluminas also have a wide distribution of pore sizes, but have better defined X-ray diffraction patterns usually consisting of a few broad peaks. The microstructure of these materials consists of tiny crystalline regions of condensed alumina phases and the porosity of the materials results from irregular voids between these regions. Since, in the case of either material, there is no long-range order controlling the sizes of pores in the material, the variability in pore size is typically quite high. The sizes of pores in these materials fall into a regime called the mesoporous range, which is from about 1.3 nm to about 20 nm.

Generally, porous substances are divided by pore size, for example, pore sizes smaller than 2 nm classified as microporous substances, between 2 and 50 nm classified as mesoporous substances and larger than 50 nm classified as macroporous substances. Of the porous substances, those having uniform channel, such as zeolite, are defined as molecular sieves and up to hundreds of types of species have been found and synthesized thus far. Zeolites play an important role as catalysts or carriers in modern chemical industries by virtue of their characteristics including selective adsorptivity, acidity and ion exchangeability.

U.S. Pat. No. 6,630,170 discloses a mesoporous composition prepared from a mixture comprising hydrochloric acid, vitamin E and a silica source, wherein said vitamin E functions as a templating molecule, and said mesoporous composition exhibits uniform pore size.

Another difficult problem for the pharmaceutical industry is the formulation of drugs having low or very low water-solubility into solid dosage forms, especially formulations intended for immediate release. Few solutions to this problem have been disclosed in the art. For instance, US 2001/0048946A provides solid dosage forms of sparingly water-soluble pharmaceutical agents, i.e. solid or crystalline drugs having a water-solubility of 10 to 33 µg/mL at 25° C., such as glitazones. More particularly, this document discloses a pharmaceutical composition in the form of a solid particulate dispersion of such a pharmaceutical agent dispersed throughout a matrix of a water-soluble polymer such as polyvinylpyrrolidone, hydroxy-propyl cellulose, or hydroxypropyl methylcellulose. In a preferred embodiment, the particulate pharmaceutical agent is dispersed in the water-soluble polymer in a weight ratio of about 10% to about 90% active ingredient to about 90% to about 10% polymer. Other conventional excipients such as glycerin, propyleneglycol, Tween, stearic acid salts and the like can be added.

US 2001/0044409A discloses a process for the preparation of a poorly water soluble drug in solid dispersion comprising the steps of (a) blending the drug with a carrier, (b) dissolving a surfactant and a plasticizer/solubilizer in water, (c) spraying the surfactant-plasticizer/solubilizer solution onto the drug/carrier mixture in a fluid bed granulator, (d) extruding the resulting granulation through a twin screw extruder with at least one heating zone, and (e) milling the extrudate to a powdery mass of the solid drug dispersion. Within this process, the carrier may be selected from the group consisting of polyvinylpyrrolidone, high molecular weight polyethylene glycol, urea, citric acid, vinyl acetate copolymer, acrylic polymers, succinic acid, sugars and mixtures thereof; the plasticizer/solubilizer may be selected from the group consisting of low molecular weight polyethylene glycol, propylene glycol, glycerin, triacetin, triethyl citrate, sugar alcohols and mixtures thereof, and the said surfactant may be selected from the group consisting of Tween, Span, Pluronics, polyoxyethylene sorbitol esters, monodiglycerides, polyoxy-ethylene acid polyoxyethylene alcohol and mixtures thereof. This process suffers from the disadvantage of providing a heating zone in the twin-screw extruder and consequently controlling and monitoring the temperature profile of the extruder.

However, none of the above processes appear to be successful in formulating solid dosage forms of drugs having very low water-solubility, i.e. a solubility lower than 10 µg/mL, preferably lower than 5 µg/mL. This problem is applicable to a large number of drugs, including those belonging to the family of diaminopyrimidines, such as stated in U.S. Pat. No. 6,211,185.

U.S. Pat. No. 3,639,637 discloses oestrogen compositions for the preparation of stable aqueous suspensions that can be sprayed onto animal feed, comprising (by weight) 70-95% of water-dispersible gel-forming microcrystalline cellulose and 5-30% of finely-divided diethylstilbestrol (a compound which is virtually insoluble in water) and optionally further up to one third of the weight of the composition of a hydrocolloid selected from the group consisting of sodium carboxy-methylcellulose, methylcellulose and hydroxyethylcellulose. The two latter cellulose compounds are known, namely from EP-A-403 383, to contribute to an extended linear drug release rate.

WO-A-99/12524 solves the problem of drug formulations with both a relatively fast or quick onset of the therapeutic effect and the maintenance of a therapeutically active plasma concentration for a relatively long period of time, by providing an oral modified release multiple-units composition wherein the unit dosage form comprises at least (i) a first fraction being able to release at least 50% of the drug within the first 20 minutes of a certain dissolution method, and (ii) a second fraction for delayed and extended release of the drug. The multiple-units of the first fraction may be granulates or, provided that a surfactant is added to the formulation, coated or uncoated pellets. Formulation of the first fraction depends on the specific drug but typically includes wet-granulation, and an antacid-like or other alkaline substance was found to have a pronounced increasing effect on the release rate.

U.S. Pat. No. 5,646,131 discloses (example 4) rapidly dissolving capsules containing a granulate formulation of a water-insoluble or sparingly soluble drug, such as terfenadine (less than 0.01 mg/mL water-solubility), surfactants (Tween 80 and sodium lauryl sulfate), cyclodextrin, Avicel PH 101 (microcrystalline cellulose) and a disintegrant/swelling agent (Primojel®, i.e. sodium carboxymethyl starch) in a weight ratio of 10:72 to Avicel. These capsules provide better drug absorption, due to the presence of cyclodextrin, as evidenced by the figure showing a 90% drug release within 45 minutes.

U.S. Pat. No. 4,235,892 discloses a series of 1-aryl-2-acylamido-3-fluoro-1-propanol antibacterial agents including D-(threo)-1-p-methylsulfonyl phenyl-2-dichloroacetamido-3-fluoro-1-propanol, an antibacterial agent known as florfenicol and useful for veterinary purposes. Florfenicol has low solubility in water (about 1.3 mg/mL), as well as in many pharmaceutically acceptable organic solvents such as 1,2-propanediol, glycerin, and benzyl alcohol. For oral administration, these 1-aryl-2-acylamido-3-fluoro-1-propanol may be compounded in the form of tablets, or may even be admixed with animal feed. U.S. Pat. No. 4,235,892 therefore discloses making tablets by compressing granules of a composition comprising the said 1-aryl-2-acylamido-3-fluoro-1-propanol (in a drug loading range from 8.3% to 41.7% by weight), lactose, microcrystalline cellulose, starch and magnesium stearate.

The Biopharmaceutical Classification System (hereinafter referred as BCS) according to G. Amidon et al. in *Pharm. Res.* (1995) 12:413-420 provides for two classes of poorly soluble drugs, i.e. Class II and Class IV, and a class of highly soluble drugs, i.e. Class I. According to M. Martinez et al., Applying the Biopharmaceutical Classification System to Veterinary Pharmaceutical Products (Part I: Biopharmaceutics and Formulation Consideration) in *Advanced Drug Delivery Reviews* (2002) 54:805-824, a drug substance should be classified as highly soluble when the highest dose strength is soluble in at most 250 mL of aqueous media over the pH range 1-7.5. In view of its water solubility (1.3 mg/mL) and of a maximal dose of 20 mg/kg for pigs, it is easy to calculate that the highest dose strength of florfenicol administered to pigs is soluble in an amount of water, which is well above the limit value for the definition of a class I BCS highly soluble drug. Furthermore it is known from J. Voorspoels et al. in *The Veterinary Record* (October 1999) that florfenicol has a good oral bioavailability, so that it can be classified as a Class II compound as it is not a highly soluble drug and it shows no absorption problems.

There is a specific need in the art to provide a solid formulation of drugs with a water-solubility like florfenicol or lower. Florfenicol is a drug for oral administration to warm-blooded animals, such as cattle with naturally-occurring bovine respiratory disease, swine, sheep, goats and poultry, which at present is only available in the form of injectable solutions. Until now the skilled person has failed in the design of such a solid formulation of florfenicol, which can further be admixed with animal feed if necessary. Also there is a need for a solid formulation for low solubility drugs for human therapies.

Previous data demonstrate that in the case of drugs that are (weak) bases, the ability to create supersaturated solutions depends on gastric acidity. In the case of physiological malfunctions associated with hypochlorhydria or achlorhydria, however, the condition of an initial acidic environment to dissolve basic drugs is not fulfilled. Achlorhydria and hypochlorhydria refer to a disorder in which the production of gastric acid in the stomach is absent or low, respectively. Relying merely on the gastrointestinal acid-base sequence for enhancing bioactivity thus holds the risk of uncontrolled precipitation of the drug compound at the site of absorption.

These conditions are associated with various other medical problems, which also need treatment. The decreased acid level itself causes few symptoms, but low acid levels in the stomach are linked with bacterial overgrowth (as the stomach does not kill microbes normally present in food), which can manifest itself as diarrhea or decreased absorption of nutrients or vitamins. Risk of particular infections, such as *Vibrio vulnificus* (commonly from seafood) is increased. These infections may need specific drug treatments with the drug needing to dissolve in a non-acidic environment or in the presence of an abnormally small amount of hydrochloric acid.

There are several underlying causes for achlorhydria or hypochlorhydria such as: autoimmune disorders where there is antibody production against parietal cells, which normally produce gastric acid; a symptom of rare diseases such as mucolipidosis (type IV).

A symptom of *Helicobacter pylori* infection which neutralizes and decreases secretion of gastric acid to aid its survival in the stomach; a symptom of pernicious anemia, atrophic gastritis, VIPomas or of stomach cancer or adiation therapy involving the stomach. These conditions may need specific treatment by drugs that have to dissolve in a non-acidic environment or of presence of an abnormally small amount of hydrochloric acid.

Other conditions of decreased acidity in the stomach can, for instance, often be observed in HIV infected patients; therefore significant effects on the oral bioavailability of poorly water soluble compounds and on the success of the formulation strategy mentioned before can be expected.

The same hurdle is encountered in 10 to 20% of elderly people as they exhibit either diminished (hypochlorhydria) or no gastric acid secretion (achlorhydria), leading to basal gastric pH values >5.0. Such patient group are thus in need of oral medicated treatments by dosage form that allow various classes of drug entities for the treatment for various disorders to dissolve in non-acidic environment or of presence of an abnormally small amount of hydrochloric acid.

An example of the problems related to gastric pH is, for instance, a recent study on the direct influence of gastric pH on atazanavir absorption. When lansoprazole, a proton pump inhibitor, was co-administered with atazanavir, a drastic reduction in bioavailability of atazanavir was observed.

Similar behavior was also reported for the bead-based capsules of Sporanox® which exhibit a significantly lower oral bioavailability of itraconazole when dosed to human subjects suffering from a reduced acidity of the stomach. This indicates that the co-dissolving HPMC phase cannot enhance the extent of absorption when hypochlorhydria is involved. It is therefore often recommended to co-administer an acidic soda beverage in patients who use the capsule formulation of itraconazole.

Similar problems, yet unsolved in a suitable manner, arise with a growing number of therapeutic drugs with poor solubility like for instance itraconazole and diazepam. Solving such problems constitutes another goal of the present invention.

SUMMARY OF THE INVENTION

A problem in the art is that such compounds may suffer from insufficient dissolution throughout the gastrointestinal tract and therefore achieve inferior systemic exposure after oral administration. Present invention provides a solution to this problem. Today, deficient bioavailability is one of the main reasons for abandoning innovative oral drug candidates. Circumventing low solubility and unfavorable dissolution equilibrium kinetics are key issues in the development of an appropriate formulation.

The present invention provides an attractive strategy to enhance oral bioavailability by the use of a formulation, which creates supersaturation in the gastro-intestinal environment and maintains the drug concentrations many times higher than the thermodynamic solubility during a sufficient time period so that an enhanced absorption is achieved.

Surprisingly the present invention achieves local supersaturation of a poorly water-soluble biologically active species or drug by means of a novel formulation strategy based on ordered mesoporous oxides, e.g. silica, having one or more levels of porosity and structural order, such as for instance the molecular sieves with precisely repeating crystalline structure (microstructure) which are characterized by very narrow pore size distributions and X-ray diffraction patterns which show several characteristic peaks at diffraction angles above 3 degrees ($2\theta=6°$), for example crystalline mesoporous silica oxide-based materials, (hereinafter collectively referred to as ordered mesoporous oxide) as a carrier to entrap or incorporate the poorly soluble biologically active species or drug. Moreover, supersaturation is achieved without the addition of any dissolution enhancing surfactants.

Furthermore, we demonstrate that pH-independency can be generated by intraluminally-induced supersaturation of a poorly soluble drug, such as for instance the model compound itraconazole. Moreover, it is also demonstrated that this has a beneficial effect on the extent of absorption in the Caco-2 system and the rat in situ perfusion system. Caco-2 cell monolayer is a recognized model in determining the intestinal drug absorption of potential drug candidates as such and for delivery systems as well as the elucidation of the drug absorption promoting effect of various excipients. These effects have been confirmed by mammalian studies.

Due to the supersaturation effect, the drug formulations of the present invention are capable of exhibiting bioavailability enhancement over the correspondingly existing drug formulations of the prior art without requiring the addition of an absorption-enhancing agent.

The present invention provides a solution to the problem of gastric pH by the use of a formulation or dosage form which creates supersaturation in non-acidic gastro-intestinal environments or in a gastro-intestinal environment of an abnormally small amount of hydrochloric acid and which maintains the drug concentrations many times higher than the thermodynamic solubility during a sufficient time period so that an enhanced absorption and thus improved oral bioavailability is achieved. Such formulation strategy is based on the drug or biologically active species of poor basic water solubility being loaded in or entrapped in the pores of ordered mesoporous silica such as for instance molecular sieves with precisely repeating crystalline structure (microstructure) which are characterized by a very narrow pore size distributions and X-ray diffraction patterns which shows several characteristic peaks at angles of diffraction above 3 degrees ($2\theta=6°$), for instance crystalline mesoporous silica oxide-based materials with can have one or more levels of porosity and structural order or for instance substantially crystalline mesoporous oxide based materials having two or more levels of porosity (hereinafter collectively referred to as ordered mesoporous oxide) as a carrier to entrap or incorporate the poorly soluble biologically active species or drug.

Due to their pH-independent release profile, the drug formulations of the present invention are capable of being highly effective not only for the vast majority of patients with a normal level of hydrochloric acid in the stomach, but also with a group of patients with an abnormally low level of hydrochloric acid in the stomach (deficiency of hydrochloric acid in the gastric juice), such as patients with hypochlorhydria and achlorhydria, whatever the cause (auto-immune disorders, use of antacids, mucolipidosis type IV, *Helicobacter pylori* infection) of that condition, and related conditions such as, but not limited to, pernicious anemia, atrophic gastritis, radiation therapy involving the stomach, and the like. Consequently the above-described drug formulations are useful when administered in methods of treatment of all such conditions and diseases. This aspect of the invention is especially useful for formulating drugs having physical and/or chemical characteristics similar to that of itraconazole, e.g. (a) a similar molecular weight, (b) a similar molecular volume, and/or (c) a similar hydrophilicity.

Aspects of the present invention are realized by a process for the release of a biologically active species comprising the steps of:

providing a mesoporous oxide-based material having structural order and at least one level of porosity;

fixing or immobilizing said biologically active species in said ordered mesoporous oxide; and providing said ordered mesoporous oxide with said fixed or immobilized biologically active species in vivo thereby realizing intraluminally induced substantially pH-independent supersaturation of said biologically active species, i.e. at concentrations in a gastric medium above its saturation solubility, resulting in enhanced transepithelial transport;

wherein said biologically active species is a poorly soluble therapeutic drug classified as belonging to Class II or Class IV of the Biopharmaceutical Classification System; and preferably provided that when said ordered mesoporous oxide-based material has a single level of porosity and structural order it is obtained in the absence of an alpha-tocopherol polyethylene glycol ester templating biomolecule.

A further embodiment of a process for the release of a biologically active species comprising the steps of:

providing a mesoporous oxide-based material having structural order and at least one level of porosity;

fixing or immobilizing said biologically active species in said ordered mesoporous oxide; and providing said ordered mesoporous oxide with said fixed or immobilized biologically active species in vivo thereby realizing a substantially pH-independent release of said biologically active species at concentrations in a gastric medium above its saturation solubility resulting in enhanced transepithelial transport;

wherein said biologically active species is a poorly soluble therapeutic drug classified as belonging to Class II or Class IV of the Biopharmaceutical Classification System; and preferably provided that when said ordered mesoporous oxide-based material has a single level of porosity and structural order it is obtained in the absence of an alpha-tocopherol polyethylene glycol ester templating biomolecule.

Another embodiment of a process for the release of a biologically active species, according to the present invention, comprises the steps of:

providing a mesoporous oxide-based material having structural order and at least one level of porosity;

fixing or immobilizing said biologically active species in said ordered mesoporous oxide; and ingestion of said ordered mesoporous oxide with said fixed or immobilized biologically active species in a mammal or human body thereby in contact with gastric fluid (media) realizing intraluminally induced substantially pH-independent supersaturation of said biologically active species, i.e. at concentrations in a gastric medium above its saturation solubility, resulting in enhanced transepithelial transport in said mammal or human body;

wherein said biologically active species is a poorly soluble therapeutic drug classified as belonging to Class II or Class IV of the Biopharmaceutical Classification System; and preferably provided that when said ordered mesoporous oxide-based material has a single level of porosity and structural order it is obtained in the absence of an alpha-tocopherol polyethylene glycol ester templating biomolecule.

Another embodiment of a process for the release of a biologically active species comprising the steps of:

providing a mesoporous oxide-based material having structural order and at least one level of porosity;

fixing or immobilizing said biologically active species in said ordered mesoporous oxide; and ingestion of said ordered mesoporous oxide with said fixed or immobilized biologically active species in a mammal or human body thereby realizing a substantially pH-independent release of said biologically active species at concentrations in a gastric medium above its saturation solubility resulting in enhanced transepithelial transport in said mammal or human body;

wherein said biologically active species is a poorly soluble therapeutic drug classified as belonging to Class II or Class IV of the Biopharmaceutical Classification System; and preferably provided that when said ordered mesoporous oxide-based material has a single level of porosity and structural order it is obtained in the absence of an alpha-tocopherol polyethylene glycol ester templating biomolecule.

Another embodiment of the process for the release of a biologically active species, according to the present invention, comprises the steps of:

providing a mesoporous oxide-based material having structural order and at least one level of porosity;

fixing or immobilizing said biologically active species in said ordered mesoporous oxide; and ingestion of said ordered mesoporous oxide with said fixed or immobilized biologically active species in a mammal or human body thereby realizing a release of said biologically active species independent of intraluminal pH sequence at concentrations of said biologically active species in a gastric fluid above its saturation solubility resulting in enhanced transepithelial transport in said mammal or human body;

wherein said biologically active species is a poorly soluble therapeutic drug classified as belonging to Class II or Class IV of the Biopharmaceutical Classification System; and preferably provided that when said ordered mesoporous oxide-based material has a single level of porosity and structural order it is obtained in the absence of an alpha-tocopherol polyethylene glycol ester templating biomolecule.

Further embodiments of the present invention are disclosed in the detailed description.

BRIEF DESCRIPTION OF THE DRAWINGS

FIG. 22 shows plasma concentration-time profiles of itraconazole and hydroxy-itraconazole after single dosing with ordered mesoporous oxide loaded with itraconazole (♦), Sporanox® (□), or crystalline itraconazole (Δ) in rabbits (n=5), concentrations being normalized to the dose provided by the ordered mesoporous oxide capsules (8.1 mg).

DETAILED DESCRIPTION OF THE INVENTION

Definitions

Figure 1:
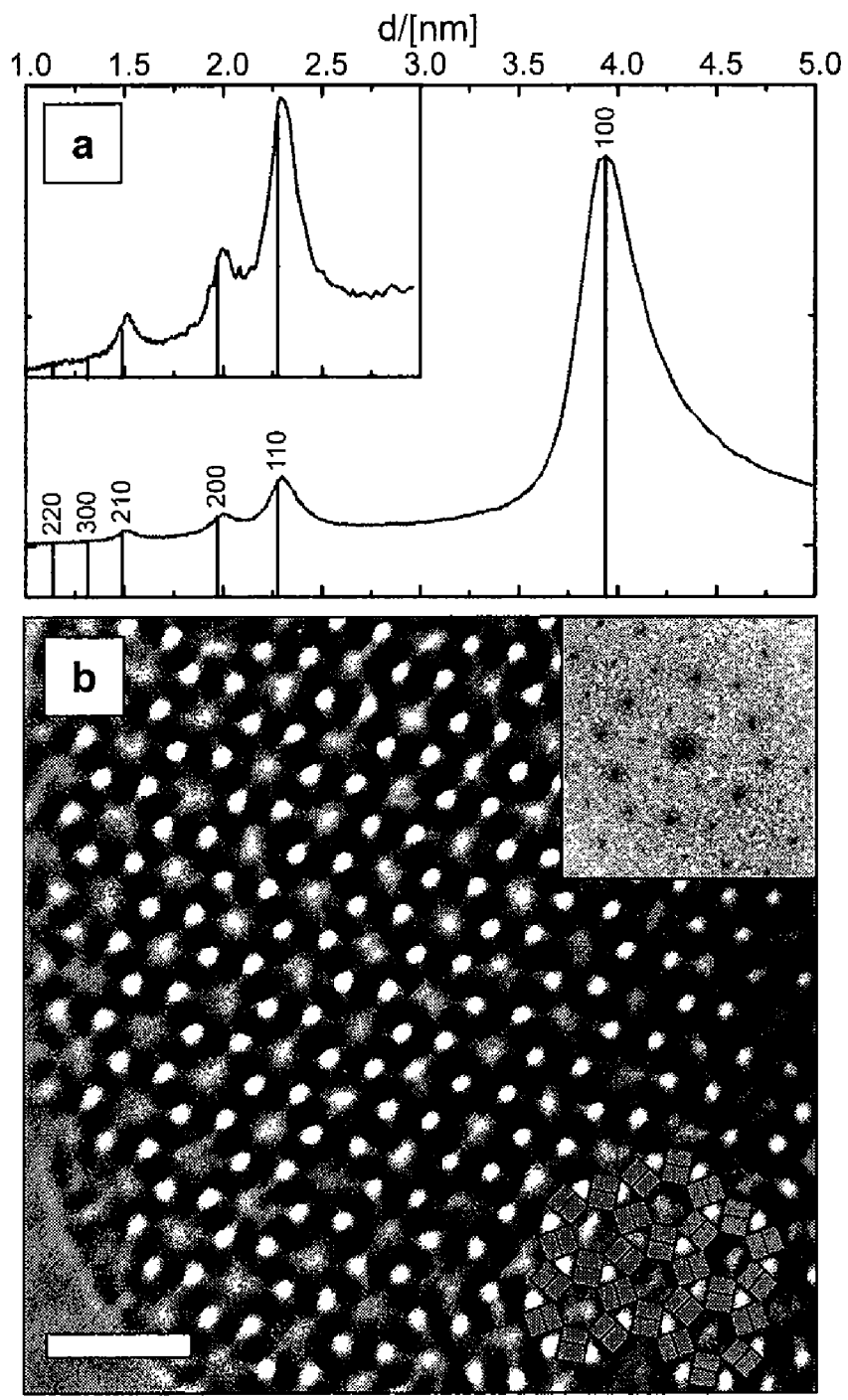
FIG. 1 shows in the upper part (a) the X-ray diffraction pattern, at interplanar spacings from 1.0 to 5.0 nm (with an enlarged insert for interplanar spacings from 1.0 to 3.0 nm) and in the lower part (b) a high resolution electron microscopy (hereinafter HREM) image (with a first insert for a scale bar representing 10 nm at bottom left, and a second insert for the Fourier transform at top right) of a mesoporous silica material according to an embodiment of the invention named Zeotile-1. The X-ray diffraction pattern is indexed according to the hexagonal tiling of nanoslabs (2.6×2.0×4.0 nm$^3$) as shown on the HREM image.

The term supersaturation of a compound, as used to disclose the present invention, refers to a solution that contains more of the dissolved compound than based on its solubility could be dissolved by the solvent under normal circumstances. Under prescribed experimental conditions of temperature and pressure, a solution can contain at saturation only one fixed amount of dissolved solute. A solution is at the saturation point when dissolved solute in it crystallizes from it at the same rate at which it dissolves. However if relatively stable solutions are achieved which contain a quantity of a dissolved solute greater than that of the saturation value provided solute phase is absent then such solutions are regarded as being supersaturated. Supersaturation can be expressed as drug concentration/crystalline equilibrium solubility.

The term "gemini" as used throughout this specification, in particular with respect to surfactants, refers to an organic molecule consisting of two preferably identical hydrocarbon molecules chemically bonded together by a spacer. The two terminal hydrocarbon tails can be short or long; the two polar head groups can be cationic or non-ionic; the spacer can be short or long. More detailed reference to such compounds may be found in B. S. Sekhon, *Resonance* (March 2004) pp. 42-45.

The term biologically active (bioactive) species, as used to disclose the present invention, means any kind of synthetic drug or molecule with bioactivity including therapeutic drugs, pesticides, insecticides, fungicides and the like, with a molecular weight preferably in the range of about 200 to about 1000. In the context of the present invention the biologically active species is preferably a poorly soluble therapeutic drug such as one classifiable as belonging to Class II or Class IV of the Biopharmaceutical Classification System and preferably has a water-solubility below about 2.5 mg/mL, even between 0.1 and 1 mg/mL (i.e. "very slightly soluble" as defined in the United States Pharmacopeia), even below 0.1 mg/mL (i.e. "practically insoluble" as defined in the United States Pharmacopeia), even below about 5 µg/mL and may even have a water-solubility as low as about 0.2 µg/mL, at room temperature and physiological pH. Non-limiting examples of such drugs include for instance chlorothiazide, hydrochlorothiazide, nimodipine, flufenamic acid, furosemide, mefenamic acid, bendroflumethiazide, benzthiazide, ethacrinic acid, nitrendipine, itraconazole, saperconazole, troglitazone, prazosin, atovaquone, danazol, glibenciamide, griseofulvin, ketoconazole, carbamazepine, sulfadiazine, florfenicol, acetohexamide, ajamaline, benzbromarone, benzyl benzoate, betamethasone, chloramphenicol, chlorpropamide, chlorthalidone, clofibrate, diazepam, dicumarol, digitoxin, ethotoin, glutethimide, hydrocortisone, hydroflumethiazide, hydroquinine, indomethacin, ibuprofen, ketoprofen, naproxen, khellin, nitrazepam, nitrofurantoin, novalgin, oxazepam, papaverine, phenylbutazone, phenyloin, prednisolone, prednisone, reserpine, spironolactone, sulfabenzamide, sultadimethoxine, sulfamerazine, sulfamethazine, sulfamethoxypyridazine, succinylsulfathiazole, sulfamethizole, sulfamethoxazole (also in admixture with trimethoprim), sulfaphenazole, sulfathiazole, sulfisoxazole, sulpiride, testosterone and diaminopyrimidines. Suitable examples of diaminopyrimidines include, without limitation, 2,4-diamino-5-(3, 4,5-trimethoxybenzyl)pyrimidine (known as trimethoprim), 2,4-diamino-5-(3,4-dimethoxybenzyl)-pyrimidine (known as diaveridine), 2,4 diamino-5-(3,4,6-trimethoxybenzyl)pyrimidine, 2,4-diamino-5-(2-methyl-4,5-dimethoxybenzyl)pyrimidine (known as ormetoprim), 2,4-diamino-5-(3,4-dimethoxy-5-bromobenzyl)pyrimidine, and 2,4-diamino-5-(4-chloro-phenyl)-6-ethylpyrimidine (known as pyrimethamine). The above-mentioned drugs are known as belonging to Class II (poorly soluble, highly permeable) or Class IV (poorly soluble, poorly permeable) of the Biopharmaceutical Classification System according to G. Amidon et al. in *Pharm. Res.* (1995) 12:413-420. As will be appreciated by those skilled in the art, these drugs belong to various therapeutic classes, including diuretics, anti-hypertensive agents, anti-viral agents, antibacterial agents, antifungals, etc, and are not limited to human or veterinary use alone.

Process for the Release of a Biologically Active Species

According to an embodiment of the process for the release of a biologically active species, according to the present invention, said ordered mesoporous oxide with said fixed or immobilized biologically active species is provided together with at least one supersaturation-stabilizing agent e.g., stabilizing polymers such as hydroxypropyl methyl cellulose (HPMC), polyacrylic acid, acrylic acid polymers, e.g., CARBOPOL® 974P carbomer, carboxypolymethylene polymers, e.g., CARBOPOL® 971P carbomer, and anti-precipitation tensides, particularly those having an HLB ratio>12, e.g., sodium lauryl sulphate, magnesium lauryl sulphate, ascorbylpalmitate and saccharose fatty acid esters such as saccharose monopalmitate and saccharose monostearate.

According another embodiment of the process for the release of a biologically active species, according to the present invention, said ordered mesoporous oxide based material has two or more levels of porosity and structural order.

According another embodiment of the process for the release of a biologically active species, according to the present invention, said two or more levels of porosity and structural order are obtained by assembly of nanometer size building units having zeolite framework, and wherein said assembly proceeds in the presence of one or more amphiphilic non-anionic surfactants, preferably wherein the internal structure of said nanometer size building units does not give rise to Bragg type diffraction in a powder X-ray diffraction pattern of said substantially crystalline mesoporous oxide based material.

According another embodiment of the process for the release of a biologically active species, according to the present invention, said fixing or immobilizing said biologically active species in said ordered mesoporous oxide is realized by an incipient wetness impregnation method.

According another embodiment of the process for the release of a biologically active species, according to the present invention, said fixing or immobilizing said biologically active species in said ordered mesoporous oxide is realized by melting said biologically active species in said ordered mesoporous oxide.

According another embodiment of the process for the release of a biologically active species, according to the present invention, said fixing or immobilizing said biologically active species in said ordered mesoporous oxide is realized by impregnating a solution of said biologically active species in non-polar solvent into said ordered mesoporous oxide and evaporating said non-polar solvent.

According another embodiment of the process for the release of a biologically active species, according to the present invention, the size of said biologically active species is suitable for entrapment into the mesopores of said ordered mesoporous oxide based material.

According another embodiment of the process for the release of a biologically active species, according to the present invention, the molecular weight of said biologically active species is between 200 and 1,000.

According another embodiment of the process for the release of a biologically active species, according to the present invention, the water solubility of said biologically active species is below 2.5 mg/mL, with between 0.1 and 1 mg/mL being preferred, below 0.1 mg/mL being particularly preferred and below 2.5 µg/mL being especially particularly preferred.

According another embodiment of the process for the release of a biologically active species, according to the present invention, said biologically active species is selected from the group consisting of acetohexamide, ajamaline, amiodarone, aripiprazole, atazanavir, atorvastatin, atovaquone, azithromycin, benazepril, bendroflumethiazide, benserazide, benzbromarone, benzthiazide, betamethasone, benzyl benzoate, bicalutamide, candesartan, carbamazepine, carisoprodol, carvedilol, celecoxib, chloramphenicol, chlorpromazine, chlorpropamide, chlorthalidone, chlorothiazide, clarithromycin, clofibrate, clopidrogel, clozapine, danazol, dapsone, diaminopyrimidines, diaveridine, diazepam, diclofenac, dicumarol, diflunisal, digitoxin, divalproex, docetaxel, efavirenz, ethacrinic acid, ethotoin, etodolac, ezetimibe, fenofibrate, florfenicol, flufenamic acid, furosemide, gemfibrozil, glibenclamide, glimepiride, glutethimide, glyburide, griseofulvin, hydrochlorothiazide, hydrocortisone, hydroflumethiazide, hydroquinine, hydroxyzine pamoate, ibuprofen, imatinib, indinavir sulphate, indomethacin, irbesartan, isotretinoin, itraconazole, ketoconazole, ketoprofen, khellin, lamotrigine, lansoprazole, linezolid, lopinavir, loratidine, lovastatin, meclizine, medroxyprogesteerone acetate, mefenamic acid, metaxalone, methylphenidate, mycophenolate, nabumetone, naproxen, nelfinavir mesylate, nevirapine, nifedipine, nimodipine, nitrazepam, nitrendipine, nitrofurantoin, novalgin, ofloxacin, olanzapine, olmesartan, orlistat, ormetoprim, oxazepam, papaverine, phenazopyridine, phenylbutazone, phenyloin, pioglitazone, prazosin, prednisolone, prednisone, pyrimethamine, quetiapine, raloxifene, reserpine, risperidone, ritonavir, rofecoxib, rosuvastatin, saperconazole, saquinavir, simvastatin, sirolimus, spironolactone, succinylsulfathiazole, sulfabenzamide, sulfadiazine, sulfadimethoxine, sulfamerazine, sulfamethazine, sulfamethizole, sulfamethoxazole, sulfamethoxy-pyridazine, sulfaphenazole, sulfathiazole, sulfisoxazole, sulpiride, tadalafil, tamoxifen, telmisartan, temazepam, temozolomide, terfenadine, testosterone, trimethoprim and troglitazone.

The anti-fungal triazole, itraconazole, has an estimated aqueous solubility of ca. 1 ng·mL$^{-1}$ at neutral pH and ca. 4 μg·mL$^{-1}$ at pH 1. Due to its high lattice energy and extremely hydrophobic character, itraconazole is a good model compound for low-solubility drugs in order to evaluate the ability of ordered mesoporous oxides materials to improve the dissolution properties. Compared with the commercial product Sporanox® and pure crystalline itraconazole not entrapped in said ordered mesoporous oxides the oral bioavailability is drastically increased as demonstrated by the plasma concentrations of itraconazole and OH-itraconazole as determined by HPLC-UV. After administration of crystalline itraconazole in dogs (20 mg), no systemic itraconazole could be detected by HPLC-UUV. Using ordered mesoporous oxides as a carrier, the AUC0-8 was boosted to 681 nM·h. In rabbits, the AUC0-24, increased significantly from 521 nM·h after oral administration of crystalline itraconazole (8 mg) to 1069 nM·h when this dose was loaded into ordered mesoporous oxides. $T_{max}$ decreased from 9.8 h to 4.2 h. No significant differences (AUC, $C_{max}$, $T_{max}$) could be determined when comparing ordered mesoporous oxides with itraconazole in both species. The oral bioavailability of itraconazole formulated with ordered mesoporous oxides as a carrier compares well with the commercial product Sporanox® (itraconazole), in rabbits as well as in dogs. The oral bioavailability of itraconazole formulated with ordered mesoporous oxides as a carrier compares well with the commercial product Sporanox®, in rabbits as well as in dogs. These results evidence that ordered mesoporous oxides is a promising carrier to achieve enhanced oral bioavailability for drugs with poor aqueous solubility.

In vitro results evidenced that the formulation strategy of the present invention was capable of creating a supersaturated state of itraconazole in FaSSIF (Fasted State Simulated Intestinal Fluid) when no preceding acidic dissolution was simulated. The extent of supersaturation exceeded 9.6 during at least four hours for the ordered mesoporous oxide as a carrier. As compared to saturation conditions (0.09 μg), supersaturation induced by the use of ordered mesoporous oxide increased transport across a Caco-2 cell monolayer more than 16-fold, resulting in the basolateral appearance of 1.46 μg itraconazole after 90 minutes, which demonstrates drastically increased tissue barrier penetration and permeation of the biologically active species and in particular of an enhanced transepithelial transport.

Since in the absence of an acid-neutral pH sequence, the performance of the commercial product Sporanox® was inferior with total transport amounting to 0.12 μg after 90 minutes. Enhanced absorption was confirmed in the in situ perfusion model where ordered mesoporous oxide was able to boost total transport of itraconazole after 60 minutes from 0.03 nmol·cm$^{-1}$ to 0.70 nmol·cm$^{-1}$ compared to saturated equilibrium conditions in FaSSIF. The solid dosage form Sporanox® again failed to achieve a similar extent of absorption enhancement (0.29 nmol·cm$^1$).

These findings demonstrate that intraluminal super-saturation can be realized by the use of ordered mesoporous oxide and that preceding dissolution of basic compounds in the acidic medium of the stomach is not required to allow for efficient intestinal absorption. Ordered mesoporous oxide is demonstrated to be a promising strategy for the delivery of especially basic low solubility compounds in patients suffering from hypochlorhydria; the pH-independency may also result in a more reproducible systemic exposure.

The present invention thus demonstrates that ordered mesoporous silica induces pH-independent supersaturation of a basic low solubility compound such as, but not limited to, itraconazole, which results in enhanced transport through tissue barriers in particular an enhanced transepithelial transport.

It has been demonstrated that ordered mesoporous oxide can be used as a carrier to create dosage form-induced super-saturation of weakly basic compounds such as the weakly basic model compound itraconazole ($PK_a$=3.7) in neutral biorelevant medium. It has been demonstrated that ordered mesoporous oxide can be used to obtain a pH-independent dissolution enhancement with a concomitant increase in intestinal absorption which increases reproducibility under highly varying conditions in the gastro-intestinal tract and thus provides more reliably drug dosage forms for humans or mammals in a medical treatment.

The present invention demonstrates that a supersaturated state of poorly soluble drugs such as itraconazole can be realized in a gastrointestinal fluid thereby improving the transepithelial transport and thus the oral bioavailability, by delivering such a drug entrapped in or loaded on ordered mesoporous oxide.

When a preceding acidic dissolution step was included to simulate the passage through the stomach, total transport across a Caco-2 cell monolayer was comparable for the ordered mesoporous oxide formulation and reference product Sporanox®. Since the majority of poorly water-soluble drugs are basic, this pH sequence is often a prerequisite to allow for sufficient oral bioavailability. Omitting this pH sequence, resulted in a reduced performance of Sporanox®, in the Caco-2 system as well as in the in situ perfusion model. This is attributed to the fact that Sporanox® is designed in such a way that preceding acidic conditions are needed to create intraluminal supersaturation. In contrast, the in vitro profiles generated by ordered mesoporous oxide illustrate the excellent capability of exceeding the thermodynamic equilibrium concentration of itraconazole in FaSSIF in the absence of a pH shift. As a consequence, transport through a Caco-2 cell monolayer and in an in situ system was increased drastically. Ordered mesoporous oxide is demonstrated to be an efficient strategy for the delivery of especially basic low solubility compounds in patients suffering from hypochlorhydria, the pH-independency resulting in better reproducibility in systemic exposure.

The present invention uses a stable composition to increase the bioavailability of itraconazole [a compound that has been associated with very poor formulation properties and a low aqueous solubility estimated to be ~1 ng/mL at neutral pH] when administered to a subject (e.g. a mammal or human being), whereby the composition in addition to one or more pharmaceutically acceptable fillers further comprises an ordered mesoporous oxides which incorporates a molecularly dispersed itraconazole, the ordered mesoporous oxide having mesopores with a pore size selected from a range between 3 and 20 nm, more preferably between 4 and 15 nm, yet more preferably between 5 and 12 nm and most preferably 6 to 10 nm or at least a mesopore size that is several times the molecular diameter of itraconazole, whereby the ordered mesoporous oxides incorporates 10 to 40% (w/w), preferably 15 to 35% (w/w), more preferably 20 to 30 (w/w) and most preferably 22 to 28% (w/w) of a molecularly dispersed itraconazole and whereby a pharmaceutical composition comprising the thus loaded ordered mesoporous oxide comprises a percentage in the range of 20 to 80%, preferably 30 to 60% and most preferably 40 to 50% of ordered mesoporous oxide with itraconazole of the weight of the composition. This composition is particularly useful in treatments of a subject to induce a local supersaturation of itraconazole at the place of delivery thereby enhancing the permeation of itraconazole through tissue barriers exposed to such supersaturated biologically active species and thereby enhancing the bioavailability of itraconazole. The tissue barrier can for instance be the gastrointestinal mucosa, the gastrointestinal epithelial cells, the nasal tissue or the skin.

In particular the composition of present invention is an oral immediate release composition of itraconazole loaded in an ordered mesoporous oxide which without comprising additional absorption enhancers can generate a condition of supersaturation of itraconazole and without the addition of solubility enhancers or solubility stabilizing agents realizes increased transepithelial transport of itraconazole and a condition of increased systemic bioavailability of itraconazole after oral delivery compared to a condition of oral delivery of the some dosage of itraconazole not being loaded in the ordered mesoporous oxides. Ordered mesoporous oxides suitable for such immediate release composition can be a silica oxide, germanium oxide or can be a metallic oxide of the group consisting of alumina, titania, zirconia, ceria, manganese oxide, niobium oxide, tantalum oxide, tungsten oxide, tin oxide, gallium oxide, iron oxide, and hafnium oxide or it can be a silica in combination with one or more other metallic oxides. The induced increase of transepithelial transport can be as drastic as more than 20 times. Moreover, the condition of increase of transepithelial transport can be realized in a patient or subject with reduced gastric acidity.

A specific embodiment of the process for the release of a biologically active species, according to the present invention, is a process to increase the oral bioavailability of itraconazole by delivering itraconazole entrapped or loaded into ordered mesoporous oxides perorally to a mammal.

Ordered Mesoporous Oxides with at Least One Level of Porosity

Examples of mesoporous oxides with a single level of porosity and structural order used (ordered mesoporous oxides) in the process for the release of a biologically active species, according to the present invention, are molecular sieves with very narrow pore size distribution because it is controlled by the precisely repeating crystalline nature of the materials, microstructure. The most important examples of molecular sieves are the zeolites.

Certain types of zeolitic materials such as porous crystalline aluminosilicates have a definite crystalline structure as determined by X-ray diffraction, within which there are a large number of smaller cavities, which may be interconnected by a number of still smaller channels or pores. These cavities and pores are uniform in size within a specific zeolite material. Since the dimensions of these pores are such as to accept for adsorption molecules of certain dimensions while rejecting those of larger dimensions, these materials are known as "molecular sieves" and are utilized in a variety of ways to take advantage of these properties.

The ordered mesoporous oxide used in the process, according to the present invention, preferably has a pore size in the range of 4 to 14 nm, with a range of 6 to 12 nm being particularly preferred.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are crosslinked by the sharing of oxygen atoms whereby the ratio of the total Group IIIB element, e.g. aluminum, and Group IVB element, e.g. silicon, atoms to oxygen atoms is 1:2.

Among solid substances known thus far, those having uniform channels, such as zeolites of porous crystalline aluminum silicate and of porous crystalline aluminum phosphates ($AlPO_4$) are defined as molecular sieves, because they selectively adsorb molecules smaller than the size of the channel entrance or they allow molecules to pass through the channel. In view of crystallography, zeolite and $AlPO_4$ are fully crystalline substances, in which atoms and channels are arranged in complete regularity. These fully crystalline molecular sieves are obtained naturally or synthesized through hydrothermal reactions. The number of fully crystalline molecular sieves obtained or synthesized thus far amount to several hundred species. A significant problem of the fully crystalline molecular sieve is that it cannot be used in reactions of molecules larger than about 1.3 nm in size.

A series of mesoporous molecular sieves, including MCM-41 and MCM-48, was reported in U.S. Pat. No. 5,057,296 and U.S. Pat. No. 5,102,643. These molecular sieves show a structure in which mesopores uniform in size are arranged regularly. MCM-41, has a uniform structure exhibiting hexagonal arrangement of straight mesopores, such as honeycomb, and has a specific surface area of about 1,000 $m^2/g$ as measured by ordinary BET.

Existing molecular sieves have been produced by using inorganic or organic cations as templates, whereas these mesoporous molecular sieves are synthesized through a liquid crystal template pathway by using surfactants as templates. These mesoporous molecular sieves have the advantage that their pore sizes can be adjusted in a range of 1.6 to 10 nm by controlling the kinds of surfactants or synthetic conditions employed during the production process.

Mesoporous molecular sieves have regularly arranged channels larger than those of existing zeolites. U.S. Pat. No. 6,592,764 discloses a family of high quality, hydrothermally stable and ultra large pore size mesoporous silica's by using amphiphilic block copolymers in acidic media. One member of the family, SBA-15, has a highly ordered, two-dimensional hexagonal (p6 mm) honeycomb, hexagonal cage or cubic cage mesostructure. Calcination at 500° C. yields porous structures with high BET surface areas of 690 to 1,040 $m^2/g$, and pore volumes up to 2.5 $cm^3/g$, ultra large d(100) spacings of 7.45 to 45 nm, pore sizes from 4.6 to 50 nm and silica wall thicknesses of 3.1 to 6.4 nm. SBA-15 can be readily prepared over a wide range of specific pore sizes and pore wall thicknesses at low temperature (35 to 80° C.) using a variety of commercially available, non-toxic and biodegradable amphiphilic block copolymers, including triblock polyoxyalkylenes.

U.S. Pat. No. 6,669,924 discloses a mesoporous zeolitic material having a stereoregular arrangement of uniformly-sized mesopores with diameters ranging from 2 to 50 nm and walls having a thickness of at least 4 nm and a microporous nanocrystalline structure, the mesopore walls having a stereoregular arrangement of uniformly-sized micropores with diameters less than 1.5 nm. It also discloses a method of preparing such a mesoporous zeolitic material, comprising the steps of:
a) providing a mesoporous silica having a stereoregular arrangement of uniformly-sized mesopores having diameters ranging from 2 to 50 nm and walls having a thickness of at least 4 nm and an amorphous structure;
b) impregnating said mesoporous silica with a zeolite-templating compound;
c) subjecting the impregnated mesoporous silica obtained in step (b) to a heat treatment at a temperature and for a period of time sufficient to cause transformation of said amorphous structure into a microporous nanocrystalline structure, thereby obtaining a mesoporous zeolitic material with mesopore walls having a stereoregular arrangement of uniformly-sized micropores with diameters less than 1.5 nm; and
d) removing said zeolite-templating compound from the mesoporous zeolitic material obtained in step (c).

Figure 5:
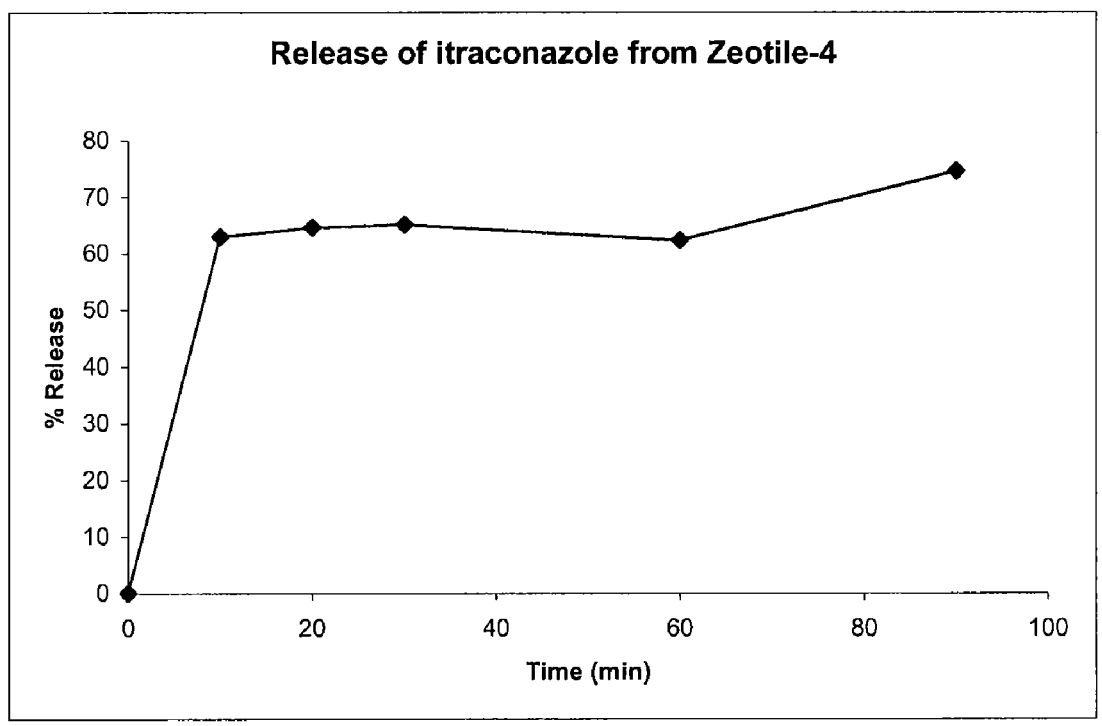
FIG. 5 shows the release of itraconazole in simulated gastric fluid from solid dispersions made up of 20% by weight of itraconazole and 80% by weight of a mesoporous silica material according to an embodiment of the invention named Zeotile-4.
Figure 9:
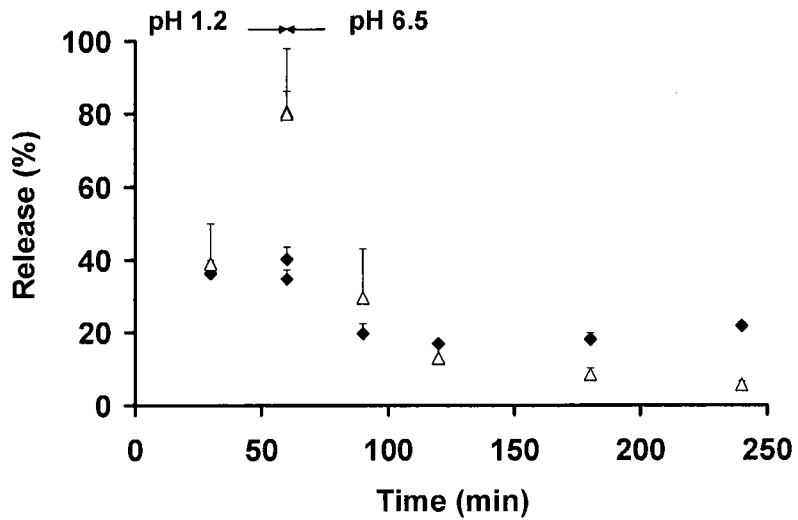
FIG. 9 shows the release profile of itraconazole from an ordered mesoporous silica of this invention (♦) and from Sporanox® (Δ) in SGF (pH 1.2) for 1 hour (100 µM) and subsequently in FaSSIF (pH 6.5) for 3 hours (10 µM).
Figure 14:
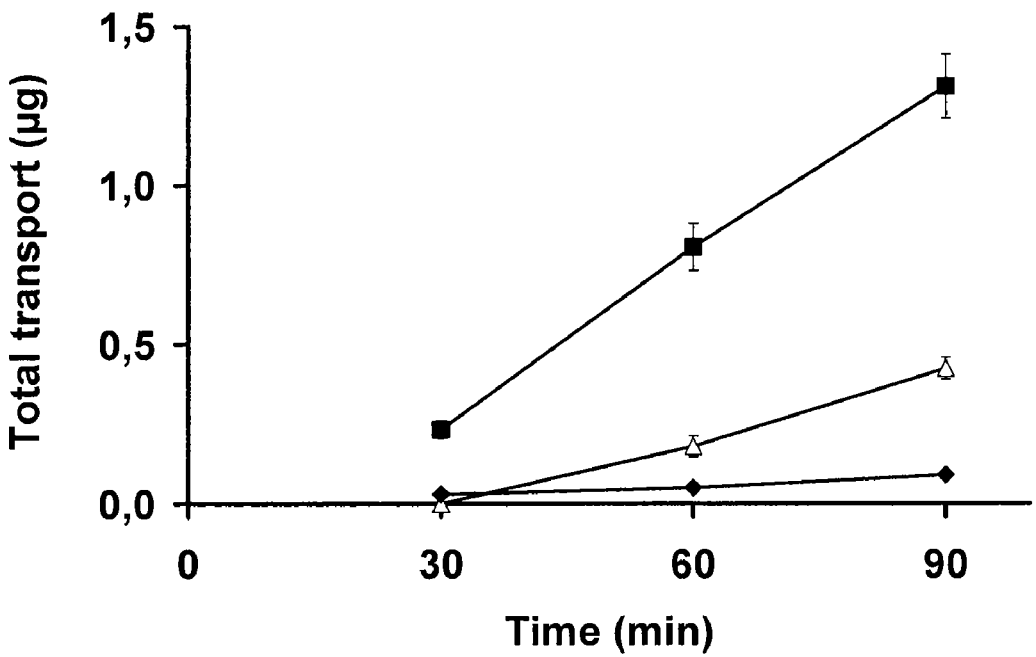
FIG. 14 shows the total transport (μg) of itraconazole over time across a Caco-2 cell monolayer starting from a saturated itraconazole solution (♦), an ordered mesoporous oxide suspension with a theoretical itraconazole concentration of 10 μM (Δ) and an ordered mesoporous oxide suspension with a theoretical itraconazole concentration of 75 μM in FaSSIF (■).
Figure 15:
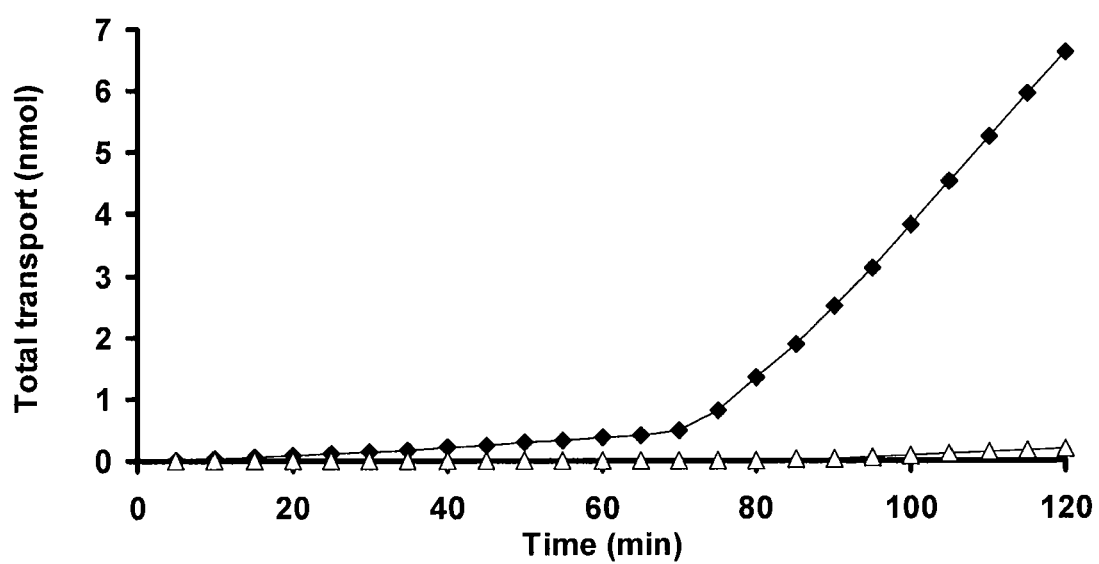
FIG. 15 shows the total transport over for an in situ perfusion using a saturated itraconazole solution in FaSSIF (first 60 minutes) and a supersaturated itraconazole solution (with a theoretical concentration of 75 μM). itraconazole (♦) and hydroxy-itraconazole (Δ) are presented.

The X-ray diffraction patterns of such material as shown in FIGS. 5, 9 and 15 of U.S. Pat. No. 6,669,924 clearly show the presence of several characteristic peaks at angles of diffraction above 3 degrees ($2\Theta=6°$). The pore distribution curves of FIG. 14 show that the more conversion is obtained in step (c), the more structural order is lost at the mesoporous level; in practice this means that reproducibility of the material may be impaired by an inaccurate control of the crystallization time. FIG. 15 also clearly shows that structural order obtained at the mesoporous level in step (a) is lost in steps (b) and (c) when zeolitic structure appears.

Silica molecular sieves with controlled porosity crystallize from hydrogel in the presence of organic template molecules. Patterned, mesoporous silica materials with amorphous walls may be obtained using structure directing surfactants or block copolymers.

The ordered mesoporous oxides exhibit a two-dimensionally ordered array of cylindrical pores of uniform size disposed parallel to each other and are separated by thin walls can be designed in a controllable manner the wide variety of chemical compositions, porosities for instance between 2 and 50 nm or more preferably between 4 and 20 nm and morphologies that can be achieved via sol-gel chemistry using shape selective polymers and surfactants. Tailoring the fine structure of these inorganic frameworks enables to construct devices, which are adapted to fulfill the needs of molecular guest species, in casu therapeutic molecules.

Mesoporous oxides with a single level of porosity and structural order used in the process for the release of a biologically active species, according to the present invention, may also be obtained by assembly of nanometer sized building units having zeolite framework and exclude mesoporous oxides obtained in the presence of an alpha-tocopherol polyethylene glycol ester templating biomolecule. These nanometer size building units are preferably generated by means of a mediating agent selected from the group consisting of tetraalkylammonium ions, tetraalkylphosphonium ions and gemini (dimeric) tetraalkyl-ammonium ions wherein each alkyl group independently has from 2 to 4 carbon atoms. More preferably, one or more of said alkyl groups is propyl. For example, said building units may be nanoslabs of substantially uniform size having a Silicalite-1 zeolite framework. The nanometer size building units present in the oxide based material of the invention may be referred to as nanoslabs [according to the terminology used by Kirschhock et al. in *J. Phys. Chem.* 103, 11021-11027 (1999)] of preferably substantially uniform size having a zeolite framework such as, but not limited to, the Silicalite-1 zeolite framework. Such nanoslabs may be generated by tetrapropyl-ammonium-ion mediation, for instance as disclosed by Kirschhock et al. in *Angew. Chem. Int. Ed.* 40, 2637-2640 (2001).

Nanometer size building units are preferably generated by means of a mediating agent selected from the group consisting of tetraalkylammonium ions, tetraalkylphosphonium ions and gemini (dimeric) tetraalkylammonium ions wherein each alkyl group independently has from 2 to 4 carbon atoms. More preferably, one or more of said alkyl groups is propyl.

Examples of ordered mesoporous oxides suitable for present invention include those with two-dimensionally ordered array of cylindrical pores of uniform size disposed parallel to each other and separated by thin walls.

MCM-41 typically has an average pore diameter that varies between 2 and 6 nm, whereas the average pore diameter varies between 4 and 13 nm for SBA-15. SBA-15 has in addition to the well defined mesopore system a complementary pore system comprised of micropores (pore size <2 nm). These micropores are located in the walls between adjacent mesopores and do not bridge the wall; they constitute dead end pores. These materials are suitable for present invention and are hereby incorporated by reference.

The appropriateness of a silica material for the fast drug release application can be evaluated based on the nitrogen adsorption isotherm at $-196°$ C. Appropriate silica materials exhibit type H1 hysteresis loops, following the classification of the International Union for Pure and Applied Chemistry (IUPAC) (Sing et al. in *Pure Appl. Chem.* 57(4), 603 (1985), which are characteristic of adsorbents with a narrow distribution of uniform, open ended tubular pores. Silica materials giving rise to hysteresis loops of type H2 or an ill-defined hysteresis loop should be considered as inappropriate for fast drug release.

The mesoporous materials ("zeotiles") used in the present invention are unexpectedly robust materials combining the advantages of micro- and mesoporous silicate structures. They are able to withstand temperatures up to about 400° C. for several hours in air.

Such ordered mesoporous materials and the processes to produce ordered mesoporous oxide materials by means of organic templates are available to the skilled man. Typical processes for preparing such ordered crystalline mesoporous silica oxide based materials with one or more levels of porosity and structural order or molecular sieves with precisely repeating crystalline microstructure and very narrow pore size distribution and an X-ray diffraction patterns which shows several characteristic peaks at angles of diffraction above 3 degrees ($2\Theta=6°$) are also available in the art.

Fast release of poorly soluble drugs can be achieved by loading the drug molecules on a silica carrier material with specific porosity and structural order. There exists an optimum pore diameter range of silica materials in order to achieve this fast release. The optimum pore size is in the range of about 4 to 14 nm, more preferably between 5 and 12 nm, most preferably from about 6 to 10 nm. Preferred are silica carriers with a mean pore diameter within this range, and having a narrow pore size distribution.

Those materials made by the surfactant-templated synthetic procedures can be extended to include a wide range of compositions and a variety of conditions based on the exploitation of electrostatic, hydrogen bonding and van der Waals interactions associated with amphiphilic molecules. Typically these materials are made under conditions where surfactant self-assembly occurs simultaneously with the condensation of the inorganic species, resulting in ordered mesoporous structures.

Surfactants as Structure Directing Agents and Template for Ordered Mesoporous Oxides:

The synthesis of inorganic mesoporous materials using ionic surfactant template molecules is widely reported in literature, and surfactant-mediated synthesis has since been used to form a variety of mesoporous materials. For instance, mesoporous molecular sieves such as the hexagonally ordered MCM-41 with hexagonal arranged straight mesopores being uniform in size were described by Beck et al. in J. Am. Chem. Soc. 114, 10834-10843 (1992).

Other ordered mesoporous silica's (denoted M41-S) are obtainable by inducing a cooperative self-assembly of a polymer precursor. Such synthesis, pore variation control, structures and properties characterization of M41-S and related mesoporous materials have been further detailed in literature.

Gemini Surfactants as Structure Directing Agents and Template for Ordered Mesoporous Oxides:

Gemini surfactants such as the dual chain dialkydimethylammonium salts can be used as a templating agent for the production of ordered mesoporous oxides. For instance for the Gemini surfactant with the generalized molecule formula $C_{16}H_{33}(CH_3)_2[CH_2]_nCH_3]N+$ for n (1,3,5,7) hexagonal MCM-41 can be produced.

The second phase, referred to as SBA-2, displays a three-dimensional hexagonal symmetry (P63/mmc) with supercages instead of unidimensional channels. The mesoporous supercage is analogous to a zeolite cage structure and this air calcination of silicate-based mesoporous molecular sieves with stable frameworks has been annotated as the SBA-n framework, but Stucky et al. in *Science* 268, 1324 (1995) used somewhat different Gemini surfactant as templates for a whole range of mesoporous structures: MCM-41 (2D hexagonal), MCM-48 (cubic); MCM-50 (lamellar), SBA-1 (cubic), SBA-2 (3D hexagonal) and SBA-3 (2D hexagonal). Their channels are regularly arranged, while the constituent atoms show an arrangement similar to that of amorphous silica.

J. S. Beck, et al. in J. Am. Chem. Soc. 114, 10834-10843 (1992) describes the preparation of a new family of mesoporous molecular sieves by the template action of the structure directing gemini surfactants such as the dual chain long chain alkylammonium surfactant molecules: MCM-41 (2D hexagonal), MCM-48 (cubic), MCM-50 (lamellar), SBA-1 (cubic), SBA-2 (3D hexagonal) and SBA-3 (2D hexagonal).

Inagaki described the synthesis of ordered mesoporous silica's annotated FSM-16 having large and uniform pores (2-50 nm) with high surface areas (~1,000 $m^2 g^{-1}$).

Polymer Templates: Amphiphilic Block Copolymers (ABCs) as Structure Directing Agents and Template for Ordered Mesoporous Oxides:

Hundreds of types of species of ordered mesoporous oxides (mostly unnamed) are obtained by the template action of structure directing amphiphilic block copolymers (ABCs) such as (poly(isoprene-b-ethyleneoxide block copolymer (PI-b-PEO), SE tensides (amphiphilic block copolymers consisting of an apolar polystyrene (S) block and a polar polyethylene oxide (E) block of an equal molecular weight) or poloxamers.

Amphiphilic block copolymers consist of at least one hydrophilic polymeric block and at least one hydrophobic polymeric block. The term amphiphilic refers to the double nature of those molecules consisting of at least two parts, one being soluble in a given solvent, and one which being insoluble.

When the solvent is water, one usually refers to the soluble part and to the insoluble part as the hydrophilic head and hydrophobic tail, respectively. The use of amphiphilic block copolymers to direct the organization of polymerization of silica or other metal oxides has been demonstrated to produce well-ordered hexagonal mesoporous silica or other metal oxides with pore sizes of 75 to 300 Å.

Certain amphiphilic block copolymers, or poloxamers also known by the trade name Pluronics, have been used for producing microporous/mesoporous silica's. Changing the MW of poly(ethylene oxide) (PEO) or poly (propylene oxide) (PPO) blocks in amphiphilic block polymers provides a control on the desired pore size in the end product of ordered mesoporous oxides. Such amphiphilic block copolymers have been further used for producing mesoporous ordered materials, in particular in a process for preparing structured organic-inorganic hybrid materials by the steps of (a) forming a mixture comprising at least one mesophase of an amphiphilic organic block copolymer consisting essentially of at least one hydrophilic block and at least one hydrophobic block as template and comprising at least one precursor which can be reacted to give an inorganic solid, (b) reacting the precursor in a bulk phase or in a mesophase that is free from solvent, and (c) optionally removing any volatile constituents from the reaction mixture, to produce the organic-inorganic hybrid material, wherein a hydrophobic block in the amphiphilic block copolymer has a glass transition temperature of 50° C. Further steps comprise removing the template and calcination and/or extraction whereby mesoporous solid are obtainable. Furthermore, Georges Attard et al. in "Mat. Res. Soc. Symp; Proc. Vol. 425 (1996) describes a lyothrophic liquid crystal phase process that allows the production of such crystalline mesoporous silica materials in a controllable manner predicting a priori the nanostructure of the solid by knowing the phase structure of the liquid before solidification and having the lyothropic liquid crystal phase acting as a template for the nanostructures.

Templin et al. in Science (1997) 278:1795-1798, reported that the amphiphilic block copolymers (poly(isoprene-b-ethyleneoxide block copolymer (PI-b-PEO) acted as structure-directing agents and by the use of this higher molecular weight block copolymer mesophases instead of low molecular weight surfactants they developed a simple production process to make in an easily controllable pathway various silica type mesostructured materials.

Dadabe et al. in *Journal of Sol-Gel Science* 4:107-116 (1995) demonstrates that amphiphilic molecules with their structured organization in liquid media present various advantages in the synthesis of silica inorganic networks such as synthesis of oxide nanoparticles with a very narrow size distribution.

S. A. Bagshaw et al in *Science* Vol 269 (1 Sep. 1995) provided a process for synthesizing mesoporous molecular sieves with amphiphilic block copolymers of ethylene oxide (PEO) and propylene oxide (PPO), more particular PEO-PPO block copolymers (PEO-propylene oxide (PPO) block co-polymers also known as poloxamers or by the trade name Pluronics) in which the PPO linkage acts as the hydrophobic segments to produce in a two steps process order mesoporous oxides. These were annotated MSU-X silica (or [Si]-MSU-X and the MSU-X alumina. The two step synthesis of the MSU type silica can apply useful to a wide range of surfactant or amphiphilic copolymers and give high yields with good reproducibility whatever the reaction volume and the intermediate formation of stable hybrid micelles provides a good control over the kinetics required to tune the final product for specific characteristics. These above described materials are useful for the present invention and are hereby incorporated by reference.

C. O. Göltner et al in Adv. Mater. 9(5), 431-436 (1997) demonstrated that amphiphilic block copolymers like their low-molecular weight surfactant analogues, can also form complex aggregates (lyothrophic liquid crystalline phases) for the generation of mesoporous inorganic nanostructures and allow a precise adjustment of the mutual compatibility between the created porous material and its template by simple methods of polymer synthesis and that such processes deliver products with thicker walls and are therefore more stable.

Weissenberger et al. in Ber. Bunsenges. Phys. Chem. 101 (11), 1679-1682 (1997) described processes to produce ordered mesoporous inorganic oxides with a regular structure, a pore size between 20 and 100 Å and a narrow pore size distribution, which have been annotated as polymer templated silica's (SE Silica's). Typical mesoporous silica's are for instance the materials SE10/10 silica and the SE30/30 silica depending on the template they were generated in. Lyotropic phases of amphiphilic block copolymers as polymer templates (e.g. amphiphilic block copolymers consisting of an apolar polystyrene (S) block and a polar polyethylene oxide (E) block of an equal molecular weight (the so called SE tensides) and water are also used as templates for this synthesis of mesoporous silica's.

S. Goss et al. describe in Ber. Bunsenges. Phys. Chem. 101(11), 1726-1730 (1997) another process for producing highly ordered mesoporous silica materials with templating lyothropic phases of non-ionic surfactants and amphiphilic block copolymers over various temperature ranges.

Examples of suitable ordered mesoporous oxides for entrapping biologically active species for the purpose of the process of the present invention are for instance the M41-S family of ordered mesoporous oxides; the MCM-X framework ordered mesoporous oxides; the MSU-X framework ordered mesoporous oxides e.g. MCM-41; the SE silica's ordered mesoporous oxides e.g. SE10/10-silica or SE30/30 silica, the SiO2-H1 & SiO2-SE ordered mesoporous oxides and the SBA-n framework ordered mesoporous oxides.

These above mentioned processes deliver ordered mesoporous oxides that are suitable for the purposes of the process of the present invention and are hereby incorporated by reference.

Ordered Mesoporous Oxides with at Least Two Levels of Porosity

The ordered mesoporous oxides with at least two levels of porosity and structural order, e.g. a silica material, in which the internal structure of said nanometer size building units do not give rise to Bragg type diffraction in a powder X-ray diffraction pattern used in the process for the release of a biologically active species, according to the present invention, may easily be produced in a two-step procedure. They have as first level building units nanoslabs of substantially uniform size having a zeolite framework (e.g. Silicalite-1) generated e.g. by the tetrapropylammonium template. At the second structural level, nanoslabs are linked through their corners, edges or faces following patterns imposed by interaction with amphiphilic non-anionic molecules for the assembly of nanometer size building units having zeolite framework, e.g. wherein said assembly proceeds while imparting a structural organization to said nanometer size building units. Within said the framework of such use, nanometer size building units may be linked through their corners, edges or faces following patterns imposed by interaction with said amphiphilic non-anionic molecule. Said one or more amphiphilic non-anionic surfactants are preferably selected from the group consisting of amphiphilic non-ionic molecules and amphiphilic cationic molecules or substances. For instance the amphiphilic non-anionic substance may be selected from the group consisting of amphiphilic block copolymers, cationic gemini (dimeric) surfactants and $C_{12-18}$ alkyltrimethyl-ammonium halide surfactants. Any halide may be suitable, preferably bromides and chlorides. When an amphiphilic cationic substance is used, e.g. a halide surfactant or a cationic gemini (dimeric) surfactant, it is important for the efficiency of production that the length of the hydrocarbon tail be from about 12 to 18 carbon atoms, preferably from 14 to 16 carbon atoms. Preferred surfactants are hexadecyltrimethylammonium chloride (HTACl), dodecyltri-methyl-ammonium bromide (DTABr), tetradecyltrimethyl ammonium bromide (TTABr) and octadecyltrimethylammonium bromide (OTABr). Under such circumstances, it is also important that interaction proceeds under basic conditions and, in a still more specific embodiment, interaction may proceed in the presence of one or more salts selected from the group consisting of aluminates, borates and acid salts of 3d transition metals on the periodic table. The preferred organic or inorganic salts, which are able to bind to monovalent cations, such as $Na^+$, $K^+$ and $NH_4^+$, and dissolve in water, are NaCl, KCl, $CH_3COONa$, NaBr, $Na_2SO_4$, $NaNO_3$, $NaClO_4$, $NaClO_3$, ethylenediaminetetracetic acid tetrasodium salt, adipic acid disodium salt, 1,3-benzenedisulfonic acid disodium salt or nitrilotriacetic acid sodium salt. Such water-soluble organic or inorganic salts capable of forming a bond with a monovalent cation are preferably used in amounts from about 1 to 15 moles salt per mole of the alkyltrimethylammonium halide.

When the one or more amphiphilic non-anionic substance is an amphiphilic block copolymer, it is preferred that interaction proceeds under acidic conditions. Suitable amphiphilic non-anionic substances are poly(ethylene oxide)-poly(alkylene oxide)-poly(ethylene oxide) triblock copolymers wherein the alkylene oxide moiety has at least 3 carbon at ordered mesoporous oxide, for instance a propylene oxide or butylene oxide moiety, more preferably such triblock copolymers wherein the number of ethylene oxide moieties in each block is at least 5 and/or wherein the number of alkylene oxide moieties in the central block is at least 30. An exemplary triblock copolymer is a Pluronic® P123 triblock copolymer $EO_{20} PO_{70} EO_{20}$ (wherein EO stands for ethylene oxide, and PO stands for propylene oxide).

Alternative suitable surfactants include any non-ionic surfactants with a hydrophilic-lipophilic balance (HLB) from 8 to 30 such as, but not limited to, reaction products of an alkylene oxide, typically ethylene oxide, with a fatty alcohol, a fatty acid, an alkylphenol (e.g. octylphenol or nonylphenol), an alkylamine or similar compounds having at least one active hydrogen atom. Preferably the carbon chain length of such compounds should be from 8 to 18 carbon atoms. Commercially available examples thereof are known under the trade names Mirj® 52, Mirj® 45 (polyoxyethylene stearate), Pluronic® 123 and the like.

The nanometer size building units to be assembled typically comprise one or more oxides selected from the group consisting of silica, germanium oxide and metallic oxides, all as previously described herein-above, and the said assembly results in forming a substantially crystalline mesoporous oxide based material preferably having characteristic features such as above stated (in particular with respect to their powder X-ray diffraction pattern).

The preparation process optionally further comprises the step of removing said tetrapropylammonium-ion and said cationic surfactant or triblock copolymer molecule, wherein said removal may be effected for instance through oxidation (e.g. by means of a strong acid such as nitric acid) and/or solvent leaching (e.g. using ethanol) and/or calcinations. Without being limited by theory it is believed that after evacuation of the organic molecules, microporosity is obtained inside the nanoslabs, and a precise mesoporosity between the nanoslabs depending on the tiling pattern of the zeolite slabs. Four different tiling patterns have been prepared and directly imaged by electron microscopy. X-ray diffraction confirms the mosaic structures derived from electron microscopy.

Such a material is easily distinguishable from other mesoporous materials known in the art, using analytical techniques well known to the skilled person. The absence of Bragg type diffraction from the internal structure of nanometer size building units manifests itself by the absence of peaks in a powder X-ray diffraction pattern at interplanar spacings below about 1.5 nm and/or at angles of diffraction Θ above about 3 degrees (2Θ above about 6 degrees). Preferably, said powder X-ray diffraction pattern should be performed after removal of said one or more amphiphilic non-anionic surfactants, in order to avoid any interfering peaks from such molecules. The absence of Bragg type diffraction from the internal structure of nanometer size building units in silica materials clearly manifests itself by the absence of peaks in a powder X-ray diffraction pattern at interplanar spacings below about 1.5 nm, as shown for instance in FIG. 1-a.

In the substantially crystalline mesoporous oxide based material according to the invention, said oxide based material may comprise one or more oxides selected from the group consisting of silica, germanium oxide and metallic oxides. A preferred non-metallic oxide is silica. The metallic oxides may derive from any metal selected from groups 4 to 12 of the periodic table. Preferred metals are aluminum and transition metals.

Exemplary metallic oxides are preferably selected from the group consisting of alumina, titania, zirconia, ceria, manganese oxide, niobium oxide, tantalum oxide, tungsten oxide, tin oxide, gallium oxide, iron oxide, and hafnium oxide. The mesoporous oxide based material according to the invention may comprise silica in combination with one or more such metallic oxides, which will be selected according to the intended end use of the material.

In the field of application envisaged and the most common industrial requirements, it is preferred that:
- the size of the building units in the material according to the invention ranges from about 1 to 8 nm, and/or
- the oxide based material has one or more types of mesopores each with an average size ranging from about 2 to 15 nm. The term "type of mesopore" as used herein refers to the geometrical shape which is not particularly limited and may be for instance hexagonal, cubic, lamellar and the like, and/or
- said one or more types of mesopores each have a narrow pore size distribution, i.e. a nearly uniform pore size distribution, as may be evidenced for instance from calculation by the Barrett-Joyner-Halenda (hereinafter referred as BJH) analysis from a nitrogen adsorption/desorption isotherm of said mesoporous oxide based material. BJH analysis is commonly used by the skilled person in this field of technology for performing an estimation of size distribution.

A preferred characteristic feature of the substantially crystalline mesoporous oxide based material of the invention is in having two or more levels of porosity comprising at least a microporosity and a mesoporosity, e.g. a microporosity inside said nanometer size building units and at least a mesoporosity between said nanometer size building units. For instance said building units may be assembled or arranged in a hexagonal pattern and may have a size ranging from about 1 to 8 nm. Another feature may consist of having mesopore walls with a thickness from about 1 to 4 nm.

In a crystalline mesoporous silica material with at least two levels of porosity, nanoslabs may for instance be forced into face-sharing double units with a size ranging from about 2 to 4 nm and linked in a hexagonal symmetry pattern. The crystalline mesoporous silica material according to the invention may be obtained from nanoslabs with a size ranging from about 1.3 to 8.0 nm, and/or from stapled nanoslabs arranged in a hexagonal appearing tile.

Biologically Active Species Belonging to Class II or Class IV of the Biopharmaceutical Classification System The biologically active species to be immobilized is a poorly soluble therapeutic drug belonging to Class II or Class IV of the Biopharmaceutical Classification System and preferably has a water-solubility below about 2.5 mg/mL, even between 0.1 and 1 mg/mL (i.e. "very slightly soluble" as defined in the United States Pharmacopeia), even below 0.1 mg/mL (i.e. "practically insoluble" as defined in the United States Pharmacopoeia), even below about 5 µg/mL and may even have a water-solubility as low as about 0.2 µg/mL, at room temperature and physiological pH.

In one embodiment of the invention, the biologically active species may be present in the fast release composition in an amount from about 0.5% to about 50% by weight, preferably from 2 to 40 weight %, more preferably from 5 to 30% by weight, of the composition. As will be easily understood by the skilled person, fast release is a feature which may significantly vary from drug to drug and from one drug loading to another.

Non-limiting examples of such drugs include for instance chlorothiazide, hydrochlorothiazide, nimodipine, flufenamic acid, furosemide, mefenamic acid, bendroflumethiazide, benz-thiazide, ethacrinic acid, nitrendipine, itraconazole, saper-conazole, troglitazone, prazosin, atovaquone, danazol, gliben-clamide, griseofulvin, ketoconazole, carbamazepine, sulfadi-azine, florfenicol, acetohexamide, ajamaline, benzbromarone, benzyl benzoate, betamethasone, chloramphenicol, chlorpropamide, chlorthalidone, clofibrate, diazepam, dicumarol, digitoxin, ethotoin, glutethimide, hydrocortisone, hydroflu-methiazide, hydroquinine, indomethacin, ibuprofen, ketoprofen, naproxen, khellin, nitrazepam, nitrofurantoin, novalgin, oxazepam, papaverine, phenylbutazone, phenyloin, prednisolone, prednisone, reserpine, spironolactone, sulfabenzamide, sulfa-dimethoxine, sulfamerazine, sulfamethazine, sulfamethoxypyridazine, succinylsulfathiazole, sulfamethizole, sulfamethoxazole (also in admixture with trimethoprim), sulfaphenazole, sulfathiazole, sulfisoxazole, sulpiride, testosterone and diaminopyrimidines. Suitable examples of diaminopyrimidines include, without limitation, 2,4-diamino-5-(3,4,5-trimethoxybenzyl)pyrimidine (known as trimethoprim), 2,4-diamino-5-(3,4-dimethoxybenzyl)pyrimidine (known as diaveridine), 2,4-diamino-5-(3,4,6-trimethoxybenzyl) pyrmidine, 2,4-diamino-5-(2-methyl-4,5-dimethoxybenzyl) pyrimidine (known as ormetoprim), 2,4-diamino-5-(3,4-dimethoxy-5-bromobenzyl)pyrimidine, and 2,4-diamino-5-(4-chloro-phenyl)-6-ethylpyrimidine (known as pyrimethamine). The above-mentioned drugs are known as belonging to Class II (poorly soluble, highly permeable) or Class IV (poorly soluble, poorly permeable) of the Biopharmaceutical Classification System according to G. Amidon et al. in *Pharm. Res.* (1995) 12:413-420. As will be appreciated by those skilled in the art, these drugs belong to various therapeutic classes, including diuretics, anti-hypertensive agents, anti-viral agents, antibacterial agents, antifungals, etc, and are not limited to human or veterinary use alone.

Preferably the size of said biologically active species should be suitable for entrapment into the mesopores of the ordered mesoporous oxide based material of this invention should in principle any kind of synthetic drug or molecule (including pesticides, insecticides, fungicides and the like), the invention is mainly useful in situations where the characteristics of the drug are such that formulation problems are difficult to solve due to poor water-solubility.

The biologically active species, preferably has a molecular weight between about 200 and 1,000.

The present invention is especially useful for the formulation of biologically active species having a polar surface area from about 60 Å$^2$ to 200 Å$^2$, for instance triazole compounds. The Polar Surface Area (PSA) is herein defined as the surface sum over all polar atoms (usually oxygen and nitrogen), including also attached hydrogens. PSA is a commonly used medicinal chemistry metric for the optimization of cell permeability. The present invention is especially useful for the formulation of biologically active species, for instance triazole compounds, having a polar surface area from about 70 Å$^2$ to 160 Å$^2$, preferably from about 80 Å$^2$ to 140 Å$^2$, more preferably from about 90 Å$^2$ to 120 Å$^2$, and most preferably from about 95 Å$^2$ to 110 Å$^2$.

The present invention is especially useful for the formulation of biologically active species having a partition coefficient from about 4 to 9, preferably from 5 to 8, and more preferably from 6 to 7, for instance triazole compounds. The partition coefficient (PC), a familiar term in the field of medicinal chemistry, is defined herein as the logarithm of the ratio of concentrations of said biologically active un-ionized compound in the two phases of a mixture of two immiscible solvents (octanol and water) at equilibrium, i.e. a measure of differential solubility of the compound between these two solvents. Hence the partition coefficient measures how hydrophilic or hydrophobic this chemical substance is. Partition coefficients are useful for example in estimating distribution of drugs within the body. Hydrophobic drugs with high partition coefficients are preferentially distributed to hydrophobic compartments such as lipid bilayers of cells while hydrophilic drugs (low partition coefficients) preferentially are found in hydrophilic compartments such as blood serum.

Fixation or Immobilization of the Biologically Active Species in the Ordered Mesoporous Oxide The biologically active species, e.g. itraconazole, can be fixed or immobilized (or loaded) into the ordered mesoporous oxide based material or, preferably, wherein said biologically active species is entrapped into the mesopores of the ordered mesoporous oxide-based material by different methods including, but not limited to, the solvent method, the incipient wetness impregnation method, and the melt method.

Characterization of the biopharmaceutical performance of ordered mesoporous silica material (ordered mesoporous oxide) as a carrier for the poorly water-soluble drug itraconazole demonstrated that the adsorption of itraconazole by loading into the ordered mesoporous oxides according to the process of the present invention led to a molecular dispersion of the biologically active species or drug.

Solvent Method:

In the "solvent method" a physical mixture of the biologically active species and the ordered mesoporous oxide based material in the desired drug loading weight ratio (e.g. up to about 30% drug by weight) is prepared and then added to an appropriate organic solvent, such as, but not limited to, dichloromethane or hexafluoroisopropanol.

A particular example of the solvent method is as follows: preparation of physical mixtures (100 mg) of a poorly water-soluble biologically active species such as itraconazole and an ordered mesoporous oxide with an itraconazole/mesoporous oxide weight ratio from about 30:70 to about 20:80 and addition to 6 mL of dichloromethane; then sonication for 1 minute; then agitation of the suspension for a further 24 hours; subsequent removal of the dichloromethane solvent by evaporation at about 35° C.; and when the resulting powder is dry shaking for 20 seconds and placing under reduced pressure (10$^{-3}$ bar) at about 40° C. for about 48 hours.

An appropriate organic solvent within the meaning of this embodiment of the invention is a solvent in which the poorly water-soluble biologically active species is soluble or has high solubility.

For instance an organic compound such as a fluorinated alcohol, for instance 1,1,1,3,3,3-hexafluoro-2-propanol (hereinafter referred as HFIP), exhibiting strong hydrogen bonding properties can be used to dissolve poorly water-soluble substances that serve as hydrogen-bond acceptors, such as amides and ethers. Biologically active species or drugs of the amide class of compounds contain carbonyl (C=O) and N—C dipoles arising from covalent bonding between electronegative oxygen and nitrogen atoms and electro-neutral carbon atoms, whereas the primary and secondary amides also contain two- and one N—H dipoles, respectively. The presence of a C=O dipole and, to a lesser extent a N—C dipole, allows amides to act as H-bond acceptors, which makes HFIP an appropriate solvent.

Another group of appropriate organic solvents are non-polar solvents such as, but not limited to, halogenated hydrocarbons (e.g. dichloromethane, chloroform, chloroethane, trichloroethane, carbon tetrachloride etc.), the most preferred being dichloromethane (DCM) or methylene chloride, which is an appropriate solvent for biologically active species or drugs such as diazepam, alpha-methyl-p-tyrosine, phencyclidine, quinolinic acid, simvastatin, lovastatin; paclitaxel, alkaloids, cannabinoids and the like.

Files and databases are available to the skilled person for common solvents and drug compounds (such as COSMOfiles (Trademark) from Cosmologic Gmbh & Co, GK) to select an appropriate solvent to load a poorly water-soluble biologically active species into an ordered mesoporous oxide. In addition, the skilled person can also make use of the teaching of Kolar et al. in *Fluid Phase Equilibria* 771-782 (2002) to select the appropriate organic solvent without undue burden.

For new biologically active structures not yet present in the above referred databases, drug solubility in any solvent can be calculated using thermodynamic criteria which contain basic physical properties and phase equilibrium relationships for instance by computational chemistry and fluid dynamics expert systems. Another opportunity is the automated drug solubility testers such as, but not limited to, Biomek® FX commercially available from Millipore Inc., to test without undue burden the water solubility of selected biologically active compounds.

After optional sonication of the physical mixture described above, the resulting suspension is agitated for a period of time ranging from about 30 seconds to about 24 hours before removing the solvent e.g. by evaporation at a suitable temperature (depending upon the selected solvent). When the resulting powder becomes dry, it can be shaken and then placed under reduced pressure (e.g. $10^{-3}$ bar) at about 40° C. for a longer period of time (e.g. 48 hours).

Incipient Wetness Method:

In the "incipient wetness impregnation method" high concentration solutions (e.g. up to 30 mg in 400 μL) of a biologically active species in an appropriate solvent such as, but not limited to, hydrogenated hydrocarbons (e.g. dichloro-methane) or fluorinated alcohols (e.g. hexafluoroisopropanol) are prepared and then added to the ordered mesoporous oxide-based material in an amount suitable for achieving the desired drug loading weight ratio (e.g. up to about 30% drug by weight). Other organic solvents in which a poorly water-soluble drug has high solubility are also appropriate for this method, using the solvent selection methods described above with respect to the first method. During the addition of the solution or the biologically active species or drug, the ordered mesoporous oxide powder is preferably intensively mixed, e.g. with a spatula or another mixing means depending upon the production scale. The resulting wet powders are then first dried in air under atmospheric pressure (e.g. at about 35° C. for a period of time ranging from about 15 minutes to 24 hours) and subsequently placed under reduced pressure (e.g. $10^{-3}$ bar) at about 40° C. for a longer period of time (e.g. 48 hours).

A particular example of such an incipient wetness impregnation method is for instance as follows: high concentration solutions of itraconazole in dichloromethane (e.g. from about 20 to about 30 mg in 400 μL) are prepared and added to respectively about 80-70 mg of an ordered mesoporous silica. During the addition of itraconazole solution, the powder is intensively mixed, e.g. with a spatula. In this way, drug loadings from about 20 to about 30 wt. % are obtainable. The resulting powders are first dried at about 35° C. in air for 24 hours and subsequently placed under reduced pressure ($10^{-3}$ bar) at about 40° C. for about 48 hours.

A particular impregnation method with a fluorinated alcohol (e.g. HFIP) comprises dissolving a poorly water-soluble biologically active species X (e.g. having amide and/or ether groups) in hexafluoroisopropanol and carrying out impregnation of the ordered mesoporous oxide material with such a solution according to the incipient wetness method. For instance X may be dissolved in HFIP in a concentration of about 50 mg/mL. The ordered mesoporous oxide material is weighed separately in a 10 mL test tube. Then, the compound X solution is added to the ordered mesoporous oxide material powder by 2 steps of 375 μL. After each addition, the powder may be homogenized e.g. with a spatula, and mixed till residual solvent was evaporated. After impregnation, the formulation is put in a vacuum oven at about 40° C. e.g. for at least 3 days. The drug-loading ratio may easily reach 20% (w/w) biologically active species/ordered mesoporous oxide material.

Melt Method:

In the "melt method" a physical mixture of a biologically active species and an ordered mesoporous oxide based material in the desired drug loading weight ratio (e.g. up to about 30% drug by weight) is prepared and heated at high temperature (e.g. 190° C.) for a relatively short period of time (e.g. 5 minutes). After this initial heating, the mixture may optionally be quickly shaken and heated again at a similarly high temperature for a similar period of time. After cooling, the resulting powders may then be stored, preferably under reduced pressure (e.g. $10^{-3}$ bar) at about 40° C., for a significant period of time (e.g. 48 hours).

A particular example of the "melt method" comprises for instance preparing a physical mixture of itraconazole and an ordered mesoporous silica with an itraconazole/ordered mesoporous oxide weight ratio from about 30:70 to about 20:80, and heating at 190° C. for 5 minutes. After this initial heating, the mixture is shaken quickly and placed back at 190° C. for 5 minutes. The powders are stored for 48 hours under reduced pressure ($10^{-3}$ bar) at 40° C.

Pharmaceutical Composition

The ordered mesoporous oxide with the fixed or immobilized biologically active species may be administered as such or comprised in a pharmaceutical or veterinary composition. This pharmaceutical composition may further comprise one or more pharmaceutically acceptable excipients (as is standard in the art), and are especially suitable for providing immediate or fast in vivo release of said biologically active species. Furthermore, it may comprise at least one supersaturation-stabilizing agent, e.g. CARBOPOL® 974P carbomer.

Whatever the production method used, solvent-based or solventless, when the pharmaceutical composition comprises one or more pharmaceutically acceptable excipients, the latter may be introduced at will either during the process step designed to entrap the biologically active species into the mesopores of the ordered and preferably crystalline ordered mesoporous oxide-based material, or afterwards in a separate step.

The fast release pharmaceutical compositions used in the present invention may further comprise one or more pharmaceutically acceptable fillers selected, for example, from hydrocolloids (such as xanthan gum), binding agents, glidants, lubricants, surfactants and diluents.

The term "pharmaceutically acceptable filler" as used herein is intended to refer to any material which is inert in the sense that it does not have any therapeutic and/or prophylactic effect per se but does not adversely interfere with the therapeutic or prophylactic property of the drug or biologically active species or pharmaceutical ingredient being formulated. The nature and amount of such fillers are not critical to the present invention. They include for instance binding agents such as starch, gelatin, glucose, alginic acid, sodium and calcium alginates, water-soluble acrylic (co)polymers, polyvinyl-pyrrolidone, polyaminoacids, ethylene-vinyl acetate copolymers and the like; natural and synthetic mineral fillers or glidants such as fumed (colloidal) silica (e.g. commercially available under the tradename Aerosil®), magnesium silicates such as talc, diatomaceous earth, aluminum silicate such as kaolinite, montmorillonite or mica, magnesium aluminum silicate such as attapulgite and vermiculite, carbon such as charcoal, sulphur and highly dispersed silicic acid polymers; water-soluble diluents such as lactose, sorbitol and the like.

Other excipients of the fast release pharmaceutical composition of this invention may suitably be selected from the group consisting of poly-ethyleneglycols and polypropyleneglycols having weight number molecular weights between about 300 and about 5,000; glycerol; propyleneglycol and glycerides (such as mono-, di- and triglycerides of polyethyleneglycol fatty acid esters, including those commercially available under the tradename Gelucire®). Suitable examples of the latter include those having both a portion derived from a glyceride and a portion derived from a polyethylene glycol ester. For instance, it is suitable to use polyglycosylated glycerides. The term "polyglycosylated glycerides" as used herein denotes a mixture of mono-, di- and triglycerides with polyethylene glycol (PEG) mono- and diesters of $C_8$-$C_{18}$ fatty acids with a molecular weight preferably between about 200 and about 600, optionally further including glycerol and/or free PEG, the hydrophilic-lipophilic balance (HLB) value of which is controlled by the chain length of the PEG and the melting point of which is controlled by the chain length of the fatty acids, of the PEG and of the degrees of saturation of the fatty chains, and thus of the starting oil. Similarly the expression "$C_8$-$C_{18}$ fatty acids" as used herein denotes mixtures in various proportions of caprylic acid, capric acid, lauric acid, myristic acid, palmitic acid and stearic acid, when these acids are saturated, and the corresponding unsaturated acids. As is well known to the skilled person, the proportions of these fatty acids may vary as a function of the starting oils. Examples of the latter include, but are not limited to, saturated polyglycolized $C_8$-$C_{10}$ glycerides, such as the PEG-8 caprylate/caprate glyceride esters sold by Gattefosse Corporation under the tradename Labrasol; PEG-6 caprylic/capric glycerides sold by Huls Aktiengesellschaft under the trade name Softigen® 767; PEG-60 corn glycerides sold by Croda under the trade name Crovol® M-70; Ceteareth-20 sold by Henkel Corporation under the trade name Emulgin® B2; diethyleneglycol monoethyl-ethers sold by Gattefosse Corporation under the trade name Transcutol®; a mixture of $C_8$-$C_{18}$ saturated polyglycosylated glycerides having a melting point within a range of about 42-48° C. and a HLB within a range of about 8 to 16 such as sold by Gattefosse Corporation under the trade names Gelucire® 48/09, Gelucire® 44/14 and Gelucire® 42/12; and mixtures thereof in various proportions. When a polyethyleneglycol is used for instance, it may comprise a higher molecular weight solid fraction and a lower molecular weight liquid fraction, the latter acting as a plasticizer.

The following examples illustrate the structural diversity of the ordered mesoporous oxide materials and their usefulness in drug delivery, in particular for fast release of poorly soluble drugs. From a structural point of view, other combinations are equally possible and may be produced while using the teachings of the present specification. At the first structural level, nanoslabs or building units with alternative framework types can be used, and heteroatoms can be incorporated. At the second structural level, the tiling pattern can be altered by changing the nature of the structure-providing agent and/or synthesis conditions such as concentration of nanoslabs, composition of nanoslabs, concentration of structure-providing agent, temperature and the like, without departing from the scope of the invention.

The following examples are provided solely for the purpose of illustrating various embodiments of the invention, and should not be construed as limiting its scope.

EXAMPLE 1

Nanoslabs were prepared through hydrolysis of tetraethyl ortho-silicate (37.32 g, commercially available from Acros, 98% purity) in 32.13 g of an aqueous tetrapropylammonium hydroxide solution (40% by weight concentration) under stirring. After hydrolysis, 30.55 g water was added and stirring continued for 24 hours. Nanoslab size (dimensions of 1.3×2.0×4.0 $nm^3$ in this embodiment) is controlled by synthesis conditions.

Then 60 g of a 10% by weight aqueous solution of cetyltrimethylammonium bromide (commercially available from Acros, 99% purity) heated at 80° C. was combined with 20 g of the nanoslab suspension under continuous stirring for 20 minutes. The precipitate was then recovered by filtration, washed with water and dried at 60° C. for 2 days. The organic templating organic molecules (tetrapropylammonium hydroxide and cetyltrimethyl-ammonium bromide) were removed by slurrying 3 g of the resulting solid in 200 mL ethanol containing 0.02 mole nitric acid at 77° C. for 1 hour. The solid was recovered by filtration and washed with ethanol. Oxidation with nitric acid was repeated twice. The sample was finally dried at 60° C. overnight.

Powder X-ray diffraction (XRD) and high-resolution electron microscopy (HREM), shown in FIG. 1, were used to characterize the obtained superstructures, i.e. the structural order of the material obtained.

As shown in FIG. 1-a, the XRD spectrum did not reveal internal nanoslab information but only information related to the tiling pattern of said nanoslabs, all characteristic peaks being located at interplanar spacings between 1.5 and 4.0 nm. Individual dispersed nanoslabs, presumably because of their small size, did not give rise to Bragg type diffraction related to their internal structure. In this material, slight misalignments in the tiling prevent the manifestation of this Bragg scattering.

In HREM, a low intensity electron beam and medium magnifications were used to minimize electron beam damage of the structure. The HREM image (FIG. 1-b) was taken in over focus conditions where the image directly represents the structure; the bright dots correspond to the projection of the channels. On this HREM image the schematic projected mosaic structure is superimposed. A first superstructure, herein referred to as Zeotile-1, is present in this sample. In Zeotile-1, nanoslabs are forced into face sharing, double nanoslab units, and measuring 2.6×2.0×4.0 $nm^3$ and linked in a hexagonal symmetry pattern. The Fourier transform of the HREM image (insert at top right of the figure) only shows information on the nanoslab tiling; no reflections related to the internal nanoslab structure were detected.

EXAMPLE 2

10 g of a Pluronic P123 triblock copolymer (commercially available from BASF, formula $EO_{20}$ $PO_{70}$ $EO_{20}$) was dissolved in 90 g water under stirring. 24 g of this solution was combined with 8 g of a 5 M HCl aqueous solution. 18 g of a nanoslab suspension prepared under similar conditions as in the first step of example 1 but with dimensions of 1.3×8.0×4.0 $nm^3$ (obtained through acidification of nanoslab suspension) was slowly combined with another 9 g 5M HCl solution under vigorous stirring and finally combined with the acidic triblock copolymer solution. The mixture was heated at 90° C. under quiescent conditions during 4 days. A solid product was formed and separated from the liquid by centrifugation at 12,000 rpm. The product was washed with water until pH exceeds 3. The sample was dried at 60° C., and finally calcined at 350° C. with a temperature with a temperature increase of 0.5° C./minute.

Figure 3:
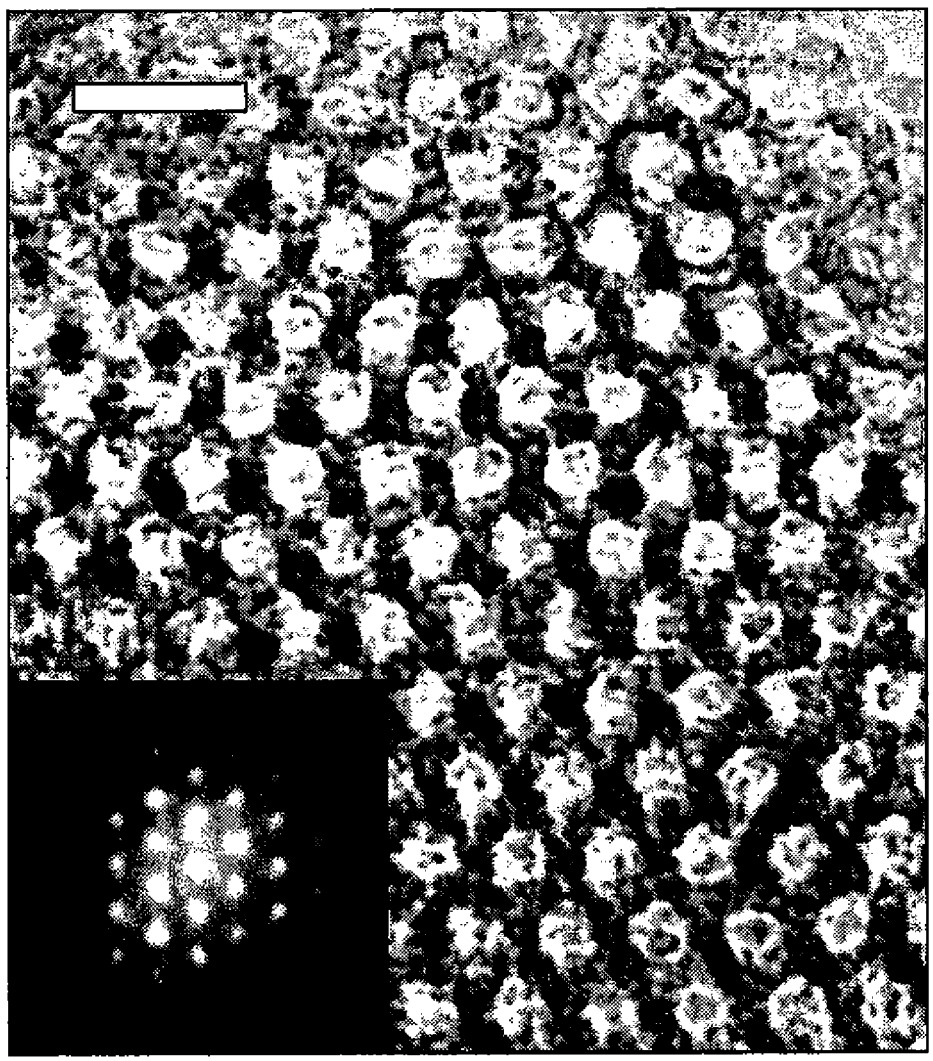
FIG. 3 shows a HREM image, together with electron diffraction pattern insert (insert for the Fourier transform at bottom left) of a mesoporous silica material according to another embodiment of the invention named Zeotile-4 (scale bar represents 20 nm).

High-resolution electron microscopy (HREM) was used to characterize the structural order of the material obtained, herein named as Zeotile-4. As shown in FIG. 3, Zeotile-4 is made up from stapled large nanoslabs arranged in a hexagonal appearing tile, the large nanoslabs used as building units being clearly visible in the image. In HREM, the tiling patterns show a high perfection throughout the individual Zeotile particles reaching micrometer sizes. The Fourier transform of the HREM image (insert at bottom left of the figure) only shows information on the nanoslab tiling; no reflections related to the internal nanoslab structure were detected.

The integrity of the Silicalite-1 building blocks in this material was also confirmed with $^{29}Si$ MAS NMR (nuclear magnetic resonance), showing the unique silicon connectivity of the nanoslabs to be maintained during the tiling process and templating organic species evacuation. In addition, nitrogen adsorption isotherms at −196° C. and alkane separation experiments confirmed the presence of Silicalite-1 microporosity next to mesopores with precise diameters (9.4 nm for example 2).

EXAMPLE 3

6 g of cetyltrimethylammonium bromide (commercially available from Acros, 99% purity) in powder was slowly added to 20 g of the nanoslab suspension prepared according to example 1 under vigorous stirring, followed by addition of 60 g water. The slurry was stirred for 24 hours and subsequently heated at 100° C. for 72 hours under quiescent conditions. The resulting precipitate was then treated by the same method as in example 1.

Figure 2:
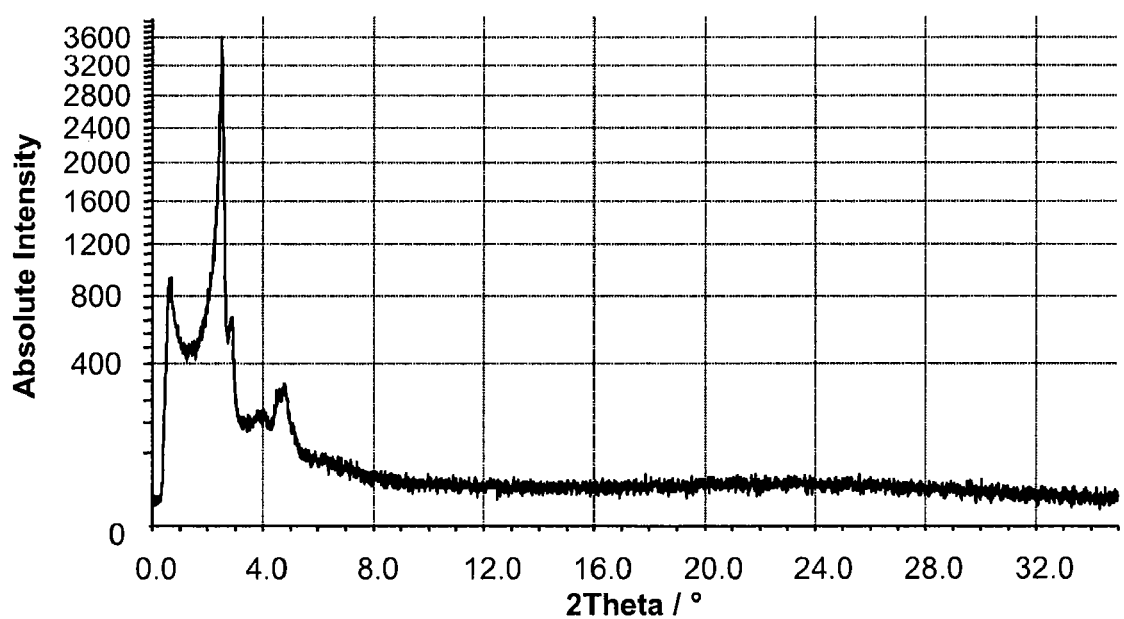
FIG. 2 shows the X-ray diffraction pattern, at diffraction angles Θ from 0 to 16 degrees (2Θ from 0 to 32 degrees) of a mesoporous silica material according to another embodiment of the invention named Zeotile-2.

Powder X-ray diffraction (XRD), shown in FIG. 2, and high-resolution electron microscopy (HREM) were used to characterize the structural order of the material obtained, named Zeotile 2. As shown in FIG. 2, the XRD spectrum did not reveal internal nanoslab information but only information related to the tiling pattern of said nanoslabs, all characteristic peaks being located at angles Θ below 3 degrees (2Θ below 6 degrees). Individual dispersed nanoslabs, presumably because of their small size, did not give rise to Bragg type diffraction related to their internal structure.

Electron diffraction (ED) and HREM images demonstrated that Zeotile-2 is built from very similar units as Zeotile-1 (example 1), but has body centered cubic symmetry.

EXAMPLE 4

The release of itraconazole (purity above 99%) from Janssen Pharmaceutical (Beerse, Belgium) was investigated with solid dispersions from various zeolitic materials. After complete dissolution of itraconazole in methylene chloride, SBA-15 (a material made in accordance with U.S. Pat. No. 6,592,764) or MCM-41 (a commercially available zeolite) were suspended and the mixture was stirred for 20 hours. Subsequently, the solvent is removed by rotary evaporation or spray-drying and the powder was further dried for 48 hours at 40° C. under reduced pressure. In this way solid dispersions having a drug loading of 20% by weight were prepared. In order to study the release of the drug substance, the solid dispersions were suspended in simulated gastric fluid (defined according to U.S. Pharmacopoeia XXV) at 37° C. under stirring. At specific time intervals, the concentration of the drug substance in the dissolution medium was measured using high performance liquid chromatography (HPLC). All experiments were performed in triplicate.

Concentrations of itraconazole were determined using an isocratic HPLC method. The HPLC system consisted of a Lachrom® L-7100 HPLC pump, an autosampler model L-7200 equipped with a 100 µL loop, a UV detector model L-7420 set at 257 nm, and an Interface D-7000, all from Merck (Darmstadt, Germany). UV signals were monitored and peaks were integrated using the D-7000 HSM software. All chromatographic separations were performed at room temperature. The 12.5×0.4 cm column was packed with LiChrospher® 100 RP-18 (5 µm) (also from Merck, Darmstadt, Germany). The mobile phase consisting of acetonitrile/tetrabutylammonium hydrogen sulfate 0.01N (55:45 volume/volume), was filtered through a membrane filter (0.45 µm) and degassed by ultrasonication before use. The flow rate amounted to 1 mL/minute.

Figure 4:
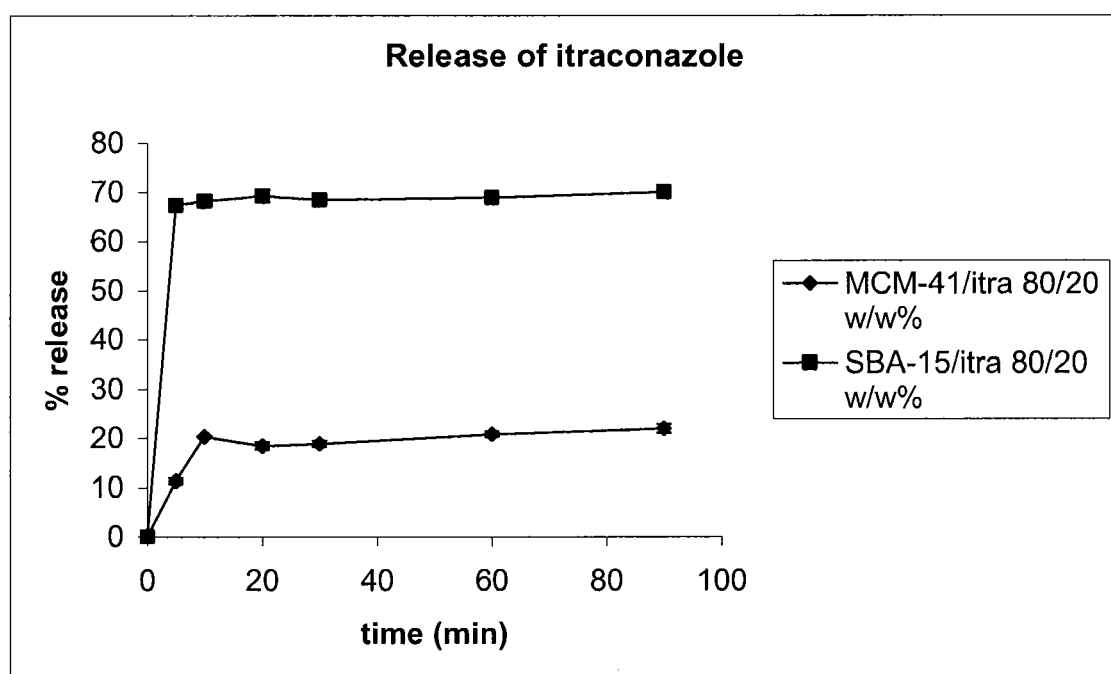
FIG. 4 shows the release of itraconazole in simulated gastric fluid from solid dispersions made up of 20% by weight of itraconazole and 80% by weight of a mesoporous silica material known under the reference SBA-15 (upper curve) or a zeolite known as MCM-41 (lower curve).

FIG. 4 shows the dissolution of itraconazole in simulated gastric fluid from solid dispersions made up of 20% of drug and 80% of either SBA-15 or MCM-41. In the case of SBA-15, the rate of release (about 68% after 10 minutes) as well as the maximal amount of drug dissolved is significantly higher than in the case of MCM-41.

EXAMPLE 5

The procedure of example 4 was repeated, except that the zeolitic material used was that of example 3, i.e. Zeotile-4. FIG. 5 shows the dissolution of itraconazole in simulated gastric fluid from solid dispersions made up of 20% of drug and 80% of Zeotile-4. From a steady comparison with FIG. 4, it is clear that the rate or release in the case of Zeotile-4 (about 63% release after 10 minutes) is significantly higher than in the case of MCM-41 (about 20% after 10 minutes).

EXAMPLE 6

Figure 6:
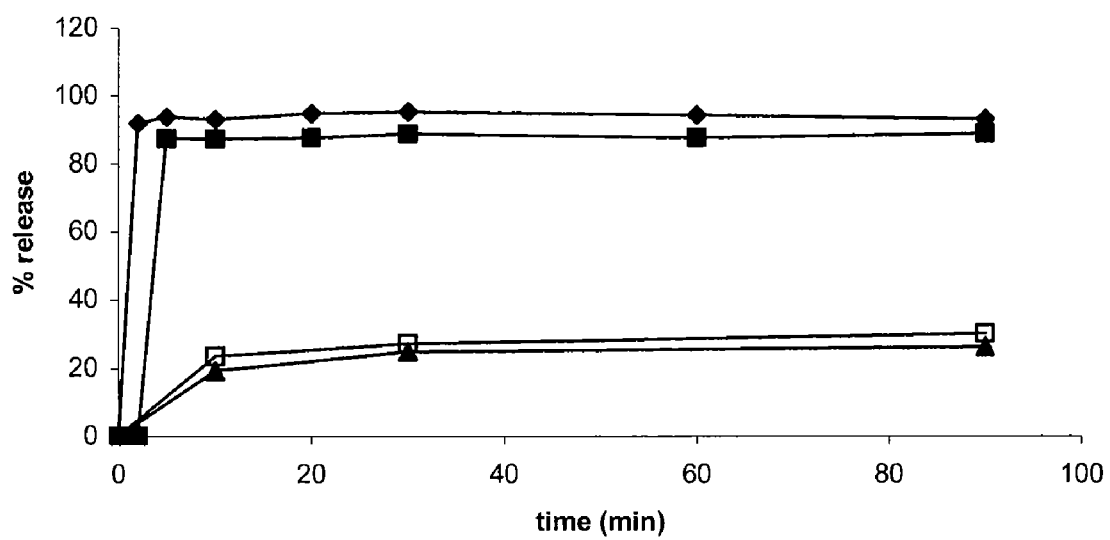
FIG. 6 shows the release of diazepam from solid dispersions made up of 30% by weight of diazepam and 70% by weight of a mesoporous silica material according to an embodiment of the invention named Zeotile-4.

The procedure of example 5 was repeated, except that the drug used was diazepam. FIG. 6 shows the dissolution of diazepam in simulated gastric fluid from the following solid dispersions:
30% drug loading and 4% Mirj (♦);
30% drug loading (■);
physical mixture containing 30% drug (not treated) (▲);
physical mixture containing 30% drug (treated) (□)

EXAMPLE 7

Production of an Ordered Mesoporous Silica

An ordered mesoporous silica was prepared as follows. Briefly, 6 g of a triblock copolymer Pluronic® P123 (commercially available from BTC-Benelux, La Hulpe, Belgium) was dissolved in 180 g of 2M HCl. This mixture was placed in an oil bath at 35° C. under magnetic stirring. An amount of 15.3 g of sodium silicate solution (containing >27 wt.-% SiO$_2$, commercially available from Riedel-de Haën, Seelze, Germany) was diluted with 45 g dematerialized water. This mixture was added drop wise to the Pluronic P123 solution under vigorous stirring. Stirring was allowed to continue for another 5 minutes before switching to static synthesis conditions at 35° C. After 24 hours, the silica suspension was transferred into a Teflon-lined autoclave and placed in an oven for hydrothermal treatment at a temperature of 90° C. for another 48 hours. Finally, the powder was washed on a 0.45 µm filter (commercially available from Whatman Schleicher and Schuell, Dassel, Germany) with dematerialized water, dried and calcined at 550° C. for 8 hours under ambient atmosphere to remove the triblock copolymer from the pores.

EXAMPLE 8

Loading of an Ordered Mesoporous Silica with Itraconazole

Loading of the ordered mesoporous silica of example 7 was performed by suspending it into an itraconazole (commercially available from Bosche Scientific, AK Scientific, AvaChem Scientific, DSM Pharma Fine Chemicals or Sigma) solution in methylene chloride (5 mg/mL). The mixture was agitated for 24 hours using a rotary mixer (operated at 20 rpm, commercially available from Snijders, Tilburg, The Netherlands). The initial ordered mesoporous oxide and itraconazole weight proportions amounted to 75 wt. % and 25 wt. %, respectively. Subsequently, the solvent was removed by evaporation and the powder was dried overnight at 35° C. Ordered mesoporous oxide loaded with itraconazole was heated to 100° C. for 5 minutes and placed under reduced pressure ($10^{-3}$ bar) at 40° C. for another 48 hours. Itraconazole loading was determined using a long-term release experiment during seven days under sink conditions [0.1M HCl, 0.5 wt. % SLS (Certa S. A., Braine-l'Alleud, Belgium), n=5].

EXAMPLE 9

Solubility and In Vitro Dissolution of Itraconazole by Solvent Induced Supersaturation Media The FaSSIF (Fasted State Simulated Intestinal Fluid) medium used for dissolution experiments was prepared based on blank FaSSIF which is a phosphate buffer obtained by dissolving 0.696 g NaOH (commercially available from BDH Laboratory Supplies, Poole, England), 7.91 g $NaH_2PO_4.H_2O$ (commercially available from Merck, Darmstadt, Germany) and 12.37 g NaCl in 2 L of purified water (18.2 MΩ, Elga, Tex., USA). The pH was adjusted to 6.5 with 1M NaOH. FaSSIF was created by adding 3.23 g sodium taurocholate (commercially available from ICN Biomedicals, Eschwege, Germany) and 5.90 mL of a solution of lecithin (commercially available from YDS Chemicals, Heusden, Belgium) in chloroform (100 mg/mL) to approximately 200 mL blank FaSSIF. This mixture was heated to 80° C. for 15 minutes to remove chloroform, after which a clear solution was obtained. Subsequently, blank FaSSIF was added up to a volume of 1 L. Some experiments were performed with MES buffered FaSSIF to allow for the addition of SGF (simulated gastric fluid, 0.1 M HCl containing 0.2 wt. % NaCl) without a significant pH change. MES [2-(N-morpholino)ethanesulfonic acid, commercially available from Sigma-Aldrich, Steinheim, Germany] (977.3 mg), sodium taurocholate (179.1 mg) and lecithin solution (655.6 µL) were added to prepare 100 mL of MES-FaSSIF according to the same protocol.

Determining Solubility:

The solubility of itraconazole in FaSSIF was determined by weighing approximately 2 mg into an Eppendorf tube (1.5 mL) and adding 1 mL of freshly prepared FaSSIF. The tubes were shaken at 37° C. (Incubator-Shaker Series 25D, commercially available from New Brunswick Scientific Co., United States of America) with a speed of 130 rpm to ensure the formation of a homogeneous suspension. After specific time intervals, the solid material was removed from the medium by centrifugation at 37° C. and 14,000 rpm for 10 minutes (Eppendorf 5804 R, Germany) (n=6 per time point). The supernatant (400 µL) was diluted with mobile phase (1:1) and kept at 4° C. prior to analysis.

Solvent Induced Supersaturation:

Solvent induced supersaturation was obtained by spiking FaSSIF with a concentrated solution of itraconazole (5 mM) in DMSO (commercially available from Acros Organics, Geel, Belgium). In this way, concentrations intended to range from 20 µM up to 75 µM were prepared. Due to precipitation, the real concentration cannot be predicted in advance. We therefore prefer to denote each sample with its theoretical concentration intended initially. The final DMSO fraction in FaSSIF never exceeded 2% by volume. Itraconazole supersaturation in FaSSIF was also generated based on a pH shift starting from a 100 µM itraconazole solution in SGF. After one hour, 9 mL MES-FaSSIF was added to 1 ml of the above-mentioned solution. For both methods, supersaturation was characterized by determining the itraconazole concentration at specific time intervals. Samples were centrifuged at 14,000 rpm for 15 minutes to remove precipitated itraconazole. Supernatants were collected and immediately diluted with mobile phase (1:1) to prevent precipitation during storage and analysis.

Ordered Mesoporous Silica Induced Supersaturation:

In order to study the formulation-induced supersaturation of itraconazole in biorelevant conditions, ordered mesoporous silica loaded with itraconazole was suspended in FaSSIF. The dissolution study was performed in test tubes of 8 mL under gentle agitation using a rotary mixer (commercially available from Snijders, Tilburg, Netherlands). The amount of material in the dissolution medium was adjusted to eventually obtain a theoretical concentration of the drug substance (75 µM). In the same way as with the solvent induced supersaturation, the effect of prior acidic dissolution was evaluated by suspending the dosage form into 1 mL SGF. After 1 hour, the medium was converted into FaSSIF with the addition of 9 mL MES-FaSSIF. At specific time intervals, samples were collected and the medium was filtered through a 0.45 µm PTFE membrane. Prior to analysis by HPLC, samples were diluted with methanol (1:1) to prevent precipitation during storage and analysis.

Analytical:

Samples of the in vitro dissolution study were assayed using an isocratic HPLC method. The HPLC system consisted of a LaChrom® L-7100 HPLC pump, an autosampler model L-7200 equipped with a 100 µl loop, a UV detector model L-7420 set at 260 nm, and an Interface D-7000 (all commercially available from Merck, Darmstadt, Germany). UV signals were monitored and peaks were integrated using the D-7000 HSM software. The separation of itraconazole was performed on a RP-18 150×4.6 mm 5 µm Hypersil silica column (commercially available from Thermo Electron Corporation, Waltham, United States of America) at room temperature. The mobile phase consisted of acetonitrile:tetrabutyl ammonium hydrogen sulfate 0.01 N (55:45 by volume), and was filtered through a 0.45 µm PTFE membrane and degassed by ultrasonication before use. The flow rate amounted to 1.5 mL/min. The standard curves were linear over the concentration range of 0.0001 to 3 mg/mL.

In order to study the nature of the precipitate formed during formulation induced supersaturation experiments, modulated temperature differential scanning calorimetry (hereinafter referred as MTDSC) measurements were carried out using a Q1000 MTDSC device (commercially available from TA Instruments, Leatherhead, United Kingdom) equipped with a refrigerated cooling system. The heat capacity signal was calibrated by comparing the response of a sapphire disk with the equivalent literature value at 80° C. The amplitude used in the MTDSC experiment was 0.212° C., the period was 40 seconds, and the underlying heating rate was 2° C./minute. The samples were heated from 0° to 200° C. DSC analysis of the precipitate formed during solvent induced supersaturation was carried out on a DSC 2920 apparatus (commercially available from TA Instruments, Leatherhead, United Kingdom). The sample was heated from 20° C. to 200° C. at the rate of 2° C./min. The temperature scale and the enthalpic response were calibrated with an indium standard and aluminum open pans (commercially available from TA Instruments, Leatherhead, United Kingdom) were used for all calorimetric studies.

Figure 7:
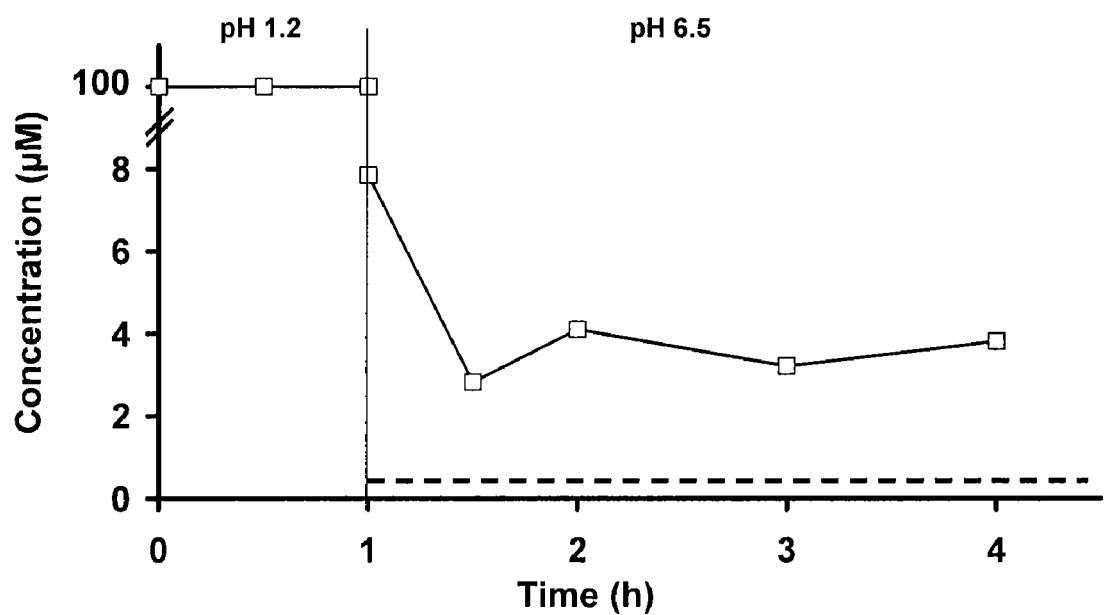
FIG. 7 shows the concentration-time profile of itraconazole in SGF (pH 1.2) for 1 hour (100 µM) and subsequently in FaSSIF (pH 6.5) for 3 hours (10 µM). The equilibrium solubility of crystalline itraconazole in FaSSIF is presented as a dotted line.

In Vivo Gastrointestinal pH Shift Condition:

Intraluminal supersaturation may occur when a poorly water-soluble basic compound is first dissolved in the acidic environment of the stomach and subsequently released into the small intestine. This transition was simulated starting from a SGF solution of itraconazole (100 µM): after an initial residence of one hour at pH 1.2, the medium was converted into FaSSIF and itraconazole concentrations were determined to study the ability to create intraluminal supersaturation. Because this pH shift was accompanied with a 10-fold dilution, the maximum theoretical concentration in FaSSIF amounted to 10 µM. The resulting concentration-time profile is depicted in FIG. 7. After the pH shift to 6.5, the itraconazole concentration immediately dropped to 7.85 µM; after 30 minutes, the concentration amounted to 2.82 µM. This decrease can be attributed to the partial precipitation of itraconazole. Following the initial drop, the concentration increased again to achieve approximately 4 µM for the next 3 hours. Despite precipitation, itraconazole concentrations readily exceed the thermodynamic solubility of itraconazole in FaSSIF. The equilibrium solubility value was determined during an equilibration period for up to one week and amounted to 0.40 µM (presented as a dotted horizontal line in FIG. 7). The extent of supersaturation can be expressed as the actual concentration of itraconazole over its equilibrium solubility (c/s). Here, the minimal extent of supersaturation amounted to 7.1 and was observed 30 minutes after the pH shift. The fact that, in FaSSIF (pH 6.5), a supersaturated state of itraconazole was maintained during at least 3 hours is predictive of a mechanism, which inhibits nucleation and crystal growth. The intestinal medium FaSSIF indeed contains two surface active compounds, lecithin and sodium taurocholate which can solubilise materials through micellar encapsulation but can also alter the surface tension at the crystal-medium interface, providing a possible explanation to the maintenance of the supersaturated state of itraconazole in FaSSIF. This also suggests a reduced need to include solubility-enhancing and/or stabilizing agents into formulations, which aim to create supersaturation of basic compounds in intraluminal media as natural surface active components are present.

Figure 8:
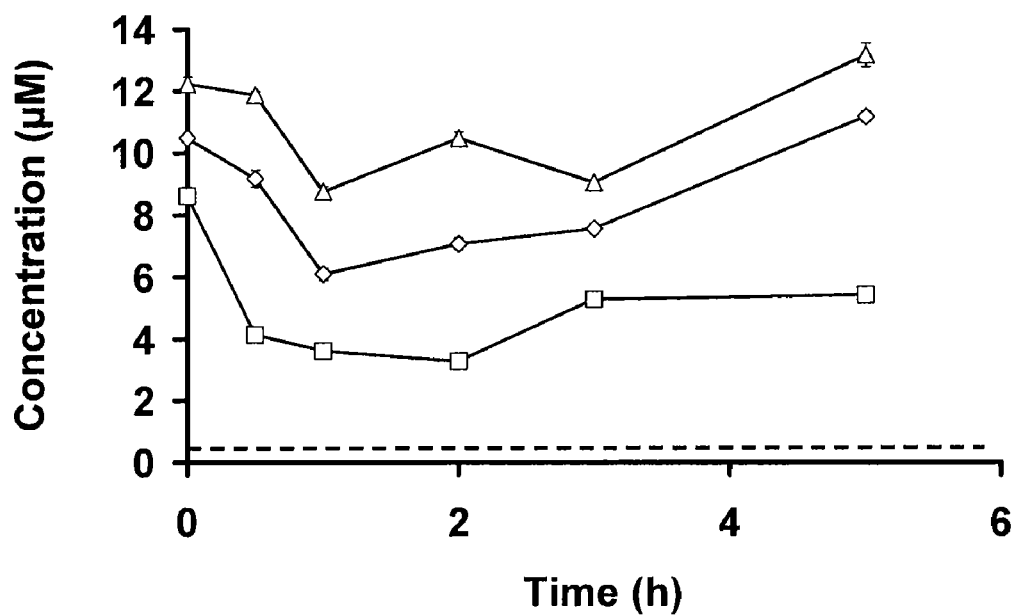
FIG. 8 shows the concentration-time profile of itraconazole in FaSSIF obtained by a solvent shift method starting from a stock solution of itraconazole in DMSO (5 mM). Theoretical concentrations amounted to 20 µM (□), 40 µM (◇) and 75 µM (Δ) respectively. The equilibrium solubility of crystalline itraconazole in FaSSIF is presented as a dotted line.

Creation of Supersaturation by Ordered Mesoporous Silica:

We also explored the possibility to create supersaturated solutions of itraconazole, a compound that has been associated with very poor formulation properties and a low aqueous solubility estimated to be ~1 ng/mL at neutral pH, by means of a solvent shift method, using DMSO as the primary solvent, which would enable to create supersaturation directly in FaSSIF without the requirement of an acidic dissolution step. Three different theoretical concentrations in FaSSIF (20, 40 and 75 µM) were thus prepared starting from a concentrated itraconazole solution in DMSO (5 mM). The concentration of dissolved itraconazole was monitored for 5 hours and the resulting concentration-time profiles are presented in FIG. 8. When actual itraconazole concentration was measured directly after solvent shifting, values were much lower than the theoretical concentrations, i.e., 8.62 µM, 10.5 µM and 12.2 µM respectively compared to 20 µM, 40 µM and 75 µM. This decrease was also observed using the pH shift method and can be attributed to an immediate partial precipitation of itraconazole After centrifugation, the nature of this precipitate was investigated by DSC analysis: the precipitate consisted of a mixture of an amorphous phase (66 wt. %) and a crystalline solid phase (34 wt. %). After this initial precipitation, itraconazole concentrations readily exceed the thermodynamic solubility concentration of itraconazole in FaSSIF for at least 5 hours. During this period, the extent of supersaturation was at least 8.2, 15.3 and 21.9 [actual drug concentration of a drug (c)/its crystalline equilibrium solubility (s) or C/S] when starting from a solution with a theoretical concentration of 20, 40 and 75 µM, respectively. This comparison shows that a supersaturated itraconazole solution in FaSSIF can be generated by spiking the neutral aqueous medium FaSSIF with a concentrated itraconazole in DMSO solution and that the extent of supersaturation depends on the initial amount of itraconazole used. Preliminary experiments excluded the influence of the DMSO content on the degree of supersaturation. The extent of supersaturation does not increase linearly with the amount of itraconazole spiked in FaSSIF, suggesting that the maximum attainable supersaturation may be limited. The slight concentration increase observed following the initial precipitation can presumably be attributed to a partial dissolution of the formed precipitate. These data evidence that supersaturation can be created by a pH shift approach, as well as by a solvent shift approach.

Solubility and In Vitro Dissolution from an Ordered Mesoporous Silica Loaded with Itraconazole:

In another example, we show the ability to enhance the release of itraconazole in SGF using ordered mesoporous silica. The release experiments with ordered mesoporous silica as a carrier were performed under acidic conditions. In this example, the release of itraconazole from ordered mesoporous oxide was assessed under pH-shift conditions in order to better reflect the in vivo situation upon arrival of the drug in the small intestine. 60 minutes after the addition of itraconazole-loaded ordered mesoporous oxide to SGF (100 µM), the medium was converted to FaSSIF. Release profiles are presented in FIG. 9. In parallel to the release of itraconazole from ordered mesoporous oxide, the performance of a commercial itraconazole product formulated with hydroxypropylmethylcellulose (HPMC) and marketed under the trade name Sporanox® (Δ) was also determined under the same conditions. After 60 minutes residence time in SGF, 35% of the amount of itraconazole loaded into ordered mesoporous oxide was released. Comparison with Sporanox® for the first 60 minutes in SGF clearly shows the solubility enhancing properties of HPMC since 80% of the itraconazole present was released. The absolute concentration of itraconazole dropped 10 times due to the dilution upon conversion of the medium to FaSSIF. The amount of dissolved itraconazole decreased to 29% after 30 minutes, and even further to 5.6% after 3 hours with Sporanox®, clearly demonstrating that precipitation occurred after the pH-shift. When the acidic medium containing the itraconazole-loaded ordered mesoporous oxide of the invention was converted into FaSSIF, precipitation was less severe, as reflected, by an amount of dissolved itraconazole being decreased to 20% after 30 minutes, and then increased to 22% after 3 hours. The extent of supersaturation (c/s) obtained when ordered mesoporous oxide was used as a carrier varied between 31.7 and 39.5 in FaSSIF (activated concentration of drug equilibrium solubility).

Figure 10:
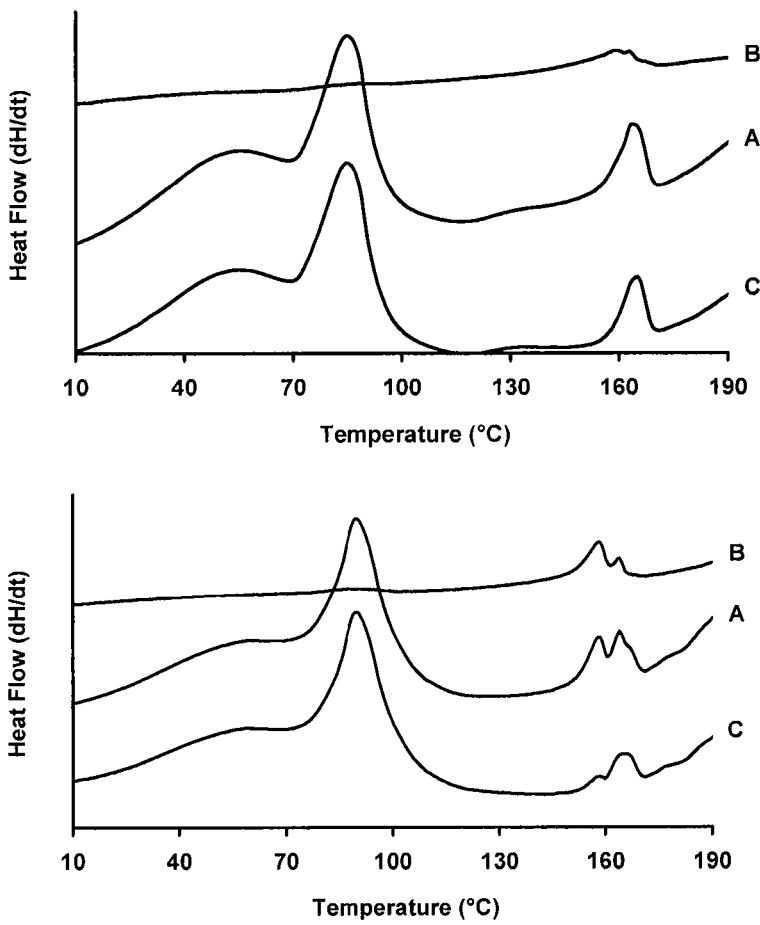
FIG. 10 shows modulated temperature differential scanning calorimetry curves of precipitates of itraconazole formed upon shifting pH to neutral conditions when using an ordered mesoporous silica of this invention (upper panel) or Sporanox® (lower panel). Each panel displays the (A) total heat flow, (B) reversing heat flow and (C) non reversing heat flow.

These observations are unexpected. Since ordered mesoporous oxide does not exhibit a solubility enhancing effect, therefore, itraconazole released from ordered mesoporous oxide was expected to be more prone to precipitation when compared to the HPMC-containing Sporanox® pellets. To clarify the different behavior between both formulations, the precipitates formed upon pH shift were collected and analyzed with modulated temperature differential scanning calorimetry. FIG. 10 presents the thermograms of both precipitates and shows that both are comprised of two different itraconazole polymorphs being characterized by (i) a reversible melting transition at 157° C. and (ii) a non-reversing melting transition at 163° C. However the precipitate formed when ordered mesoporous oxide was used as a carrier exhibits a larger fraction of the second, less stable (due to its non reversible melting transition) polymorph. In contrast, the precipitate formed with Sporanox®, exhibits a larger fraction of the first, more stable polymorph and is therefore less prone to dissolution.

Figure 11:
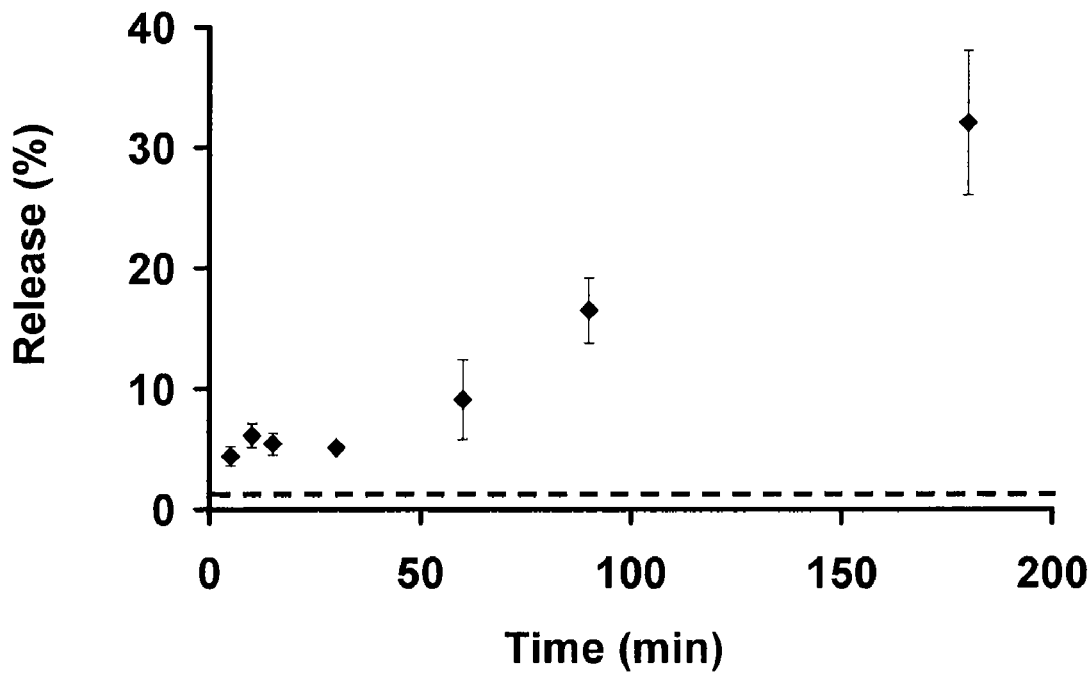
FIG. 11 shows the release profile of itraconazole from an ordered mesoporous silica of this invention in FaSSIF at pH 6.5. The equilibrium solubility of crystalline itraconazole in FaSSIF is presented as a dotted line.

Both solid formulations were able to maintain a certain extent of supersaturation after the pH shift. However, due to a potential interest for special situations (e.g. several diseases like AIDS) accompanied with a reduced acidity of the stomach, we also explored the ability of both formulations to release itraconazole in the absence of a pH gradient. Upon addition of itraconazole from Sporanox® directly into FaSSIF, the amount of itraconazole released was only 1.2% after 120 minutes, clearly a reduced performance in the absence of a preceding acidic environment. A completely different profile was obtained when itraconazole-loaded ordered mesoporous oxide was added directly into FaSSIF, as shown in FIG. 11. After an initial phase (about 30 minutes) during which about 5% (much higher than the thermodynamic equilibrium concentration) of itraconazole was released from its carrier, the amount of itraconazole released rose quickly to 17% and 32% after 90 and 120 minutes, respectively. This experiment shows that an ordered mesoporous silica (ordered mesoporous oxide) is able to create a pH-independent supersaturated state of itraconazole in FaSSIF. This finding clearly indicates that ordered mesoporous oxide has the capacity to release loaded drugs in conditions where the gastric acidity of the stomach is reduced. In this way, the pH dependence of drug solubility and formulation performance can be circumvented.

EXAMPLE 10

Caco-2 Cell Monolayer Transport with an Ordered Mesoporous Silica Loaded with Itraconazole As receiver medium for Caco-2 transport experiments, 0.2 wt.-% TPGS (D-α-tocopherol polyethylene glycol 1000 succinate, commercially available from Eastman, Anglesey, England) in transport medium (hereinafter referred to as TM) [HBSS Hanks' Balanced Salt Solution supplemented with glucose to obtain a final concentration of 25 mM, commercially available from Sigma-Aldrich, Steinheim, Germany and Hepes-buffer (10 mM, pH 7.4, N-2-hydroxyethylpiperazine-N'-2-ethanesulfonic acid, commercially available from Lonza, Verviers, Belgium)] was used. To maintain sink conditions, TPGS was included in the medium added to the basolateral side of the Caco-2 cell monolayer.

Caco-2 cells were purchased from Cambrex Biosciences, Walkersville, Md., United States of America. Caco-2 cells were grown in 75 $cm^2$ culture flasks at 37° C. in an atmosphere of 5% $CO_2$ and 90% relative humidity. Cells were passaged every 3-4 days (at 70-80% confluence) at a split ratio of 1 to 7. Cells were negative for *Mycoplasma* infection.

For transport experiments, Caco-2 cells were plated at a density of 88,500 cells/insert on Costar® Transwell membrane inserts (3 μm pore diameter, 12 mm diameter; commercially available from Corning Inc., New York). Confluence was reached within 3-4 days after seeding and the monolayers were used for the experiments 18-19 days post-seeding. Cell passages between 50 and 85 were used in the experiments. Transepithelial Electrical Resistance (hereinafter referred as TEER) values were measured with an EndOhm Voltohmmeter (commercially available from WPI, Aston, England). Only monolayers with initial TEER values higher than 200 $\Omega \cdot cm^2$ were used. All volumes amounted to 0.5 mL at the apical side of the monolayer and 1.5 mL at the basolateral side. After rinsing the monolayers 3 times with TM, a pre-incubation step (30 minutes) with TM (control) was performed.

After measuring TEER values, transport was initiated by adding to the donor compartment: (a) an itraconazole solution in FaSSIF (20, 40 and 75 μM respectively) obtained by DMSO spiking, (b) a suspension of the ordered mesoporous silica of example 7 loaded with itraconazole in a selected medium or (c) Sporanox® pellets in FaSSIF. The amount of itraconazole added to a formulation was kept constant at a theoretical value to eventually generate a donor solution of 75 μM. Samples (100 μL) were taken from the acceptor compartment after 30, 60 and 90 minutes and replaced with 100 μL fresh receiver medium. During the experiments, 0.2% TPGS was included in the TM added to the basolateral compartment to install sink conditions. Transport was also studied using rabbit plasma as the receiver medium: when a 75 μM supersaturated solution was applied under these conditions, total transport after 90 minutes was comparable to the one obtained when 0.2% TPGS in TM was used, suggesting that this medium can be considered as a valid biorelevant substitute. The samples were diluted with methanol (1:1 volume ratio) and itraconazole concentration was determined by HPLC. TEER values were measured again at the end of the experiment and were higher than 95% of the initial value.

As an additional control of the monolayer integrity, sodium fluorescein flux was measured at the end of the experiment. Briefly, sodium fluorescein (1 mg/mL) was added to the apical compartment and after 60 minutes, samples were taken from the basolateral compartment, followed by TEER measurement. The amount of sodium fluorescein appearing in the basolateral compartment was measured by UV spectrophotometry (Uvikon 810P spectrophotometer, commercially available from Kontron Instruments, Watford, England) at 490 nm. Sodium fluorescein flux values across the monolayers were below 0.6% $h^{-1} \cdot cm^{-2}$. None of the test conditions affected the integrity of the tight junctions during the time period studied (based on TEER measurements and sodium fluorescein flux).

In this experiments, it was explored whether supersaturation in a biorelevant medium may be accompanied with increased absorption. Such a beneficial effect of supersaturation on intestinal absorption was first explored by using the solvent shift method. Three donor concentrations of itraconazole in FaSSIF were prepared:

a saturated itraconazole solution,
a 10 μM supersaturated condition, and
a 75 μM supersaturated condition.

Figure 12:
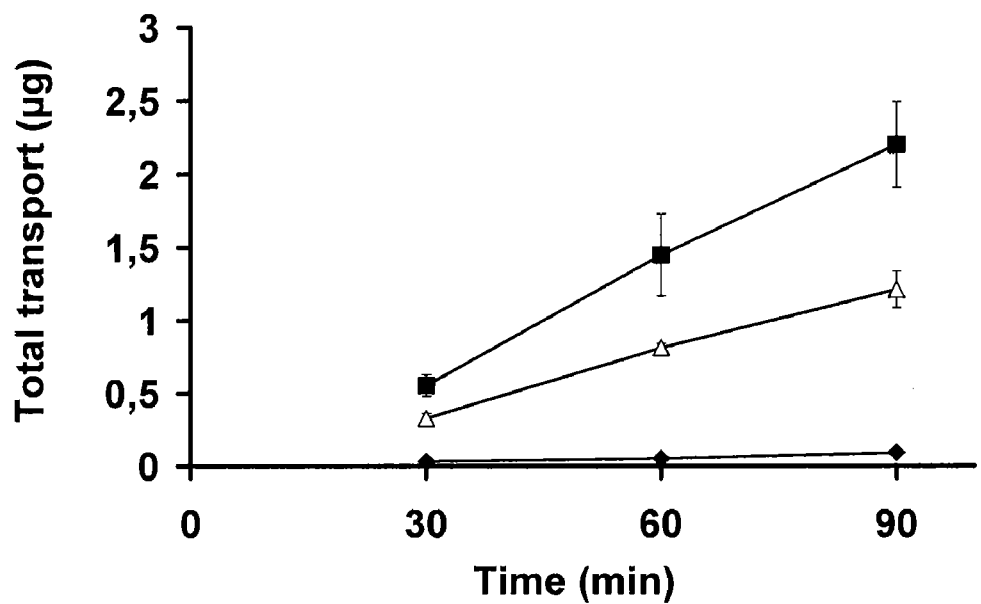
FIG. 12 shows the total transport (μg) of itraconazole over time across a Caco-2 cell monolayer starting from a saturated itraconazole solution (♦), a 10 μM supersaturated solution (Δ), and a 75 μM supersaturated solution (■) in FaSSIF respectively.

Transepithelial transport is presented in FIG. 12. The concentration of itraconazole in the donor compartment is not constant due to precipitation occurring after solvent spiking in the intestinal medium (FIG. 7); consequently no permeability values could be calculated and transport was expressed as the total amount of itraconazole appearing at the basolateral side of the Caco-2 cell monolayer. The saturated solution generated a total transport of 0.09 μg after 90 minutes. When the 10 μM and 75 μM supersaturated itraconazole conditions were used in the donor compartment, total itraconazole transport increased to 1.2 μg and 2.2 μg, respectively. In FIG. 7 it was shown that the extent of supersaturation created for the 75 μM condition was about 25. This illustrates that the extent of supersaturation is translated into a similar increase in transepithelial transport.

It was then explored whether a similar transport enhancement for itraconazole based on a formulation with ordered mesoporous oxide as a carrier is achievable. Results from transport experiments across a Caco-2 cell monolayer were also compared with the commercial itraconazole product Sporanox®. Since Caco-2 is not compatible with acidic medium, the acidic-neutral pH shift normally encountered in healthy people was simulated by an acidic dissolution step, prior to conversion into FaSSIF; this medium was subsequently added to the donor compartment of the Caco-2 system. The amount of itraconazole present in the itraconazole-loaded ordered mesoporous oxide or Sporanox® used would eventually result in a theoretical maximal concentration of 75

µM. Transport was monitored over time as presented in FIG. 12. Total transport of itraconazole was significantly higher for the ordered mesoporous oxide formulation, compared to Sporanox®, amounting to 1.46 µg and 1.26 µg after 90 minutes, respectively. This is in agreement with the in vitro dissolution profiles presented in FIG. 9 showing a higher extent of super-saturation after pH shift in the case of ordered mesoporous oxide.

Figure 13:
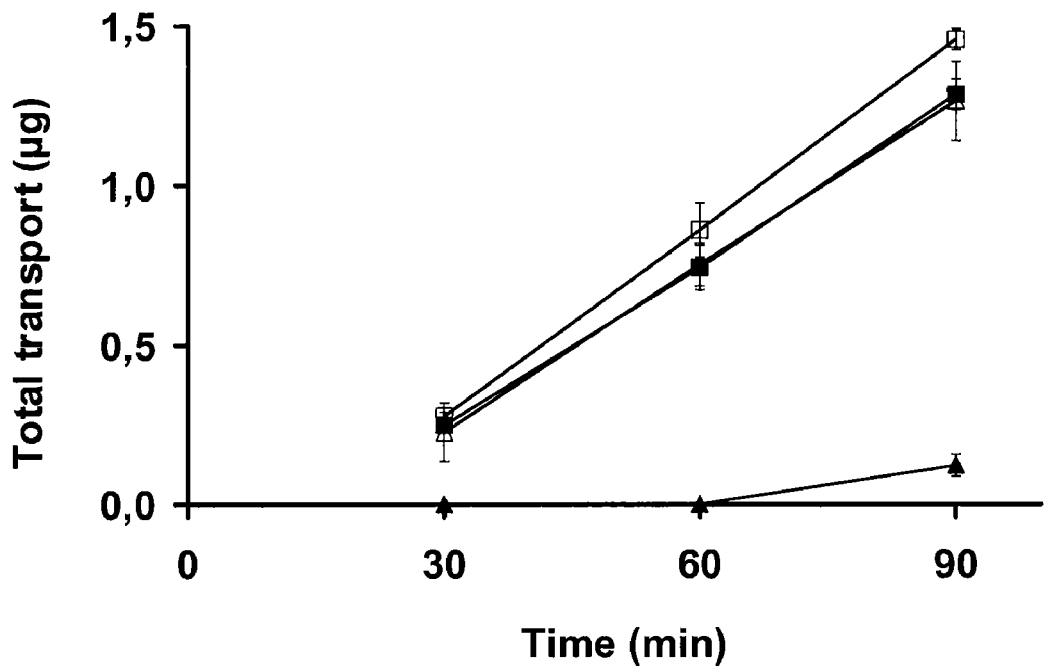
FIG. 13 shows the total transport (μg) of itraconazole over time across a Caco-2 cell monolayer. Donor media were an ordered mesoporous oxide suspension with a theoretical itraconazole concentration of 75 μM in FaSSIF without (■) and with (□) a prior acidic 1 hour dissolution step, a suspension of Sporanox® pellets with a theoretical itraconazole concentration of 75 μM in FaSSIF without (▲) and with (Δ) a prior acidic 1 hour dissolution step.

It was further examined whether transport of itraconazole can be enhanced independently from prior dissolution in an acidic medium. Two different amounts of itraconazole loaded ordered mesoporous oxide eventually resulting in theoretical concentrations of 10 µM and 75 µM in FaSSIF were chosen as the donor conditions and total transport was monitored over time as presented in FIG. 14 also including a comparison with a saturated solution of itraconazole in FaSSIF. After 90 minutes, the formulation induced super-saturation, resulting in a total transport of itraconazole of 0.42 µg and 1.31 µg for the 10 µM and 75 µM donor conditions, respectively. As compared to the total transport achieved when using a saturated itraconazole solution (0.09 µg), it is clear that ordered mesoporous oxide as a carrier remarkably increases transport of itraconazole across the Caco-2 cell monolayer. Ordered mesoporous oxide is thus able to create an in vitro supersaturated state and enhance transport of itraconazole without a prior acidic dissolution step. The performance of the commercial product Sporanox® under similar conditions is illustrated in FIG. 13. Transport generated by using Sporanox® pellets amounted to 0.12 µg after 90 minutes, i.e. lower than transport observed with ordered mesoporous oxide as a carrier. Ordered mesoporous oxide behaves as an inert matrix releasing itraconazole without changing any properties of the aqueous medium. In contrast, Sporanox® is based on a different approach involving release in the acidic environment of the stomach together with a viscosity increase of the medium due to the co-dissolving HPMC-phase. However, when no acidic dissolution is present prior to absorption, the biopharmaceutical performance of Sporanox® is drastically reduced, whereas ordered mesoporous oxide as a carrier maintains its ability to boost the transepithelial flux of the basic drug itraconazole.

EXAMPLE 11

In Vivo Perfusion of an Ordered Mesoporous Silica Loaded with Itraconazole in Rats The rats used in this study were housed—according to European Regulations—in the Central Animal Facilities of Leuven University. In situ perfusion experiments were performed as described by Annaert et al., *J. Pharm. Sci.* (2000) 89:1054-62. Male Wistar rats of about 350 g were anaesthetized with a ketamin (Anesketin, commercially available from Eurovet, Heusden, Belgium)—xylazin (Xyl-M 2%, commercially available from VMD, Arendonk, Belgium) mixture (87.5 and 8.75 mg/kg respectively). The left jugular vein was cannulated with a heparinized (50 IU·mL$^{-1}$) polyethylene cannula (1.02 mm outer diameter; commercially available from Portex, Kent, United Kingdom) for blood supply from a donor rat during the perfusion experiment. A laparotomy was performed and the small intestine was exposed. A segment of the ileum (4-10 cm) was isolated by inserting two glass cannulas (4 mm o.d., 3 mm i.d.) at the proximal and distal end of the segment. Polyethylene tubing (6.5 mm o.d., 3.1 mm i.d.) was connected to the inlet cannula. The intestinal content was removed by perfusing the segment with pre-warmed TM (38° C.) at a flow rate of 3 mL/min. The perfusion pump (Minipuls3, commercially available from Gilson, Middleton, USA) was placed between the reservoir and the inlet cannula. After pre-incubation of the intestine with TM, the mesenteric vein draining the isolated part of the ileum was cannulated using the top end (1 cm) of a catheter (Insyte-W® 0.7×19 mm, commercially available from Beckton Dickinson, Salt Lake City, Utah). The cannula was secured with a knot and connected to a piece of 40 cm silastic tubing (0.64 mm internal diameter; 1.19 mm outer diameter, Helix Medical, USA).

In situ perfusion experiments with itraconazole were performed with a flow rate of the perfusate amounting to 1 mL/min. The perfusion experiments were carried out using FaSSIF with (a) a saturated itraconazole solution, (b) a super-saturated itraconazole solution generated by solvent spiking with DMSO, (c) a suspension of ordered mesoporous oxide loaded with itraconazole and (d) Sporanox® pellets. The maximal theoretical concentration of conditions (b), (c) and (d) amounted to 75 µM. At the beginning of the perfusion with the itraconazole solution, blood was collected from the mesenteric vein and donor blood supply [supplemented with ketamin-xylazin (12.5 and 1.25 mg·kg$^-$·h$^{-1}$ respectively)] was initiated via the jugular vein at a rate of 0.3 mL/min using a syringe pump (Pilot A2, commercially available from Fresenius Vial, Grenoble, France). Experiments with media (a) and (b) as the perfusate were performed under an open-loop set-up. Experiments with the formulations (c) and (d) were performed under a closed-loop (perfusate was recirculated) system. Blood from the mesenteric vein was collected in heparinized tubes over 5-minutes time intervals for 60 minutes. In addition, samples were taken from the perfusion medium at 0-20-40-60 minutes after the start of the perfusion. The collected blood samples were centrifuged at 4,000 rpm for 10 minutes at 4° C. to separate the cells from the plasma within 30 minutes after collection. Plasma samples were frozen and stored prior to analysis at −20° C. The collected perfusate samples were centrifuged for 15 minutes at 37° C. 400 µL supernatant were mixed with 400 µL mobile phase (78% methanol, 22% buffer 25 mM sodium-acetate pH 3.3) and stored at 4° C. prior to analysis.

Plasma concentrations of itraconazole were determined by HPLC as follows. To 1 mL of plasma, 100 µL of the internal standard solution was added [R051012 commercially available from Janssen Pharmaceutica, 2.5 µM in 0.2M HCl]. After addition of 500 µL 2M NaOH, itraconazole and hydroxy-itraconazole were extracted with 4 mL diethyl ether. Following centrifugation at 4,000 rpm for 5 minutes, the upper organic layer was transferred into a fresh tube. The organic solvent was evaporated under a gentle stream of air and the extraction residue was dissolved in 200 µL of a methanol/water mixture (50:50 by volume), of which 99.5 µL was injected into the HPLC system. Concentrations of itraconazole and hydroxy-itraconazole were determined using an isocratic HPLC method. The HPLC system (commercially available from Merck-Hitachi, Darmstadt, Germany) used for the analysis of the plasma samples consisted of an Elite LaCrom L-2130 HPLC pump, an autosampler model L-2200 and a UV detector model L-2400. Separations were achieved using a Novapak C-18, 4 µm, under radial compression. The mobile phase consisted of methanol/25 mM sodium acetate at pH 3.3 (78:22 by volume). The mobile phase was filtered through a 0.45 µm PTFE membrane before use. The flow rate of the mobile phase with online degassing was maintained at 1.75 mL/min and the effluent was monitored at a wavelength of 265 nm. Itraconazole, hydroxy-itraconazole and R051012 were eluted with retention times of 4.5, 8.0 and 11.5 minutes, respectively. The standard curves were linear over the concentration range of 7.8 nM to 500 nM. The intraday relative standard deviation was less than 7.3% for itraconazole and less than 5.4% for hydroxy-itraconazole over the concentration range studied (n=6).

These experiments in a rat in situ perfusion set up still better resembles the in vivo situation than the Caco-2 system of example 10.

At first, absorption was explored using a saturated solution and a supersaturated solution obtained by the solvent shift approach. A typical cumulative concentration-time profile is presented in FIG. 15, illustrating that a drastic increase in absorption was obtained when switching the perfusion medium from a saturated to a supersaturated solution. This confirms that supersaturation is critical to enhance the extent of absorption of poorly water-soluble compounds like itraconazole. The concentration of the main metabolite, hydroxy-itraconazole, was also determined, but no significant amounts could be detected, indicating that metabolism at the site of absorption is negligible.

The performance of ordered mesoporous oxide as a biocompatible matrix to enhance transport was evaluated by generating intraluminal supersaturation. The performance of Sporanox® was also investigated and compared with the ordered mesoporous oxide formulation of this invention. No preceding dissolution in an acidic environment was allowed thus simulating the condition in which the gastric acidity is reduced.

Total transport of itraconazole into the mesenteric blood was corrected for the length of the perfused part of the intestine and presented in Table 1.

TABLE 1

| Perfusate medium | Total transport after 60 minutes (nmol · cm$^{-1}$) |
|---|---|
| Saturated solution | 0.03 |
| Supersaturated solution[‡] | 0.50 |
| Ordered mesoporous oxide suspension[‡] | 0.70 |
| Sporanox ® suspension[‡] | 0.29 |

[‡]the theoretical concentration amounted to 75 μM

These data clearly illustrate that a drug formulation based on an ordered mesoporous silica according to the present invention is able to preserve its dissolution enhancing properties under conditions with a reduced gastric acidity. Under the same conditions, the commercial itraconazole product Sporanox® exhibits a lower performance when hypochlorhydria is involved.

EXAMPLE 12

Preparation and Characterization of Mesostructured Silica Materials

Four different mesostructured silica materials were synthesized according to the methodology described in WO 1999/037705 and their porosity was characterized using nitrogen adsorption. Table 2 indicates texture characteristics including:
pore width (w),
BET surface area (S),
mesopore surface area ($S_p$) determined from t-plot analysis, and
total pore volume ($V_t$) determined from t-plot analysis

TABLE 2

| Materials | w (nm) | S (m$^2$ · g$^{-1}$) | $S_p$ (m$^2$ · g$^{-1}$) | $V_t$ (cm$^3$ · g$^{-1}$) |
|---|---|---|---|---|
| SBA-15$_{4.5}$ | 4.5 | 506 | 321 | 0.42 |
| SBA-15$_{6.4}$ | 6.4 | 662 | 483 | 0.63 |
| SBA-15$_{7.9}$ | 7.9 | 661 | 461 | 0.77 |
| SBA-15$_{9.0}$ | 9.0 | 662 | 404 | 0.80 |

EXAMPLE 13

Preparation and Characterization of Mesostructured Silica Materials Loaded with Itraconazole The loading of itraconazole onto the four different mesostructured silica materials of example 12 was performed according to the "solvent method" generically described above, and using methylene chloride as the solvent in excess to itraconazole. The physical state of itraconazole after solvent evaporation was investigated with Differential Scanning Calorimetry, and data were interpreted in view of the fact that: crystalline itraconazole melts at 168° C., while glassy itraconazole is characterized by three typical endothermic transitions upon heating, being a glass transition at 60° C. and two endothermic transitions due to its liquid crystalline nature at 75° C. (as a result of rotational restriction) and 90° C. (transition from the chiral nematic mesophase to an isotropic viscous liquid).

Figure 16:
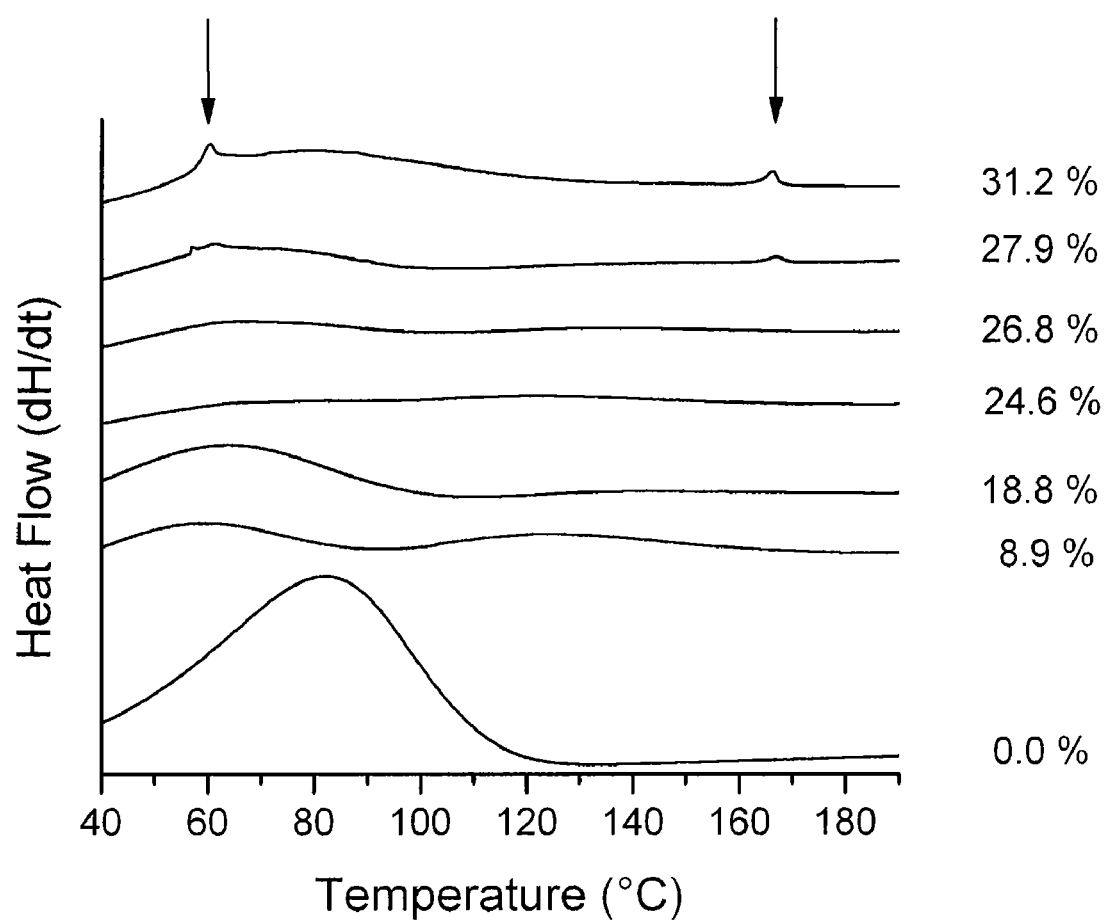
FIG. 16 shows the differential scanning calorimetry curves of a mesostructured silica material loaded with different amounts of itraconazole.

These typical transitions allow to differentiate between the presence of itraconazole particles, either glassy or crystalline, or drug that is molecularly deposited onto the surface of different mesostructured silica materials. FIG. 16 represents DSC curves of an itraconazole-loaded mesostructured silica material with a pore size of 6.4 nm (SBA-15$_{6.4}$) and with an itraconazole loading ranging from 8.9 wt. % to 31.2 wt. %, compared to the unloaded mesostructured silica material. At a 24.6 wt. % itraconazole loading ratio, the absence of bulk phase transitions reveals that the itraconazole is molecularly dispersed. This value is very close to the monolayer capacity that can be predicted by calculation, assuming a monolayer coverage. At an itraconazole loading of 26.8 wt. % and higher, enthalpic responses show the superposition of two endothermic transitions at 60° C. and 168° C. which characterize the glass transition and melting of bulk phase itraconazole, respectively. The capacity of SBA-15$_{6.4}$ to incorporate molecularly dispersed itraconazole appears to be exceeded above 24.6 wt. %. The existence of a critical loading was observed for the other SBA-15 materials too: the loading capacity was 27.8% for SBA-15$_{9.0}$, 26.5% for SBA-15$_{7.9}$ and 21.3% for SBA-15$_{4.5}$. Each DSC curve of SBA-15 loaded with itraconazole is also characterized by one or two broad endothermic transitions which represent the desorption of physically adsorbed water. With increasing loading of itraconazole onto SBA-15$_{6.4}$, this endothermic desorption of water tends to shift to lower temperatures indicating that the adsorption of itraconazole renders the surfaces less hydrophilic. Unloaded SBA-15 exhibits an endothermic maximum of its water desorption around 85° C., while loaded materials are characterized by an endothermic response around 65° C.

EXAMPLE 14

Figure 17:
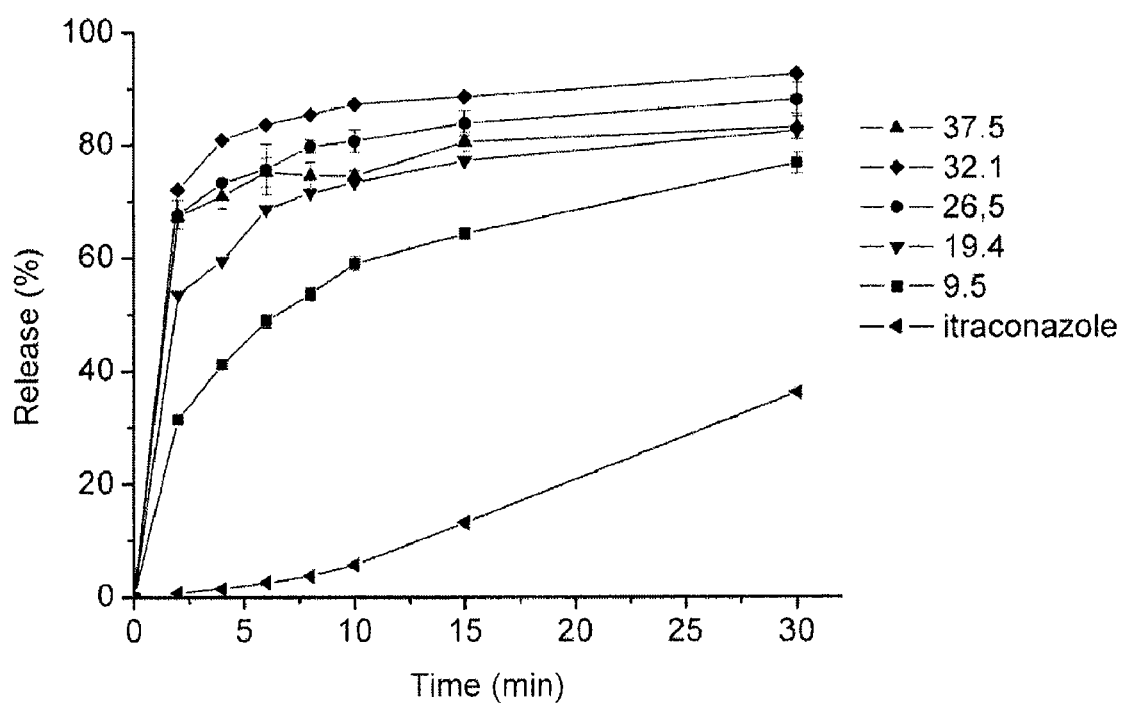
FIG. 17 shows the release profiles of itraconazole from a mesostructured silica material at different drug loadings.
Figure 29:
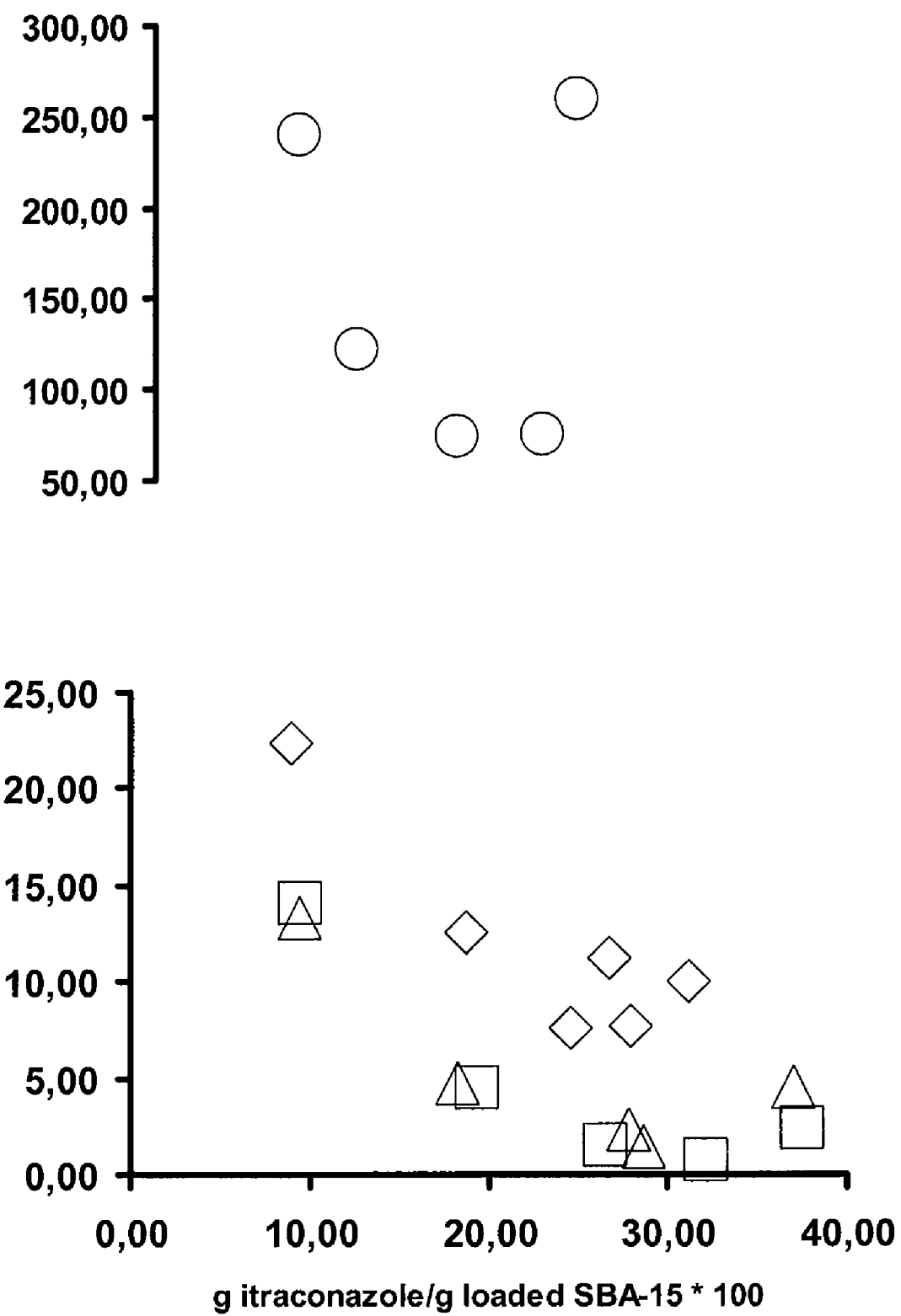
FIG. 29 shows the time value (τd) in relating to the drug load (% w/w) whereby 63.2% of the itraconazole has been released from SBA-15 6.4 ◇, SBA-15 7.9ε, SBA-15 9.0Δ and SBA-15 4.5 O. The parametric display of the distribution curve is according to the Rosin-Rammler-Sperling-Bennet-Weibull distribution (RRSBW).

In Vitro Release of Mesostructured Silica Materials Loaded with Itraconazole at Different Drug Loading Ratios The in vitro release performance of an itraconazole loaded mesostructured silica material (SBA-15$_{7.9}$ from example 12)

was assessed using simulated gastric fluid at pH 1.2. All release experiments showed good reproducibility. The release behavior of itraconazole from SBA-15$_{7.9}$ is illustrated for different drug loadings in FIG. 17 and compared to the dissolution of crystalline itraconazole. After 30 minutes, SBA-15$_{7.9}$ released at least 70% of its initial drug content for every loading, compared to 36% only for crystalline itraconazole. Drug release after 5 minutes was above 70% at a drug loading of 26.5 wt. % or above. Increasing the loading beyond the optimum loading ratio of 31.2 wt. % leads to a decreased release rate which may be due to the presence of crystalline and amorphous regions of itraconazole, and itraconazole intermolecular hydrophobic interactions. A dependence of percentage release on drug loading was observed for each investigated SBA-15 carrier as shown in FIG. 29.

EXAMPLE 15

Figure 18:
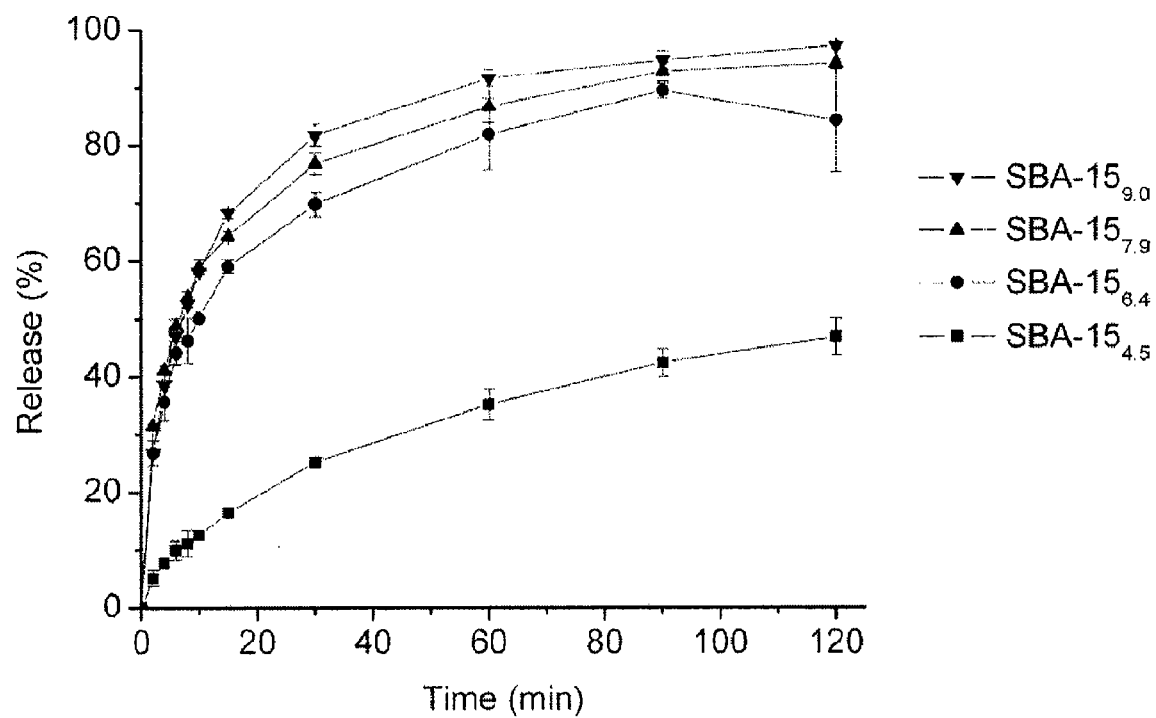
FIG. 18 shows the release profiles of itraconazole from mesostructured silica materials with different pore sizes.

In Vitro Release of Itraconazole from Mesostructured Silica Materials with Different Pore Sizes To investigate the influence of the pore size on the release behavior of itraconazole, mesostructured silica materials from example 12 with different pore widths were loaded with 10 wt. % drug and their in vitro release performances compared. Prior DSC analysis had shown no endothermal transitions characteristic for bulk properties of itraconazole, evidencing the molecularly dispersed state of adsorbed molecules in all cases. Release curves (FIG. 18) reveal that enlarging the pore size from 4.5 nm to 6.4 nm drastically enhances the release of itraconazole [molecular weight (MW) 705.6 and molecular volume (MV) 502±7 cm$^3$/mole at 20° C. and atmospheric pressure]. A further increase in pore size to 7.9 nm and 9.0 nm results only in a minor further improvement. These data suggest the occurrence of molecular diffusion barriers in pores measuring 4.5 nm and the existence of a critical pore size, which discriminates between facile diffusion and sterically hindered diffusion of itraconazole through the pores of such materials. These findings show that itraconazole release from the materials of Example 12 can be tuned by varying the pore size of the material.

EXAMPLE 16

Figure 19:
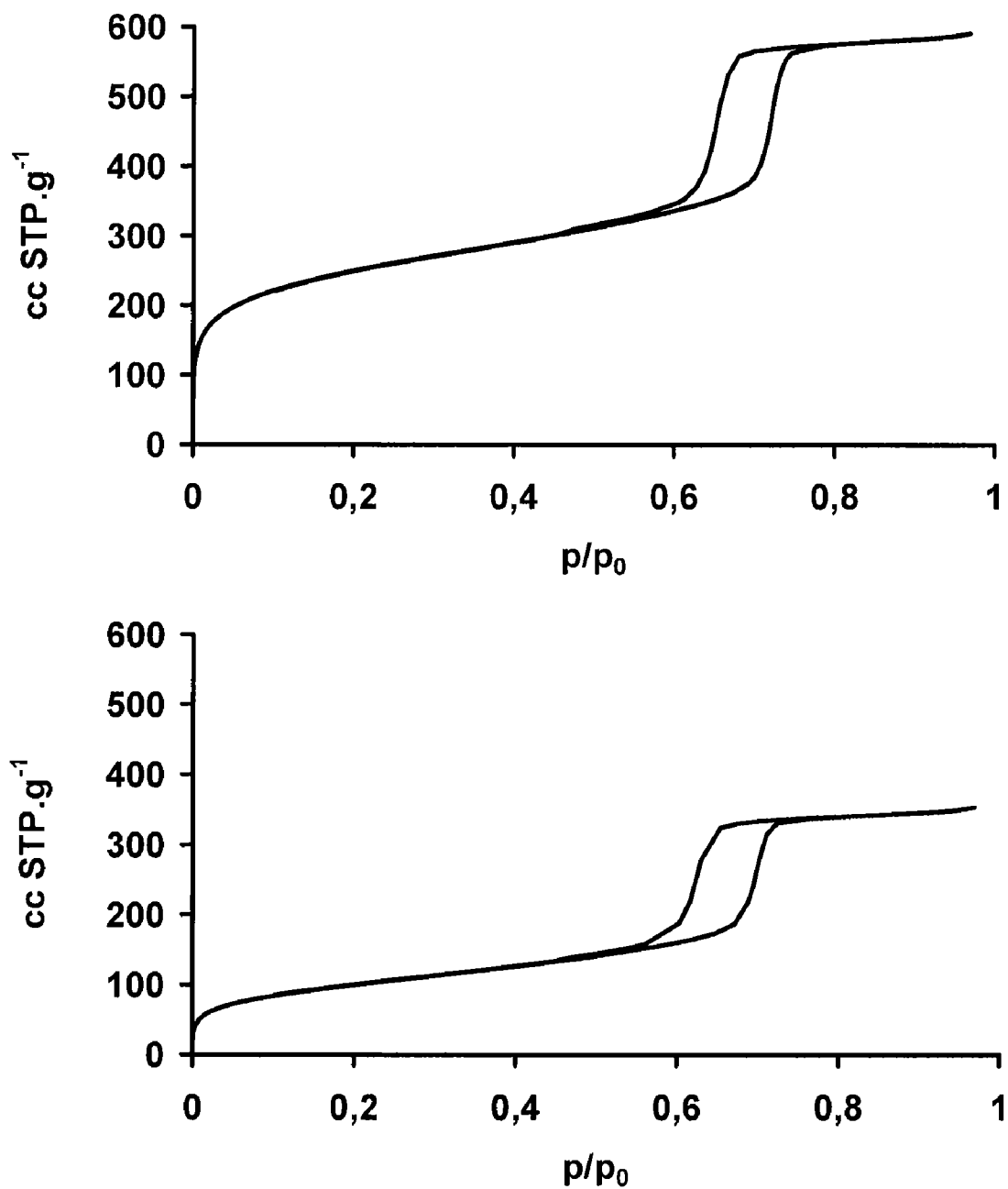
FIG. 19 shows the nitrogen adsorption isotherms of an ordered mesoporous material before (top) and after (bottom) loading with itraconazole.

Characterization of Ordered Mesoporous Oxide Herein Specifically Ordered Mesoporous Silica Before and After Loading with Itraconazole The detailed structure of the ordered mesoporous silica of example 7 was assessed by scanning electron microscopy (SEM, using an XL30 FEG instrument from Philips, Eindhoven, The Netherlands; samples gold-plated prior to imaging) and transmission electron microscopy (TEM, using a CM20 apparatus from Philips, Eindhoven, The Netherlands, operated at 200 kV), showing a morphology defined as single particles with sizes ranging from 0.2 to 1 μm which act as randomly oriented building blocks to form larger aggregates of approximately 50 μm. The internal pore structure was determined using nitrogen adsorption. The nitrogen adsorption isotherm presented a hysteresis loop with parallel steep branches typical of material with a uniform pore size. Nitrogen adsorption isotherms, before and after loading with itraconazole, are presented in FIG. 19. Drug loading itself was determined, by a long-term release under sink conditions and by TGA, as being 21 wt. %. Loading ordered mesoporous silica with itraconazole significantly changed the porosity of the sample due to the incorporation of itraconazole into the pores. A decrease in amount of nitrogen adsorbed reflects the decreased pore volume of the carrier, while the slightly shifted hysteresis loop to lower p/p$_0$ values upon loading with itraconazole characterizes a reduced pore size. The total pore volume was decreased from 0.85 cm$^3$·g$^{-1}$ to 0.50 cm$^3$·g$^{-1}$ after loading ordered mesoporous silica with itraconazole. The mesopore diameter of ordered mesoporous silica according to nitrogen adsorption is about 7.3 nm. After itraconazole loading, the mesopore diameter probed with nitrogen was decreased to 6.6 nm. Loading with itraconazole also decreased the BET surface area of ordered mesoporous oxide from 844 m$^2$·g$^{-1}$ to 355 m$^2$·g$^{-1}$.

EXAMPLE 17

In Vitro Dissolution of an Ordered Mesoporous Oxide Herein Specifically Ordered Mesoporous Silica Loaded with Itraconazole in Simulated Gastric Fluid The itraconazole-loaded ordered mesoporous oxide powders of example 8 were suspended in simulated gastric fluid (0.1 M HCl containing 0.2 wt. % NaCl) in the absence or presence of 0.5 wt. % sodium lauryl sulfate (commercially available from Certa S. A., Braine-l'Alleud, Belgium). SLS was added when sink conditions were preferred. The dissolution study was performed in test tubes of 10 mL under gentle agitation using a rotary mixer (commercially available from Snijders, Tilburg, The Netherlands). The amount of material in the dissolution medium was adjusted to obtain a fixed concentration of drug substance (0.08 mg·mL$^{-1}$) corresponding to about 10% of the saturation solubility of itraconazole in simulated gastric fluid containing 0.5 wt.-% SLS. At specific time intervals, samples were collected and the medium was filtered through a 0.45 μm PTFE membrane. Prior to analysis by HPLC, samples were diluted with methanol (1:1) to prevent precipitation during analysis.

Samples from the in vitro dissolution study were also assayed using an isocratic HPLC method. The HPLC system consisted of a LaChrom® L-7100 HPLC pump, an autosampler model L-7200 equipped with a 100 μL loop, a UV detector model L-7420 set at 260 nm, and an Interface D-7000 (all commercially available from Merck, Darmstadt, Germany). UV signals were monitored and peaks were integrated using the D-7000 HSM software. The separation of itraconazole was performed on a RP-18 150×4.6 mm 5 μm Hypersil silica column (commercially available from Thermo Electron Corporation, Waltham, USA) at room temperature. The mobile phase consisted of an acetonitrile/tetrabutyl ammonium hydrogen sulfate 0.01 N mixture (55:45 by volume), and was filtered through a 0.45 μm PTFE membrane and degassed by ultrasonication before use. The flow rate amounted to 1.5 mL/min. The standard curves were linear over the concentration range of 0.0001 mg·mL$^{-1}$ to 3 mg·mL$^{-1}$.

Figure 20:
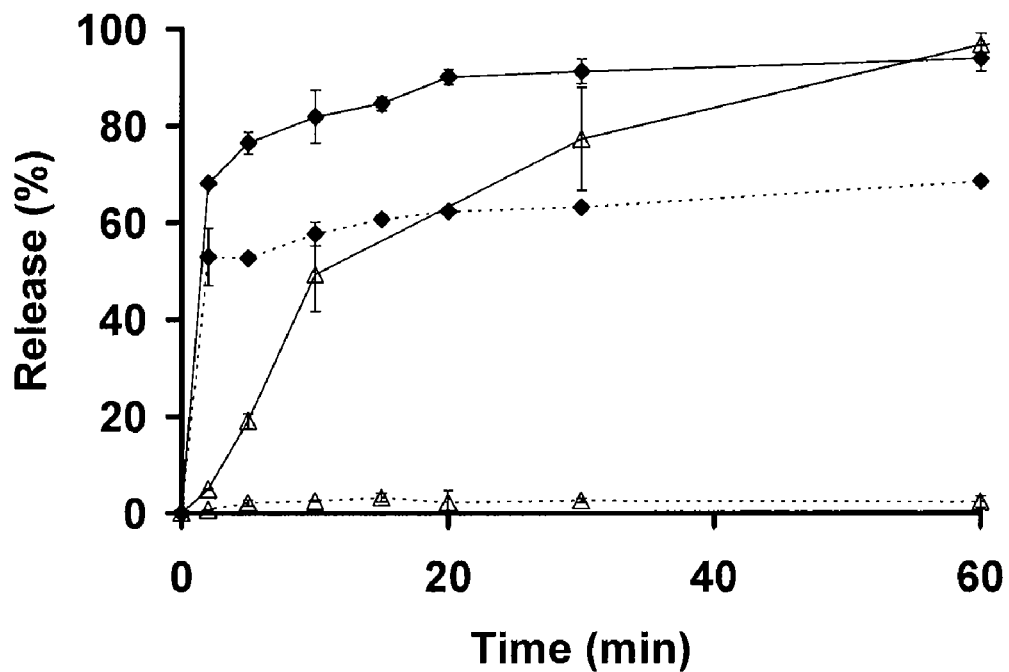
FIG. 20 shows dissolution of pure crystalline itraconazole (Δ) and release of itraconazole from ordered mesoporous oxide in simulated gastric fluid (♦) in the absence (dashed line) or presence (continuous line) of SLS.

Release of itraconazole from ordered mesoporous oxide was compared with the dissolution of pure crystalline itraconazole in simulated gastric fluid (SGF, 0.1 M HCl) and under sink conditions created by SLS in the medium (SGF-SLS, 0.1 M HCl). The in vitro profiles are depicted in FIG. 20. In SGF-SLS, 76% of the initial itraconazole content was released from the drug-loaded ordered mesoporous oxide after 5 minutes, compared to only 19% for pure crystalline itraconazole.

In SGF without SLS, the same enhanced release behavior was present in non-sink dissolution medium, achieving a supersaturated solution with a 11-fold higher itraconazole concentration (45 µg/mL) compared to its thermo-dynamic solubility at pH 1 (4 µg/mL). After 5 minutes, 53% from the initial amount of itraconazole entrapped into ordered mesoporous oxide was released, compared to only 2% for pure crystalline itraconazole. These data clearly illustrate that loading itraconazole into ordered mesoporous oxide circumvents the slow dissolution kinetics and low water solubility of the pure crystalline drug in non-sink conditions.

EXAMPLE 18

Preparation and In Vitro Dissolution Characteristics of an Itraconazole Pharmaceutical Formulation Including an Ordered Mesoporous Silica The itraconazole-loaded ordered mesoporous oxide powders of example 8 were mixed with croscarmellose (25 wt.-%), lactose (25 wt.-%) and SLS (1 wt.-%). This physical mixture was filled into hard gelatin capsules size 3 (when intended for administration to rabbits) or size 00 (when intended for administration to dogs). As a control for an in vitro dissolution study, Sporanox® itraconazole pellets were removed from the commercial capsules and refilled, with or without the same excipients as described above, into the same hard gelatin capsules as described above.

The itraconazole capsules dose amounted to:
8.1 mg (itraconazole loaded into ordered mesoporous oxide), 8.6 mg (Sporanox®) and 8.4 mg (crystalline itraconazole) respectively when intended for administration to rabbits, and
20.4 mg (itraconazole loaded into ordered mesoporous oxide), 23.2 mg (Sporanox®) and 22.8 mg (crystalline itraconazole) respectively when intended for administration to dogs.

All results from the following in vitro dissolution study were normalized to the dose provided by the capsules.

Figure 21:
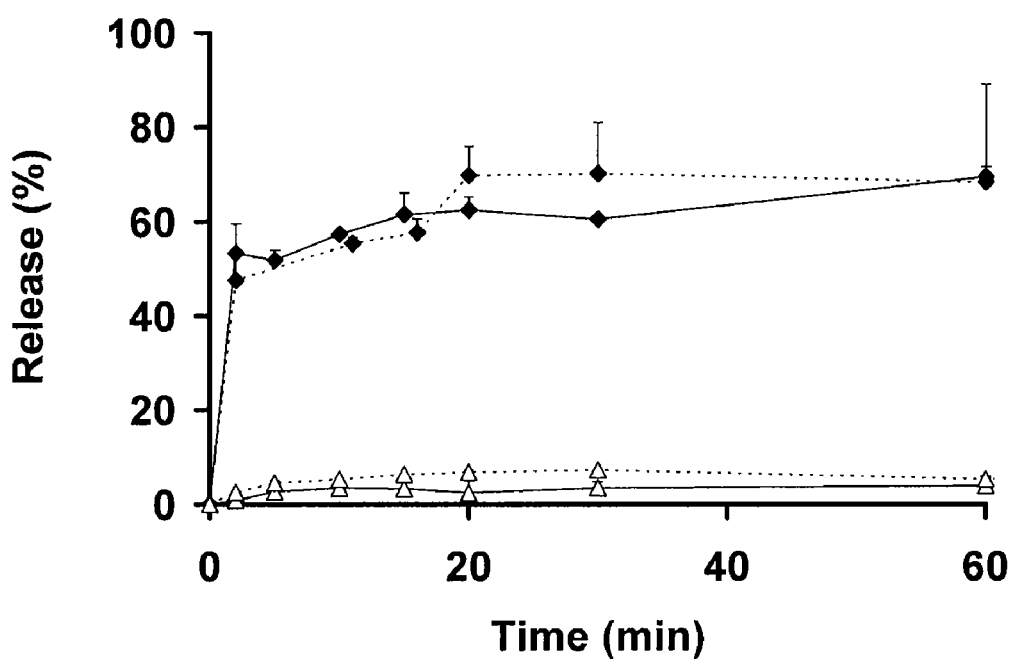
FIG. 21 shows the dissolution of crystalline itraconazole (Δ) and the release of itraconazole from ordered mesoporous oxide (♦) in the presence (dashed lines) or absence (continuous lines) of excipients included in hard gelatin capsules formulations.

In order to comparatively evaluate the biopharmaceutical performance of the ordered mesoporous oxide powder of example 8 as a carrier for itraconazole, hard gelatin capsules including 49 wt. % ordered mesoporous oxide loaded with itraconazole and a combination of excipients suitable for rapid disintegration were used, and the drug release properties were investigated in SGF (simulated gastric fluid, 0.1M HCl containing 0.2 wt. % NaCl). The possible influence of the excipients on the release properties of the ordered mesoporous oxide loaded with itraconazole, or of pure crystalline itraconazole as a control, was also investigated and results are shown in FIG. 21. The ordered mesoporous oxide loaded with itraconazole resulted in disintegration times of less than 1 minute, followed by a good dispersion of the loaded ordered mesoporous oxide into the dissolution medium (about 50% release after 2 minutes), in contrast to the control. From these data, it is clear that the excipients had no significant influence on the dissolution profile of crystalline itraconazole or on itraconazole release from ordered mesoporous oxide.

EXAMPLE 19

In Vivo Evaluation of an Itraconazole Pharmaceutical Formulation Including an Ordered Mesoporous Oxide Herein Specifically Ordered Mesoporous Silica in Rabbits and in Dogs Two animal species, rabbits and dogs, were selected to investigate whether the fast in vitro release kinetics shown in example 18 can be translated into an increased bioavailability of the drug, due to improved intraluminal dissolution. Three different formulations were assessed:
the ordered mesoporous oxide based pharmaceutical formulation of example 18,
a commercial itraconazole formulation marketed under the trade name Sporanox®, and
crystalline itraconazole.

Details of the rabbits experiments were as follows: New Zealand White rabbits (4-6 months of age, 3.6-4.1 kg, female) were housed, according to Belgian laws and European regulations for animal experiments, in the Central Animal Facilities of the K. U. Leuven. Prior to oral drug administration, the rabbits (n=5) were fasted overnight (>12 hours). After receiving the oral dose, 3 mL of water was administered to facilitate swallowing. After 4 hours, the rabbits had free access to food and water. A wash out period of seven days was allowed between subsequent dose administrations. Blood samples (2.5 mL) were collected from the vena auricularis prior to dosing and at 0.5, 1, 2, 3, 4, 7, 10, 12 and 24 hours after dosing respectively. Immediately after blood collection, plasma was harvested by centrifugation at 2,500 g for 10 minutes. Plasma was then transferred to a fresh Eppendorf tube and frozen at −20° C. prior to analysis.

Details of the dog's experiments were as follows: Marshall Beagle dogs (1.5-3 years of age, 7.1-10.0 kg, male) were housed according to Belgian laws and European regulations for animal experiments, and with free access to water and food. The comparative bioavailability study was performed according to a cross-over design (n=5). After administration of the capsules, 10 mL of water was given to facilitate swallowing. The evaluation of the formulation containing pure crystalline itraconazole was performed with 4 dogs. Blood samples (2.5 mL) were collected from the vena jugularis before dosing and at 0.25, 0.5, 1, 2, 3, 4, 6, 8 hours respectively after dosing. Immediately after blood collection, plasma was harvested by centrifugation at 2,500 g for 10 minutes. Plasma was then transferred to a fresh tube and frozen at −20° C. prior to analysis.

Plasma concentrations of itraconazole and hydroxy-itraconazole were determined by the following HPLC method. To 1 mL of plasma, 100 µL of the internal standard solution was added [R051012 (Janssen Pharmaceutica), 2.5 µM in 0.2 M HCl]. After addition of 500 µL 2M NaOH, itraconazole and hydroxy-itraconazole were extracted with 4 mL diethyl ether. Following centrifugation at 4,000 rpm for 5 minutes, the upper organic layer was transferred into a fresh tube. The organic solvent was evaporated under a gentle stream of air and the extraction residue was dissolved in 200 µL methanol/water mixture (50/50 by volume), of which 99.5 µL was injected into a HPLC system (commercially available from Merck-Hitachi, Darmstadt, Germany) consisting of an Elite LaCrom L-2130 HPLC pump, an autosampler model L-2200 equipped with a 100 µL loop and a UV detector model L-2400. Separations were achieved using a Novapak C-18, 4 µm, under radial compression. The mobile phase consisted of a methanol/25 mM sodium acetate mixture (78/22 by volume) at pH 3.3. The mobile phase was filtered through a 0.45 µm PTFE membrane before use. The flow rate of the mobile phase was maintained at 1.75 mL/min and the effluent was monitored at a wavelength of 265 nm. Itraconazole, hydroxyitraconazole and R051012 were eluted with retention times of 4.5, 8.0 and 11.5 minutes, respectively. The standard curves were linear over the concentration range from 7.8 nM to 500 nM. The intraday reproducibility, expressed as the relative standard deviation, were less than 7.3% for itraconazole and less than 5.4% for hydroxy-itraconazole over the dose range studied (n=6).

The maximal plasma concentrations ($C_{max}$) and the time ($T_{max}$) required to reach $C_{max}$ were determined from the individual time versus concentration profiles. Systemic exposure was determined by calculating $AUC_{0-24h}$ (rabbits) and $AUC_{0-8h}$ (dogs) using the linear trapezoidal rule. Pharmacokinetic parameters between the three formulations tested were statistically compared with the non-parametric Wilcoxon signed-rank test. The level of significance was set at p<0.03 for comparing two out of three groups.

FIG. 22 shows the average plasma concentration versus time curves of itraconazole and the active metabolite hydroxy-itraconazole after dosing itraconazole in rabbits. Consistently with pharmacokinetic data for itraconazole reported in literature, high intersubject variability was encountered in all three cases. Administration of crystalline itraconazole resulted in an $AUC_{0-24}$ value of 520 nM·h and a $T_{max}$ of 10 hours. When the same dose of itraconazole was formulated into ordered mesoporous oxide, the systemic exposure to itraconazole was raised significantly as reflected in an $AUC_{0-24}$ of 1070 nM·h, whilst $T_{max}$ decreased to 4.2 hours. These data confirm the in vitro dissolution enhancement achieved when ordered mesoporous oxide was used as a carrier for itraconazole.

Plasma profiles observed after oral dosing of rabbits with the commercial product Sporanox® resulted in a $C_{max}$ of 130 nM, a $T_{max}$ of 5.2 hours and an $AUC_{0-24}$ of 1150 nM·h.

Figure 23:
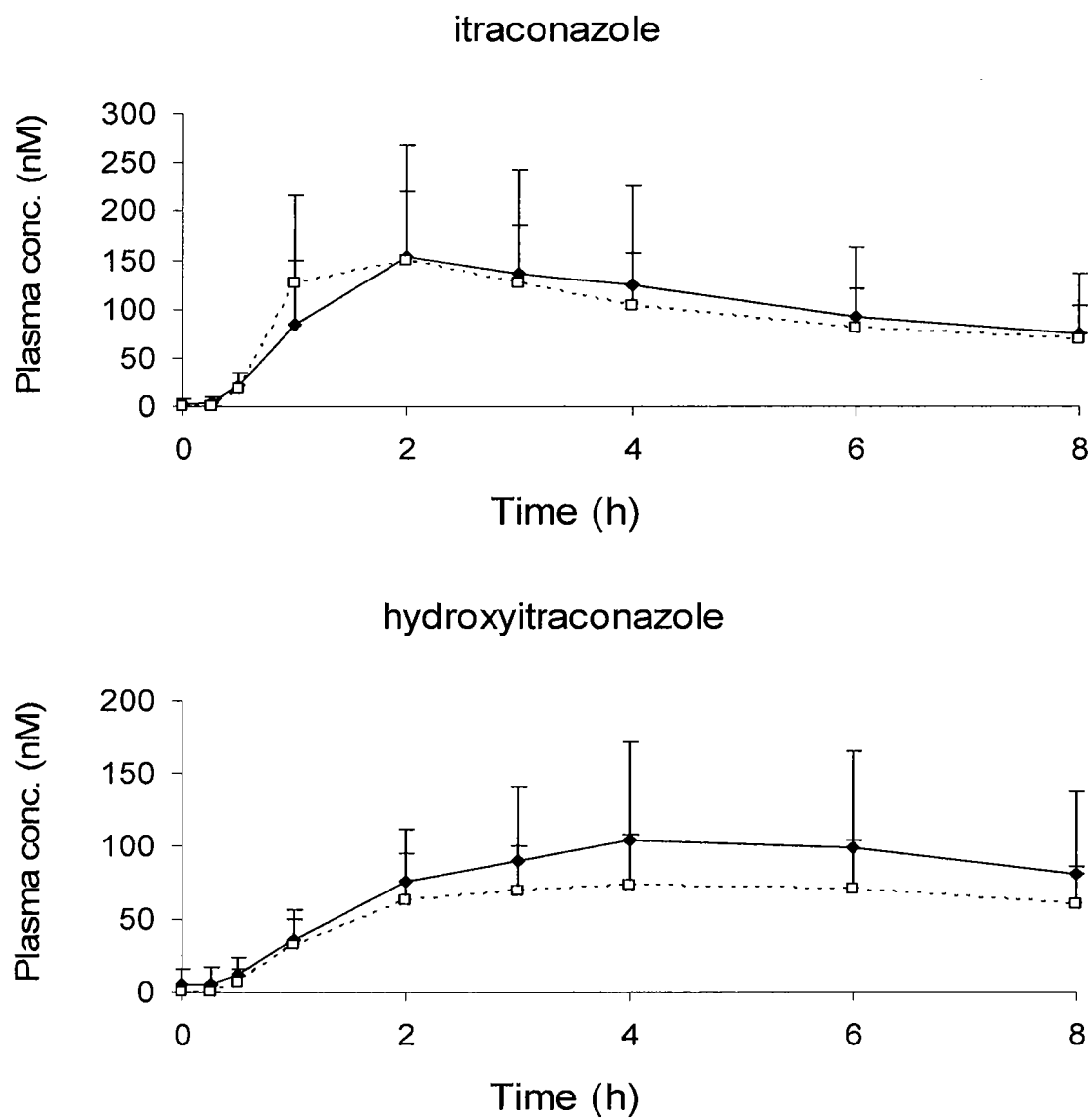
FIG. 23 shows plasma concentration-time profiles of itraconazole and hydroxy-itraconazole after single dosing with ordered mesoporous oxide loaded with itraconazole (♦), Sporanox® (□), or crystalline itraconazole (Δ) in dogs (n=5), concentrations being normalized to the dose provided by the ordered mesoporous oxide capsules (20.4 mg).

In an initial experiment, oral dosing of pure crystalline itraconazole was assessed in 4 dogs. In contrast to rabbits, no systemic concentrations of itraconazole and its main metabolite hydroxy-itraconazole could be observed after such oral dosing of pure crystalline itraconazole. When 20 mg itraconazole was administered to dogs as the ordered mesoporous oxide-based formulation of example 18, oral bioavailability was boosted significantly, a $T_{max}$ of 1.8 hours, a $C_{max}$ of 130 nM and an $AUC_{0-8}$ of 680 nM·h being recorded. FIG. 23 shows the average plasma concentration versus time curves of itraconazole and the active metabolite hydroxy-itraconazole in dogs. When Sporanox® was administered at the same itraconazole dose level, a $C_{max}$ of 160 nM and a systemic exposure $AUC_{0-8}$ of 760 nM·h were obtained.

Table 3 summarizes the AUC values of itraconazole and hydroxy-itraconazole obtained with the different formulations in dogs as well as in rabbits.

TABLE 3

| | Rabbits $AUC_{0-24h}$ (nM · h) | | Dogs $AUC_{0-8h}$ (nM · h) | |
|---|---|---|---|---|
| | itraconazole | hydroxy-itraconazole | itraconazole | hydroxy-itraconazole |
| ordered mesoporous oxide | 1069 ± 278 | 1179 ± 388 | 681 ± 566 | 533 ± 329 |
| Sporanox ® | 1155 ± 424 | 1329 ± 544 | 760 ± 364 | 470 ± 218 |
| crystalline itraconazole | 521 ± 159 | 572 ± 177 | 0 ± 0 | 0 ± 0 |

These data clearly demonstrate that an ordered mesoporous oxide carrier has the capacity to enhance the dissolution of a poorly water-soluble compound such as itraconazole.

EXAMPLE 20

An Example of Media for Dissolution and Transport Experiments

FaSSIF (Fasted State Simulated Intestinal Fluid) was prepared based on blank FaSSIF which is a phosphate buffer obtained by dissolving 0.696 g NaOH (BDH Laboratory Supplies, Poole, England), 7.908 g $NaH_2PO_4 \cdot H_2O$ (Merck, Darmstadt, Germany) and 12.37 g NaCl in 2 L of purified water (18.2 MΩ, Elga, Tex., USA). The pH was adjusted to exactly 6.5 with 1M NaOH. FaSSIF was created by adding 3.23 g sodium taurocholate (ICN Biomedicals, Eschwege, Germany) and 5.9 mL of a solution of lecithin (YDS Chemicals, Heusden, Belgium) in chloroform (100 mg·mL$^{-1}$) to approximately 200 mL blank FaSSIF. This mixture was heated to 80° C. for 15 minutes to remove all chloroform, after which a clear solution was obtained. Subsequently, blank FaSSIF was added up to a volume of 1 l. Some experiments were performed with MES buffered FaSSIF to allow the addition of SGF (simulated gastric fluid, 0.1M HCl containing 0.2 wt. % NaCl) without a significant pH change. MES [2-(N-morpholino)-ethanesulfonic acid, Sigma-Aldrich, Steinheim, Germany] (977.3 mg), sodium taurocholate (179.1 mg) and lecithin solution (655.6 μl) were added to prepare 100 ml of MES-FaSSIF according to the same protocol as mentioned before. As receiver medium for the Caco-2 transport experiments, 0.2 wt. % TPGS (D-α-tocopherol polyethylene glycol 1000 succinate, Eastman, Anglesey, England) in transport medium (TM) [HBSS (Hanks' Balanced Salt Solution) supplemented with glucose (to obtain a final concentration of 25 mM, Sigma-Aldrich, Steinheim, Germany) and Hepes-buffer (10 mM, pH 7.4, N-2-hydroxyethyl-piperazine-N'-2-ethanesulfonic acid, Lonza, Verviers, Belgium)] was used. To maintain sink conditions, TPGS was included in the medium added to the basolateral side of the Caco-2 cell monolayer.

EXAMPLE 21

Characterization of Itraconazole Loaded Ordered Mesoporous Oxide Material Loaded with Itraconazole by (1) the Solvent Method, (2) the Incipient Wetness Impregnation Method, and (3) the Melt Method Using Differential Scanning Calorimetry (DSC) and Porosimetry Based on Nitrogen Adsorption—Release of Itraconazole from Ordered Mesoporous Silica: Influence of the Loading Procedure A sample of ordered mesoporous silica for these tests was prepared according to the following procedure: 6 g of triblock copolymer Pluronic P123 (BTC-Benelux, La Hulpe, Belgium) was dissolved in 180 g of 2M HCl. This mixture was placed in an oil bath at 35° C. under magnetic stirring. An amount of 15.3 g of sodium silicate solution (>27 wt.-% $SiO_2$, Riedel-de Haën, Seelze, Germany) was diluted with 45 g dematerialized water. This mixture was added dropwise to the Pluronic® P123 solution under vigorous stirring. The stirring was allowed to continue for another 5 minutes before switching to static synthesis conditions at 35° C. After 24 hours, the silica suspension was transferred into a Teflon-lined autoclave (K. U. Leuven workshop) and placed in an oven for hydrothermal treatment at a temperature of 90° C. for another 48 hours. Finally, the powder was washed on a 0.45 μm filter (Whatman Schleicher and Schuell, Dassel, Germany) with dematerialized water, dried and calcined at 550° C. for 8 hours under ambient atmosphere to remove the triblock copolymer from the pores.

Figure 24:
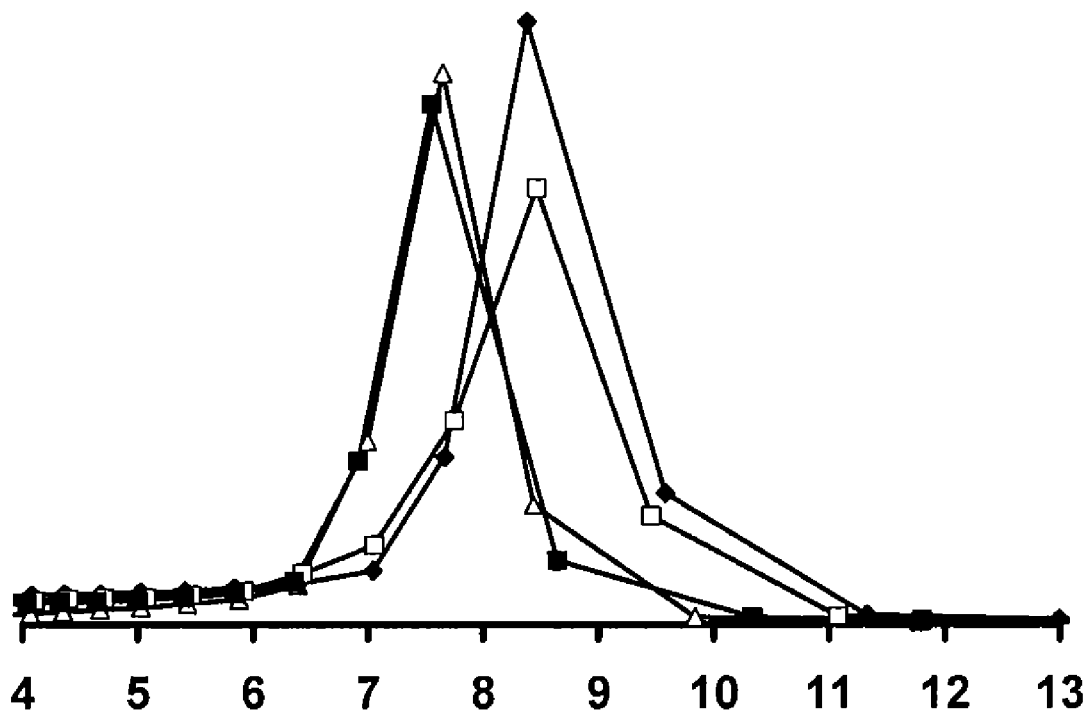
FIG. 24 shows the BJH pore size distribution (nm) of ordered mesoporous silica loaded with 20 wt. % itraconazole using the solvent method (Δ), incipient wetness method (■) and melt method (□) and of the ordered mesoporous oxide support material (♦).
Figure 25:
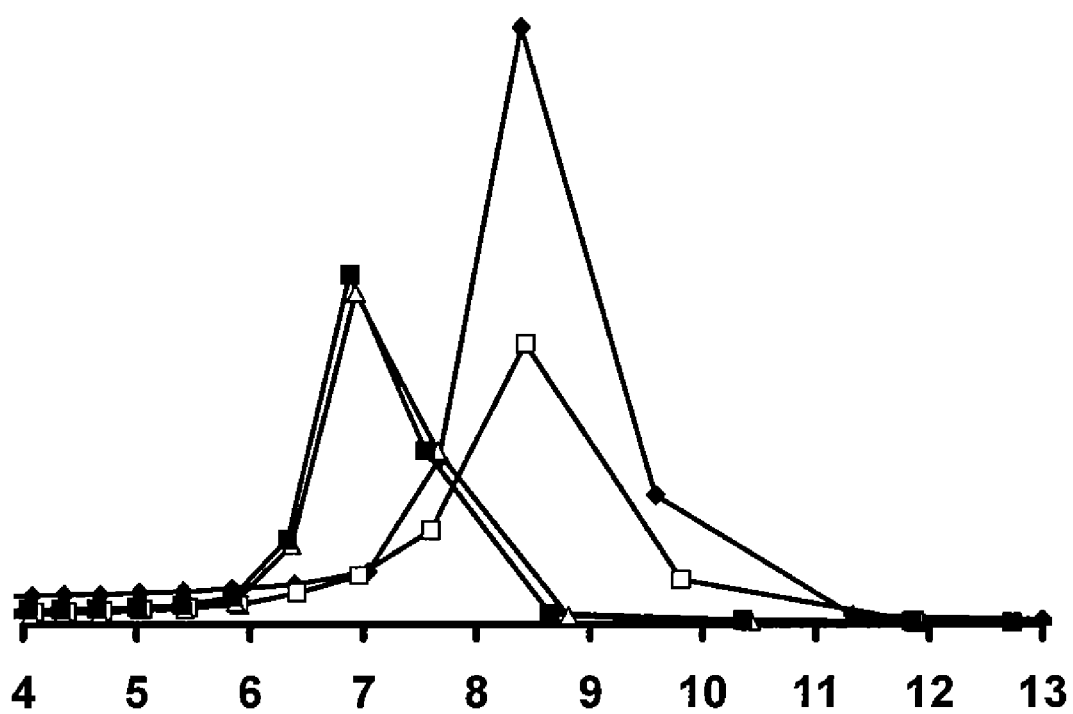
FIG. 25 shows the BJH pore size distribution (nm) of ordered mesoporous material loaded with 30 wt. % itraconazole using the solvent method (Δ), incipient wetness method (■) and melt method (□) and of the ordered mesoporous silica support material (♦).

(i) Nitrogen Adsorption:

Pore size distributions were calculated based on the BJH algorithm (Barret-Joyner-Halenda) of the adsorption branch. FIGS. 24 and 25 represent the effect of loading ordered mesoporous oxide with 20 and 30 wt. % itraconazole, respectively.

When using the solvent and incipient wetness method, the pore diameter decreased, indicating a successful impregnation. In the sample loaded using the melt method, there was no such change of the pore diameter probed by nitrogen adsorption.

Figure 26:
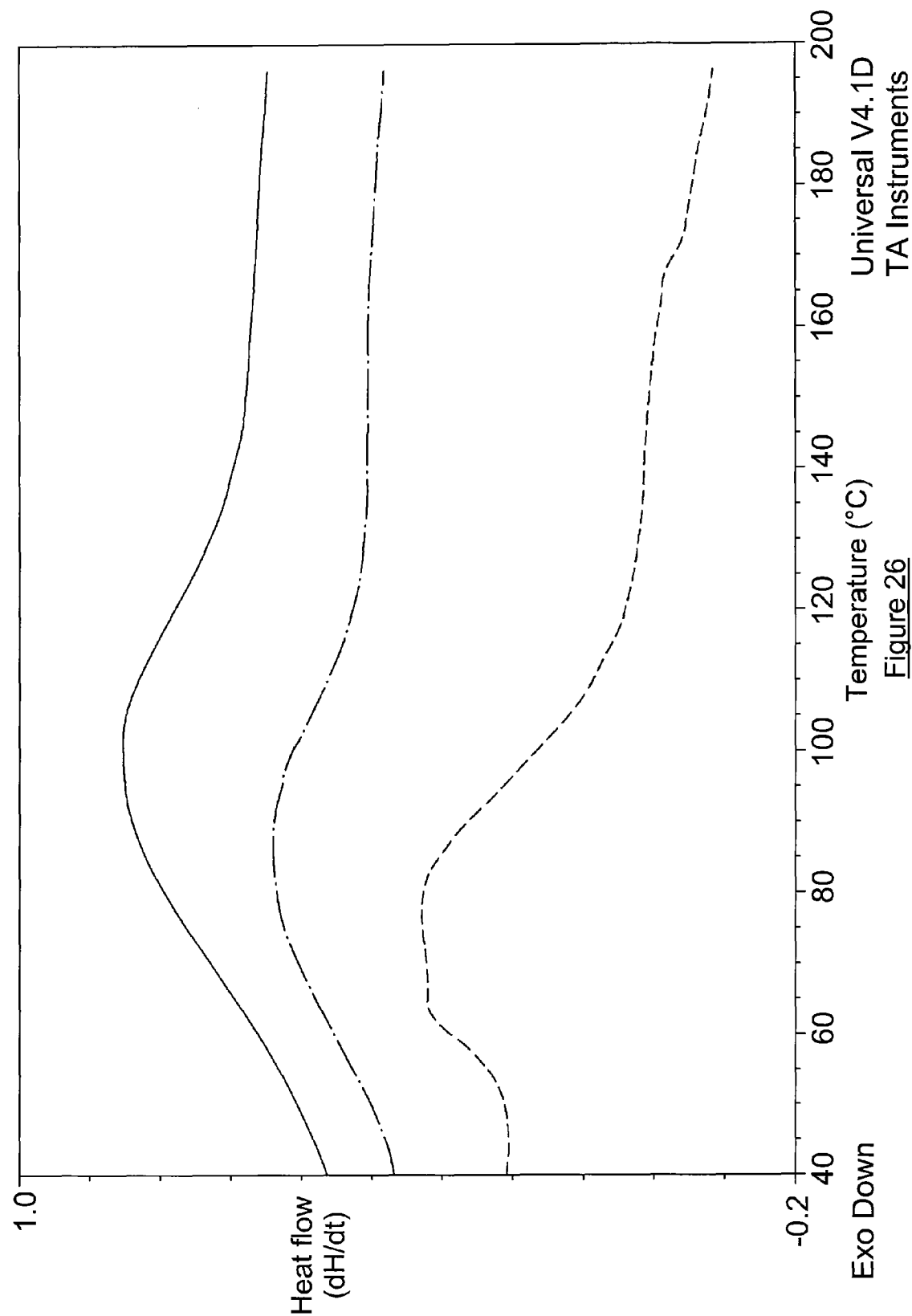
FIG. 26 shows the DSC analysis of ordered mesoporous material loaded with itraconazole using the solvent method (a), incipient wetness method (b) and the melt method (c).

(ii) DSC (Differential Scanning Calorimetry):

The loaded powders were analyzed using a DSC Q1000 (TA Instruments, Brussels, Belgium). The sample was heated from 20° C. to 200° C. at 30° C.·min$^{-1}$. Indium was used to calibrate the temperature scale and the enthalpic response. The samples (weight range 6-10 mg) were analyzed in open aluminum sample pans (TA Instruments, Brussels, Belgium). An amount of 0.1 mg of crystalline or glassy itraconazole was still readily detectable with this procedure. With the solvent method and incipient wetness method, no bulk itraconazole could be detected. The melt method clearly showed crystalline and glassy domains of itraconazole being present. Crystalline itraconazole melts at 168° C., while glassy itraconazole is characterized by a glass transition at 60° C. upon heating (FIG. 26).

Figure 27:
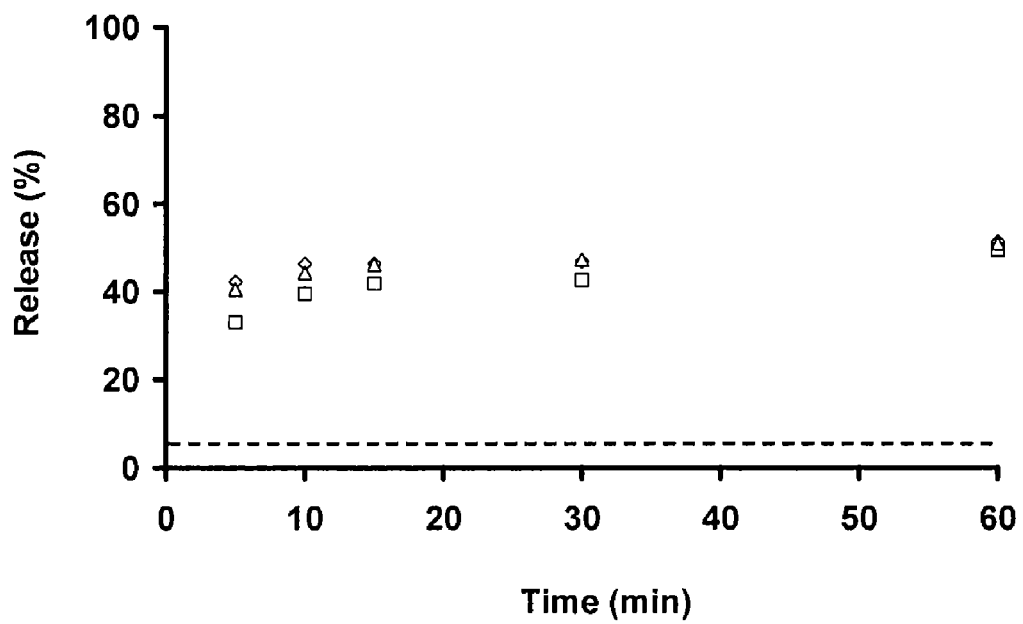
FIG. 27 shows the in vitro release of itraconazole from ordered mesoporous material (theoretical loading of 20 wt. %) in SGF depending on the drug loading procedure: solvent method (◇), melt method (□) and incipient wetness method (Δ). For comparison, the dissolution level of itraconazole from itraconazole crystals is represented as a dotted line ( - - - ).
Figure 28:
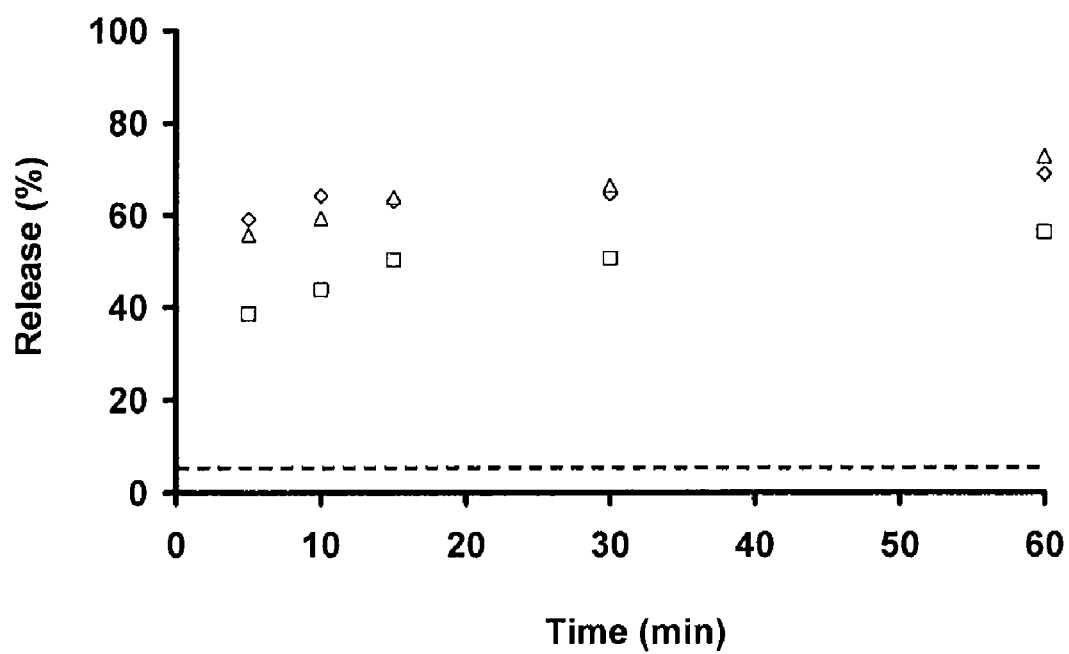
FIG. 28 shows the in vitro release of 30 wt. % itraconazole from ordered mesoporous material in SGF depending on the drug loading procedure: solvent method (◇), melt method (□) and incipient wetness method (Δ). For comparison, the dissolution level of itraconazole from itraconazole crystals is represented as a dotted line ( - - - ).

(iii) In Vitro Release of Itraconazole from Ordered Mesoporous Material in Simulated Gastric Fluid (SGF) See FIG. 27 and FIG. 28.

Release of itraconazole from ordered mesoporous material, loaded using the three different techniques was investigated. The loaded powders were suspended in simulated gastric fluid (0.1 M HCl containing 0.2 wt. % NaCl). The dissolution study was performed in test tubes of 10 mL under gentle agitation using a rotary mixer (Snijders-Tilburg, Tilburg, The Netherlands). The amount of material in the dissolution medium was adjusted to obtain a fixed concentration of drug substance (0.08 mg·mL$^{-1}$). At specific time intervals, samples were collected and the medium was filtered through a 0.45 μm PTFE membrane. Prior to analysis by HPLC, samples were diluted with methanol (1:1) to prevent precipitation during analysis.

From the three samples loaded according to the three methods, the release of itraconazole occurs fast: a release plateau is reached after 15 minutes. With the solvent and incipient wetness impregnation method used for itraconazole loading; the release is faster and the plateau value is higher compared to the melt method. In these preparations, itraconazole is molecularly dispersed over the surface of the pores of the ordered mesoporous silica carrier material. The preparation according to the melt method contains a fraction of the itraconazole in glassy state as evidenced with DSC responsible for the somewhat slower release kinetics. The concentration of dissolved itraconazole obtained from the preparations based on ordered mesoporous material are much higher than that obtained from crystalline itraconazole.

All patents, patent applications, patent application publications, and other publications cited or referred to in this specification are herein incorporated by reference to the same extent as if each independent patent, patent application, patent application publication or publication was specifically and individually indicated to be incorporated by reference.

What is claimed is:

1. A process for the release of a biologically active species comprising the steps of:
   providing a mesoporous oxide-based material having structural order and at least one level of porosity; and
   providing said ordered mesoporous oxide with a fixed or immobilized biologically active species in vivo thereby realizing intraluminally induced pH-independent supersaturation of said biologically active species resulting in enhanced transepithelial transport;
   wherein said biologically active species is a poorly soluble therapeutic drug classified as belonging to Class II or Class IV of the Biopharmaceutical Classification System.

2. The process according to claim 1, wherein said ordered mesoporous oxide has a pore size in the range of 4 to 14 nm.

3. The process according to claim 1, wherein said ordered mesoporous oxide has a pore size in the range of 6 to 12 nm.

4. The process according to claim 1, wherein when said ordered mesoporous oxide-based material has a single level of porosity and structural order it is obtained in the absence of an alpha-tocopherol polyethylene glycol ester templating biomolecule.

5. The process according to claim 1, wherein said ordered mesoporous oxide with said fixed or immobilized biologically active species is provided together with at least one supersaturation-stabilizing agent.

6. The process according to claim 5, wherein said at least one supersaturation-stabilizing agent is hydroxypropyl methyl cellulose, polyacrylic acid, an acrylic acid polymer, or a carboxypolymethylene polymer.

7. The process according to claim 1, wherein said ordered mesoporous oxide based material has two or more levels of porosity and structural order.

8. The process according to claim 7, wherein said two or more levels of porosity and structural order are obtained by assembly of nanometer size building units having zeolite framework, and wherein said assembly proceeds in the presence of one or more amphiphilic non-anionic surfactants.

9. The process according to claim 8, wherein the internal structure of said nanometer size building units does not give rise to Bragg diffraction in a powder X-ray diffraction pattern of said crystalline mesoporous oxide-based material.

10. The process according to claim 1, wherein said fixing or immobilizing said biologically active species in said ordered mesoporous oxide is realized by an incipient wetness impregnation method.

11. The process according to claim 1, wherein said fixing or immobilizing said biologically active species in said ordered mesoporous oxide is realized by melting said biologically active species in said ordered mesoporous oxide.

12. The process according to claim 1, wherein said fixing or immobilizing said biologically active species in said ordered mesoporous oxide is realized by impregnating a high concentration solution of said biologically active species in non-polar solvent into said ordered mesoporous oxide and evaporating said non-polar solvent.

13. The process according to claim 1, wherein the size of said biologically active species is suitable for entrapment into the mesopores of said ordered mesoporous oxide-based material.

14. The process according to claim 1, wherein the molecular weight of said biologically active species is between 200 and 1,000 Daltons.

15. The process according to claim 1, wherein the water solubility of said biologically active species is below 2.5 mg/mL.

16. The process according to claim 1, wherein the water solubility of said biologically active species is between 0.1 and 1 mg/mL.

17. The process according to claim 1, wherein the water solubility of said biologically active species is below 0.1 mg/mL.

18. The process according to claim 1, wherein the water solubility of said biologically active species is below 5 μg/mL.

19. The process according to claim 1, wherein said biologically active species has a polar surface area between 60 Å² and 200 Å².

20. The process according to claim 1, wherein said biologically active species has a polar surface area between 70 Å² and 160 Å².

21. The process according to claim 1, wherein said biologically active species has a polar surface area between 95 Å² and 110 Å².

22. The process according to claim 1, wherein said biologically active species has a partition coefficient between 4 and 9.

23. The process according to claim 1, wherein said biologically active species has a partition coefficient between 5 and 8.

24. The process according to claim 1, wherein said biologically active species has a partition coefficient between 6 and 7.

25. The process according to claim 1, wherein said biologically active species has a molecular weight of said biologically active species is between 200 and 1,000, a partition coefficient between 4 and 9 and a polar surface area between 60 Å² and 200 Å².

26. The process according to claim 25, wherein said biologically active species is a triazole compound.

27. The process according to claim 1, wherein said biologically active species is selected from the group consisting of acetohexamide, ajamaline, amiodarone, aripiprazole, atazanavir, atorvastatin, atovaquone, azithromycin, benazepril, bendroflumethiazide, benserazide, benzbromarone, benzthiazide, betamethasone, benzyl benzoate, bicalutamide, candesartan, carbamazepine, carisoprodol, carvedilol, celecoxib, chloramphenicol, chlorpromazine, chlorpropamide, chlorthalidone, chlorothiazide, clarithromycin, clofibrate, clopidrogel, clozapine, danazol, dapsone, diaminopyrimidines, diaveridine, diazepam, diclofenac, dicumarol, diflunisal, digitoxin, divalproex, docetaxel, efavirenz, ethacrinic acid, ethotoin, etodolac, ezetimibe, fenofibrate, florfenicol, flufenamic acid, furosemide, gemfibrozil, glibenclamide, glimepiride, glutethimide, glyburide, griseofulvin, hydrochlorothiazide, hydrocortisone, hydroflumethiazide, hydroquinine, hydroxyzine pamoate, ibuprofen, imatinib, indinavir sulphate, indomethacin, irbesartan, isotretinoin, itraconazole, ketoconazole, ketoprofen, khellin, lamotrigine, lansoprazole, linezolid, lopinavir, loratidine, lovastatin, meclizine, medroxyprogesteerone acetate, mefenamic acid, metaxalone, methylphenidate, mycophenolate, nabumetone, naproxen, nelfinavir mesylate, nevirapine, nifedipine, nimodipine, nitrazepam, nitrendipine, nitrofurantoin, novalgin, ofloxacin, olanzapine, olmesartan, orlistat, ormetoprim, oxazepam, papaverine, phenazopyridine, phenylbutazone, phenytoin, pioglitazone, prazosin, prednisolone, prednisone, pyrimethamine, quetiapine, raloxifene, reserpine, risperidone, ritonavir, rofecoxib, rosuvastatin, saperconazole, saquinavir, simvastatin, sirolimus, spironolactone, succinylsulfathiazole, sulfabenzamide, sulfadiazine, sulfadimethoxine, sulfamerazine sulfamethazine, sulfamethizole, sulfamethoxazole, sulfamethoxypyridazine, sulfaphenazole, sulfathiazole, sulfisoxazole, sulpiride, tadalafil, tamoxifen, telmisartan, temazepam, temozolomide, terfenadine, testosterone, trimethoprim and troglitazone.

* * * * *